United States Patent [19]

Wahl et al.

[11] Patent Number: 6,022,521
[45] Date of Patent: Feb. 8, 2000

[54] METHOD OF ESTABLISHING THE OPTIMAL RADIATION DOSE FOR RADIOPHARMACEUTICAL TREATMENT OF DISEASE

[75] Inventors: Richard L. Wahl, Ann Arbor; Kenneth R. Zasadny, Wyandote, both of Mich.

[73] Assignee: The Regents of the University of Michigan, Ann Arbor, Mich.

[21] Appl. No.: 08/538,095

[22] Filed: Oct. 2, 1995

Related U.S. Application Data

[63] Continuation-in-part of application No. 08/433,674, May 4, 1995, abandoned.

[51] Int. Cl.[7] .............................. A61K 51/10; A61B 6/00; A61N 1/30
[52] U.S. Cl. ........................ 424/1.49; 424/1.11; 128/659; 604/20
[58] Field of Search ................................... 424/1.11, 1.65, 424/1.61, 1.49; 128/659; 604/20

[56] References Cited

PUBLICATIONS

Robert Loevinger et alia, "A Revised Schema for Calculating the Absorbed Dose from Biologically DistrIbuted Radionuclides", *Medical International Radiation Dose (MIRD) Committee of the Society of Nuclear Medicine*, Pamphlet No. 1, Revised, Mar., 1976, pp. 3–10.

"Importance of the Terminal Portion of Tumor Time–Activity Curve in Determining Tumor Dosimetry in Radioimmunotherapy", *The Journal of Nuclear Medicine*, vol. 32, No. 6, Jun. 1991, pp. 1314–1315.

Kaminski et alia, "Imaging, Dosimetry, and Radioimmunotherapy with Iodine 131–Labeled Anti–CD37 Antibody in B–Cell Lymphoma", *Journal of Clinical Oncology*, vol. 10, No. 11, Nov. 1992, pp. 1696–1711.

Zasadny et alia, "Standardized Uptake Values of Normal Tissues at Pet with 2–[Fluorine–18]–Fluoro–2–Deoxy–D–Glucose: Variations with Body Weight and a Method for Correction", *Radiology*, Dec. 1993, pp. 847–850.

Kaminski et alia, "Radioimmunotherapy of B–Cell Lymphoma with [$^{131}$I]Anti–B1 (Anti–CD20) Antibody", *The New England Journal of Medicine*, Aug. 12, 1993, pp. 459–465.

Koral et alia, "CT–Spect Fusion Plus Conjugate Views for Determining Dosimetry in Iodine–131–Monoclonal Antibody Therapy of Lymphoma Patients", *The Journal of Nuclear Medicine*, vol. 35, No. 10, Oct. 1994, pp. 1714–1720.

K.R. Zasadny et alia, Abstract for "Correlation of Dosimetric Parameters with Hematological Toxicity after Radioimmunotherapy of Non–Hodgkin's Lymphoma with I–131 Anti–B1. Utility of a New Parameter: Total Body Dose–Lean", *The Journal of Nuclear Medicine*, vol., 36, No. 5, May 1995, Abstract Book.

*Primary Examiner*—Gary E. Hollinden
*Assistant Examiner*—Michael G. Hartley
*Attorney, Agent, or Firm*—Harness, Dickey & Pierce, P.L.C.

[57] ABSTRACT

A method for determining the number of millicuries to be administered to a patient as a dose so as to establish a given centigray (cGy) dose to either the patient's lean body or the patient's total body. The method includes the steps of injecting a radioactive tracer into a patient, determining radiation levels in the whole body, calculating a geometric mean based on the radiation levels, determining the percent-injected activity remaining in the body at each time point, plotting the percent-injected activity versus calculated time from infusion on a log-linear graph, determining the effective half live and the rate of clearance from the log-linear graph, cross-indexing the effective half-life value with the patient's body weight, and multiplying the determined amount of therapeutic millicuries per centigray by the amount of desired centigray to be administered.

11 Claims, 47 Drawing Sheets

Fig. 1

Diagnostic Total Body Clearance

Patient: _____

Infusion Date/time: _____

Injected activity: _____ mCi

Patient Lean Body (or Total Body) mass: _____ Kg

Projected TB-lean (or TB) dose: _____ cGy

| nominal time point | time post infusion [hrs] | anterior whole body | posterior whole body | background | GM | GMnet | %injected activity |
|---|---|---|---|---|---|---|---|
| immed post infusion | | | | | | | |
| 1 day post | | | | | | | |
| 2 day post | | | | | | | |
| 3 day post | | | | | | | |
| 4 day post | | | | | | | |
| 5 day post | | | | | | | |
| 6 day post | | | | | | | |
| 7 day post | | | | | | | |

Effective half life: _____ hrs

A0 (from table lookup): _____ mCi/cGy

Prescribed therapy activity (for TBdose-lean or TBdose) = A0 * Projected TB-lean dose: _____ mCi

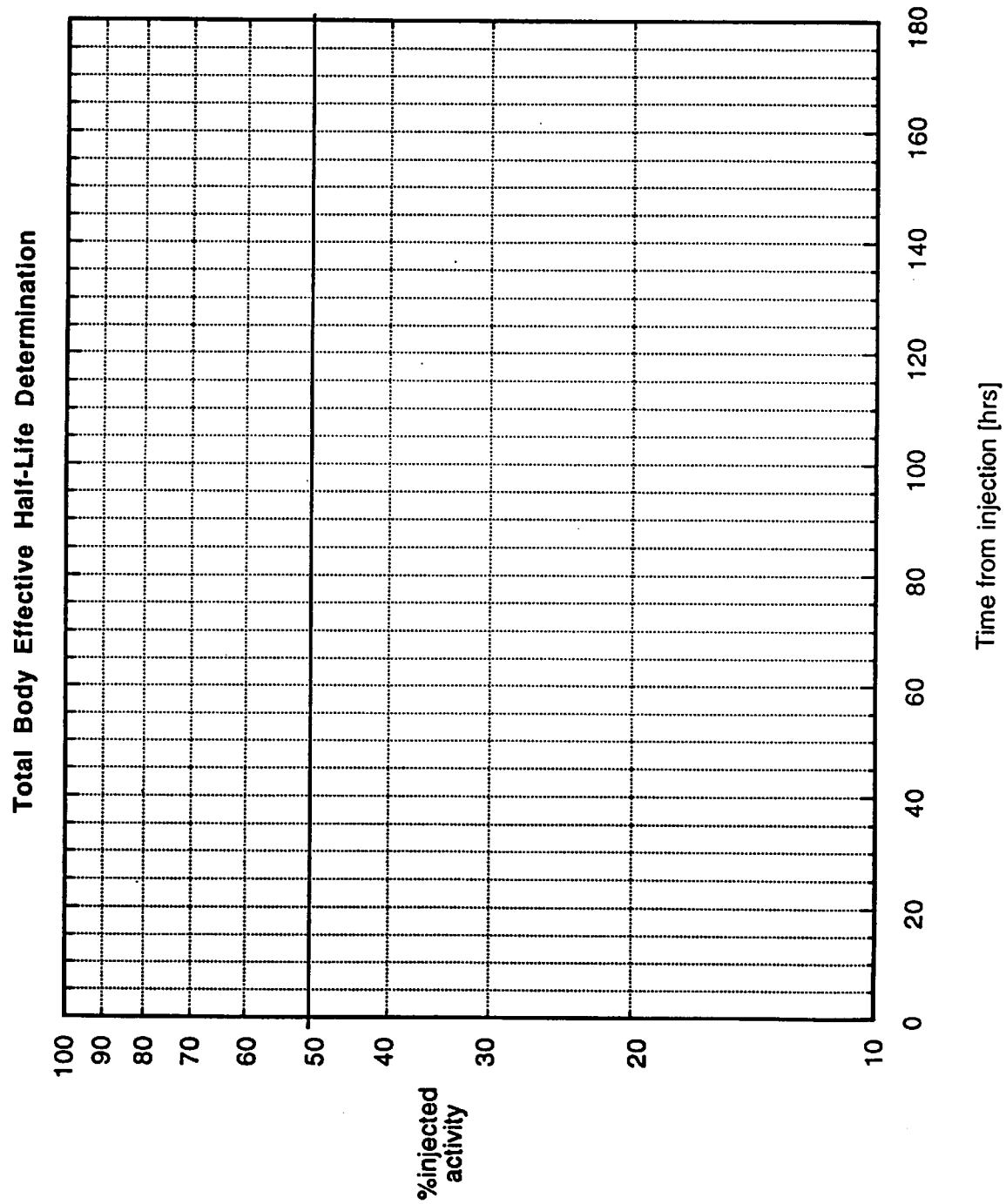

Fig. 7a

| mass[Kg] | 30 | 31 | 32 | 33 | 34 | 35 | 36 |
|---|---|---|---|---|---|---|---|
| 40 | 1.429 | 1.383 | 1.339 | 1.299 | 1.261 | 1.225 | 1.191 |
| 41 | 1.461 | 1.414 | 1.370 | 1.328 | 1.289 | 1.252 | 1.217 |
| 42 | 1.493 | 1.445 | 1.400 | 1.357 | 1.317 | 1.280 | 1.244 |
| 43 | 1.525 | 1.476 | 1.430 | 1.387 | 1.346 | 1.307 | 1.271 |
| 44 | 1.557 | 1.507 | 1.460 | 1.416 | 1.374 | 1.335 | 1.298 |
| 45 | 1.589 | 1.538 | 1.490 | 1.445 | 1.402 | 1.362 | 1.324 |
| 46 | 1.621 | 1.569 | 1.520 | 1.474 | 1.430 | 1.389 | 1.351 |
| 47 | 1.653 | 1.599 | 1.549 | 1.502 | 1.458 | 1.417 | 1.377 |
| 48 | 1.684 | 1.630 | 1.579 | 1.531 | 1.486 | 1.444 | 1.404 |
| 49 | 1.716 | 1.661 | 1.609 | 1.560 | 1.514 | 1.471 | 1.430 |
| 50 | 1.747 | 1.691 | 1.638 | 1.589 | 1.542 | 1.498 | 1.456 |
| 51 | 1.779 | 1.722 | 1.668 | 1.617 | 1.570 | 1.525 | 1.482 |
| 52 | 1.810 | 1.752 | 1.697 | 1.646 | 1.597 | 1.552 | 1.509 |
| 53 | 1.842 | 1.782 | 1.727 | 1.674 | 1.625 | 1.579 | 1.535 |
| 54 | 1.873 | 1.813 | 1.756 | 1.703 | 1.653 | 1.606 | 1.561 |
| 55 | 1.904 | 1.843 | 1.785 | 1.731 | 1.680 | 1.632 | 1.587 |
| 56 | 1.936 | 1.873 | 1.815 | 1.760 | 1.708 | 1.659 | 1.613 |
| 57 | 1.967 | 1.903 | 1.844 | 1.788 | 1.735 | 1.686 | 1.639 |
| 58 | 1.998 | 1.933 | 1.873 | 1.816 | 1.763 | 1.712 | 1.665 |
| 59 | 2.029 | 1.963 | 1.902 | 1.844 | 1.790 | 1.739 | 1.691 |
| 60 | 2.060 | 1.993 | 1.931 | 1.873 | 1.818 | 1.766 | 1.717 |
| 61 | 2.091 | 2.023 | 1.960 | 1.901 | 1.845 | 1.792 | 1.742 |
| 62 | 2.122 | 2.053 | 1.989 | 1.929 | 1.872 | 1.819 | 1.768 |
| 63 | 2.152 | 2.083 | 2.018 | 1.957 | 1.899 | 1.845 | 1.794 |
| 64 | 2.183 | 2.113 | 2.047 | 1.985 | 1.926 | 1.871 | 1.819 |
| 65 | 2.214 | 2.143 | 2.076 | 2.013 | 1.953 | 1.898 | 1.845 |
| 66 | 2.245 | 2.172 | 2.104 | 2.040 | 1.980 | 1.924 | 1.870 |
| 67 | 2.275 | 2.202 | 2.133 | 2.068 | 2.008 | 1.950 | 1.896 |
| 68 | 2.306 | 2.231 | 2.162 | 2.096 | 2.035 | 1.976 | 1.922 |
| 69 | 2.336 | 2.261 | 2.190 | 2.124 | 2.062 | 2.003 | 1.947 |
| 70 | 2.367 | 2.291 | 2.219 | 2.152 | 2.088 | 2.029 | 1.972 |
| 71 | 2.398 | 2.320 | 2.248 | 2.180 | 2.115 | 2.055 | 1.998 |
| 72 | 2.428 | 2.350 | 2.276 | 2.207 | 2.142 | 2.081 | 2.023 |
| 73 | 2.459 | 2.379 | 2.305 | 2.235 | 2.169 | 2.107 | 2.049 |
| 74 | 2.489 | 2.409 | 2.333 | 2.263 | 2.196 | 2.133 | 2.074 |
| 75 | 2.520 | 2.438 | 2.362 | 2.290 | 2.223 | 2.160 | 2.100 |
| 76 | 2.550 | 2.468 | 2.391 | 2.318 | 2.250 | 2.186 | 2.125 |
| 77 | 2.580 | 2.497 | 2.419 | 2.346 | 2.277 | 2.212 | 2.150 |
| 78 | 2.610 | 2.526 | 2.447 | 2.373 | 2.303 | 2.238 | 2.175 |
| 79 | 2.641 | 2.555 | 2.476 | 2.401 | 2.330 | 2.263 | 2.201 |
| 80 | 2.671 | 2.585 | 2.504 | 2.428 | 2.357 | 2.289 | 2.226 |
| 81 | 2.701 | 2.614 | 2.532 | 2.455 | 2.383 | 2.315 | 2.251 |
| 82 | 2.731 | 2.642 | 2.560 | 2.482 | 2.409 | 2.340 | 2.275 |
| 83 | 2.760 | 2.671 | 2.588 | 2.509 | 2.436 | 2.366 | 2.300 |

Fig. 7b

| mass[Kg] | 37 | 38 | 39 | 40 | 41 | 42 | 43 |
|---|---|---|---|---|---|---|---|
| 40 | 1.158 | 1.128 | 1.099 | 1.071 | 1.045 | 1.020 | 0.997 |
| 41 | 1.185 | 1.153 | 1.124 | 1.096 | 1.069 | 1.044 | 1.019 |
| 42 | 1.211 | 1.179 | 1.149 | 1.120 | 1.093 | 1.066 | 1.042 |
| 43 | 1.237 | 1.204 | 1.173 | 1.144 | 1.116 | 1.089 | 1.064 |
| 44 | 1.263 | 1.229 | 1.198 | 1.168 | 1.139 | 1.112 | 1.086 |
| 45 | 1.288 | 1.255 | 1.222 | 1.192 | 1.163 | 1.135 | 1.109 |
| 46 | 1.314 | 1.280 | 1.247 | 1.216 | 1.186 | 1.158 | 1.131 |
| 47 | 1.340 | 1.305 | 1.271 | 1.239 | 1.209 | 1.180 | 1.153 |
| 48 | 1.366 | 1.330 | 1.296 | 1.263 | 1.232 | 1.203 | 1.175 |
| 49 | 1.391 | 1.355 | 1.320 | 1.287 | 1.256 | 1.226 | 1.197 |
| 50 | 1.417 | 1.380 | 1.344 | 1.311 | 1.279 | 1.248 | 1.219 |
| 51 | 1.442 | 1.404 | 1.368 | 1.334 | 1.302 | 1.271 | 1.241 |
| 52 | 1.468 | 1.429 | 1.393 | 1.358 | 1.325 | 1.293 | 1.263 |
| 53 | 1.493 | 1.454 | 1.417 | 1.381 | 1.348 | 1.316 | 1.285 |
| 54 | 1.519 | 1.479 | 1.441 | 1.405 | 1.371 | 1.338 | 1.307 |
| 55 | 1.544 | 1.503 | 1.465 | 1.428 | 1.393 | 1.360 | 1.329 |
| 56 | 1.569 | 1.528 | 1.489 | 1.452 | 1.416 | 1.383 | 1.350 |
| 57 | 1.595 | 1.553 | 1.513 | 1.475 | 1.439 | 1.405 | 1.372 |
| 58 | 1.620 | 1.577 | 1.537 | 1.498 | 1.462 | 1.427 | 1.394 |
| 59 | 1.645 | 1.602 | 1.561 | 1.522 | 1.485 | 1.449 | 1.416 |
| 60 | 1.670 | 1.626 | 1.585 | 1.545 | 1.507 | 1.471 | 1.437 |
| 61 | 1.695 | 1.651 | 1.608 | 1.568 | 1.530 | 1.493 | 1.459 |
| 62 | 1.720 | 1.675 | 1.632 | 1.591 | 1.552 | 1.515 | 1.480 |
| 63 | 1.745 | 1.699 | 1.656 | 1.614 | 1.575 | 1.537 | 1.502 |
| 64 | 1.770 | 1.724 | 1.679 | 1.637 | 1.597 | 1.559 | 1.523 |
| 65 | 1.795 | 1.748 | 1.703 | 1.660 | 1.620 | 1.581 | 1.545 |
| 66 | 1.820 | 1.772 | 1.727 | 1.683 | 1.642 | 1.603 | 1.566 |
| 67 | 1.845 | 1.796 | 1.750 | 1.706 | 1.665 | 1.625 | 1.587 |
| 68 | 1.870 | 1.820 | 1.774 | 1.729 | 1.687 | 1.647 | 1.609 |
| 69 | 1.894 | 1.845 | 1.797 | 1.752 | 1.710 | 1.669 | 1.630 |
| 70 | 1.919 | 1.869 | 1.821 | 1.775 | 1.732 | 1.691 | 1.651 |
| 71 | 1.944 | 1.893 | 1.844 | 1.798 | 1.754 | 1.713 | 1.673 |
| 72 | 1.969 | 1.917 | 1.868 | 1.821 | 1.777 | 1.734 | 1.694 |
| 73 | 1.993 | 1.941 | 1.891 | 1.844 | 1.799 | 1.756 | 1.715 |
| 74 | 2.018 | 1.965 | 1.915 | 1.867 | 1.821 | 1.778 | 1.737 |
| 75 | 2.043 | 1.989 | 1.938 | 1.890 | 1.844 | 1.800 | 1.758 |
| 76 | 2.067 | 2.013 | 1.961 | 1.912 | 1.866 | 1.821 | 1.779 |
| 77 | 2.092 | 2.037 | 1.985 | 1.935 | 1.888 | 1.843 | 1.800 |
| 78 | 2.117 | 2.061 | 2.008 | 1.958 | 1.910 | 1.865 | 1.821 |
| 79 | 2.141 | 2.085 | 2.031 | 1.980 | 1.932 | 1.886 | 1.842 |
| 80 | 2.165 | 2.108 | 2.054 | 2.003 | 1.954 | 1.908 | 1.863 |
| 81 | 2.190 | 2.132 | 2.077 | 2.025 | 1.976 | 1.929 | 1.884 |
| 82 | 2.214 | 2.156 | 2.100 | 2.048 | 1.998 | 1.950 | 1.905 |
| 83 | 2.238 | 2.179 | 2.123 | 2.070 | 2.020 | 1.972 | 1.926 |

Fig. 7c

| mass[Kg] | 44 | 45 | 46 | 47 | 48 | 49 | 50 |
|---|---|---|---|---|---|---|---|
| 40 | 0.974 | 0.952 | 0.932 | 0.912 | 0.893 | 0.875 | 0.857 |
| 41 | 0.996 | 0.974 | 0.953 | 0.933 | 0.913 | 0.894 | 0.877 |
| 42 | 1.018 | 0.995 | 0.974 | 0.953 | 0.933 | 0.914 | 0.896 |
| 43 | 1.040 | 1.017 | 0.995 | 0.974 | 0.953 | 0.934 | 0.915 |
| 44 | 1.062 | 1.038 | 1.016 | 0.994 | 0.973 | 0.953 | 0.934 |
| 45 | 1.083 | 1.059 | 1.036 | 1.014 | 0.993 | 0.973 | 0.953 |
| 46 | 1.105 | 1.081 | 1.057 | 1.035 | 1.013 | 0.992 | 0.973 |
| 47 | 1.127 | 1.102 | 1.078 | 1.055 | 1.033 | 1.012 | 0.992 |
| 48 | 1.148 | 1.123 | 1.098 | 1.075 | 1.053 | 1.031 | 1.011 |
| 49 | 1.170 | 1.144 | 1.119 | 1.095 | 1.072 | 1.051 | 1.030 |
| 50 | 1.191 | 1.165 | 1.140 | 1.115 | 1.092 | 1.070 | 1.048 |
| 51 | 1.213 | 1.186 | 1.160 | 1.136 | 1.112 | 1.089 | 1.067 |
| 52 | 1.234 | 1.207 | 1.181 | 1.156 | 1.132 | 1.108 | 1.086 |
| 53 | 1.256 | 1.228 | 1.201 | 1.176 | 1.151 | 1.128 | 1.105 |
| 54 | 1.277 | 1.249 | 1.222 | 1.196 | 1.171 | 1.147 | 1.124 |
| 55 | 1.298 | 1.270 | 1.242 | 1.216 | 1.190 | 1.166 | 1.143 |
| 56 | 1.320 | 1.290 | 1.262 | 1.235 | 1.210 | 1.185 | 1.161 |
| 57 | 1.341 | 1.311 | 1.283 | 1.255 | 1.229 | 1.204 | 1.180 |
| 58 | 1.362 | 1.332 | 1.303 | 1.275 | 1.249 | 1.223 | 1.199 |
| 59 | 1.383 | 1.353 | 1.323 | 1.295 | 1.268 | 1.242 | 1.217 |
| 60 | 1.404 | 1.373 | 1.343 | 1.315 | 1.287 | 1.261 | 1.236 |
| 61 | 1.426 | 1.394 | 1.364 | 1.335 | 1.307 | 1.280 | 1.254 |
| 62 | 1.447 | 1.414 | 1.384 | 1.354 | 1.326 | 1.299 | 1.273 |
| 63 | 1.468 | 1.435 | 1.404 | 1.374 | 1.345 | 1.318 | 1.291 |
| 64 | 1.489 | 1.455 | 1.424 | 1.394 | 1.364 | 1.337 | 1.310 |
| 65 | 1.509 | 1.476 | 1.444 | 1.413 | 1.384 | 1.355 | 1.328 |
| 66 | 1.530 | 1.496 | 1.464 | 1.433 | 1.403 | 1.374 | 1.347 |
| 67 | 1.551 | 1.517 | 1.484 | 1.452 | 1.422 | 1.393 | 1.365 |
| 68 | 1.572 | 1.537 | 1.504 | 1.472 | 1.441 | 1.412 | 1.383 |
| 69 | 1.593 | 1.558 | 1.524 | 1.491 | 1.460 | 1.430 | 1.402 |
| 70 | 1.614 | 1.578 | 1.544 | 1.511 | 1.479 | 1.449 | 1.420 |
| 71 | 1.635 | 1.598 | 1.564 | 1.530 | 1.498 | 1.468 | 1.439 |
| 72 | 1.655 | 1.619 | 1.584 | 1.550 | 1.518 | 1.487 | 1.457 |
| 73 | 1.676 | 1.639 | 1.603 | 1.569 | 1.537 | 1.505 | 1.475 |
| 74 | 1.697 | 1.659 | 1.623 | 1.589 | 1.556 | 1.524 | 1.493 |
| 75 | 1.718 | 1.680 | 1.643 | 1.608 | 1.575 | 1.543 | 1.512 |
| 76 | 1.739 | 1.700 | 1.663 | 1.628 | 1.594 | 1.561 | 1.530 |
| 77 | 1.759 | 1.720 | 1.683 | 1.647 | 1.613 | 1.580 | 1.548 |
| 78 | 1.780 | 1.740 | 1.702 | 1.666 | 1.632 | 1.598 | 1.566 |
| 79 | 1.800 | 1.760 | 1.722 | 1.686 | 1.650 | 1.617 | 1.584 |
| 80 | 1.821 | 1.780 | 1.742 | 1.705 | 1.669 | 1.635 | 1.602 |
| 81 | 1.841 | 1.800 | 1.761 | 1.724 | 1.688 | 1.653 | 1.620 |
| 82 | 1.862 | 1.820 | 1.781 | 1.743 | 1.707 | 1.672 | 1.638 |
| 83 | 1.882 | 1.840 | 1.800 | 1.762 | 1.725 | 1.690 | 1.656 |

Fig. 7d

| mass[Kg] | 51 | 52 | 53 | 54 | 55 | 56 | 57 |
|---|---|---|---|---|---|---|---|
| 40 | 0.840 | 0.824 | 0.809 | 0.794 | 0.779 | 0.765 | 0.752 |
| 41 | 0.859 | 0.843 | 0.827 | 0.812 | 0.797 | 0.783 | 0.769 |
| 42 | 0.878 | 0.861 | 0.845 | 0.829 | 0.814 | 0.800 | 0.786 |
| 43 | 0.897 | 0.880 | 0.863 | 0.847 | 0.832 | 0.817 | 0.803 |
| 44 | 0.916 | 0.898 | 0.881 | 0.865 | 0.849 | 0.834 | 0.820 |
| 45 | 0.935 | 0.917 | 0.899 | 0.883 | 0.867 | 0.851 | 0.836 |
| 46 | 0.953 | 0.935 | 0.917 | 0.900 | 0.884 | 0.868 | 0.853 |
| 47 | 0.972 | 0.953 | 0.935 | 0.918 | 0.901 | 0.885 | 0.870 |
| 48 | 0.991 | 0.972 | 0.953 | 0.936 | 0.919 | 0.902 | 0.886 |
| 49 | 1.009 | 0.990 | 0.971 | 0.953 | 0.936 | 0.919 | 0.903 |
| 50 | 1.028 | 1.008 | 0.989 | 0.971 | 0.953 | 0.936 | 0.920 |
| 51 | 1.046 | 1.026 | 1.007 | 0.988 | 0.970 | 0.953 | 0.936 |
| 52 | 1.065 | 1.044 | 1.025 | 1.006 | 0.987 | 0.970 | 0.953 |
| 53 | 1.083 | 1.063 | 1.043 | 1.023 | 1.005 | 0.987 | 0.969 |
| 54 | 1.102 | 1.081 | 1.060 | 1.041 | 1.022 | 1.003 | 0.986 |
| 55 | 1.120 | 1.099 | 1.078 | 1.058 | 1.039 | 1.020 | 1.002 |
| 56 | 1.139 | 1.117 | 1.096 | 1.075 | 1.056 | 1.037 | 1.019 |
| 57 | 1.157 | 1.135 | 1.113 | 1.093 | 1.073 | 1.054 | 1.035 |
| 58 | 1.175 | 1.153 | 1.131 | 1.110 | 1.090 | 1.070 | 1.052 |
| 59 | 1.193 | 1.171 | 1.148 | 1.127 | 1.107 | 1.087 | 1.068 |
| 60 | 1.212 | 1.188 | 1.166 | 1.144 | 1.124 | 1.104 | 1.084 |
| 61 | 1.230 | 1.206 | 1.183 | 1.162 | 1.140 | 1.120 | 1.100 |
| 62 | 1.248 | 1.224 | 1.201 | 1.179 | 1.157 | 1.137 | 1.117 |
| 63 | 1.266 | 1.242 | 1.218 | 1.196 | 1.174 | 1.153 | 1.133 |
| 64 | 1.284 | 1.260 | 1.236 | 1.213 | 1.191 | 1.170 | 1.149 |
| 65 | 1.302 | 1.277 | 1.253 | 1.230 | 1.208 | 1.186 | 1.165 |
| 66 | 1.320 | 1.295 | 1.270 | 1.247 | 1.224 | 1.202 | 1.181 |
| 67 | 1.338 | 1.313 | 1.288 | 1.264 | 1.241 | 1.219 | 1.197 |
| 68 | 1.356 | 1.330 | 1.305 | 1.281 | 1.258 | 1.235 | 1.214 |
| 69 | 1.374 | 1.348 | 1.323 | 1.298 | 1.274 | 1.252 | 1.230 |
| 70 | 1.392 | 1.366 | 1.340 | 1.315 | 1.291 | 1.268 | 1.246 |
| 71 | 1.410 | 1.383 | 1.357 | 1.332 | 1.308 | 1.284 | 1.262 |
| 72 | 1.428 | 1.401 | 1.374 | 1.349 | 1.324 | 1.301 | 1.278 |
| 73 | 1.446 | 1.418 | 1.392 | 1.366 | 1.341 | 1.317 | 1.294 |
| 74 | 1.464 | 1.436 | 1.409 | 1.383 | 1.358 | 1.333 | 1.310 |
| 75 | 1.482 | 1.454 | 1.426 | 1.400 | 1.374 | 1.350 | 1.326 |
| 76 | 1.500 | 1.471 | 1.443 | 1.417 | 1.391 | 1.366 | 1.342 |
| 77 | 1.518 | 1.489 | 1.460 | 1.433 | 1.407 | 1.382 | 1.358 |
| 78 | 1.536 | 1.506 | 1.478 | 1.450 | 1.424 | 1.398 | 1.374 |
| 79 | 1.553 | 1.523 | 1.495 | 1.467 | 1.440 | 1.415 | 1.390 |
| 80 | 1.571 | 1.541 | 1.512 | 1.484 | 1.457 | 1.431 | 1.406 |
| 81 | 1.589 | 1.558 | 1.529 | 1.500 | 1.473 | 1.447 | 1.421 |
| 82 | 1.606 | 1.575 | 1.546 | 1.517 | 1.489 | 1.463 | 1.437 |
| 83 | 1.624 | 1.592 | 1.562 | 1.534 | 1.506 | 1.479 | 1.453 |

Fig. 7e

| mass[Kg] | 58 | 59 | 60 | 61 | 62 | 63 | 64 |
|---|---|---|---|---|---|---|---|
| 40 | 0.739 | 0.726 | 0.714 | 0.703 | 0.691 | 0.680 | 0.670 |
| 41 | 0.756 | 0.743 | 0.730 | 0.718 | 0.707 | 0.696 | 0.685 |
| 42 | 0.772 | 0.759 | 0.747 | 0.734 | 0.722 | 0.711 | 0.700 |
| 43 | 0.789 | 0.776 | 0.763 | 0.750 | 0.738 | 0.726 | 0.715 |
| 44 | 0.805 | 0.792 | 0.779 | 0.766 | 0.753 | 0.741 | 0.730 |
| 45 | 0.822 | 0.808 | 0.795 | 0.782 | 0.769 | 0.757 | 0.745 |
| 46 | 0.838 | 0.824 | 0.810 | 0.797 | 0.784 | 0.772 | 0.760 |
| 47 | 0.855 | 0.840 | 0.826 | 0.813 | 0.800 | 0.787 | 0.775 |
| 48 | 0.871 | 0.856 | 0.842 | 0.828 | 0.815 | 0.802 | 0.790 |
| 49 | 0.888 | 0.873 | 0.858 | 0.844 | 0.830 | 0.817 | 0.804 |
| 50 | 0.904 | 0.889 | 0.874 | 0.859 | 0.846 | 0.832 | 0.819 |
| 51 | 0.920 | 0.905 | 0.889 | 0.875 | 0.861 | 0.847 | 0.834 |
| 52 | 0.936 | 0.921 | 0.905 | 0.890 | 0.876 | 0.862 | 0.849 |
| 53 | 0.953 | 0.937 | 0.921 | 0.906 | 0.891 | 0.877 | 0.863 |
| 54 | 0.969 | 0.952 | 0.937 | 0.921 | 0.906 | 0.892 | 0.878 |
| 55 | 0.985 | 0.968 | 0.952 | 0.937 | 0.921 | 0.907 | 0.893 |
| 56 | 1.001 | 0.984 | 0.968 | 0.952 | 0.937 | 0.922 | 0.907 |
| 57 | 1.017 | 1.000 | 0.983 | 0.967 | 0.952 | 0.937 | 0.922 |
| 58 | 1.033 | 1.016 | 0.999 | 0.983 | 0.967 | 0.951 | 0.936 |
| 59 | 1.049 | 1.032 | 1.014 | 0.998 | 0.982 | 0.966 | 0.951 |
| 60 | 1.065 | 1.047 | 1.030 | 1.013 | 0.997 | 0.981 | 0.966 |
| 61 | 1.081 | 1.063 | 1.045 | 1.028 | 1.012 | 0.996 | 0.980 |
| 62 | 1.097 | 1.079 | 1.061 | 1.043 | 1.027 | 1.010 | 0.995 |
| 63 | 1.113 | 1.094 | 1.076 | 1.059 | 1.042 | 1.025 | 1.009 |
| 64 | 1.129 | 1.110 | 1.092 | 1.074 | 1.056 | 1.040 | 1.023 |
| 65 | 1.145 | 1.126 | 1.107 | 1.089 | 1.071 | 1.054 | 1.038 |
| 66 | 1.161 | 1.141 | 1.122 | 1.104 | 1.086 | 1.069 | 1.052 |
| 67 | 1.177 | 1.157 | 1.138 | 1.119 | 1.101 | 1.083 | 1.067 |
| 68 | 1.193 | 1.172 | 1.153 | 1.134 | 1.116 | 1.098 | 1.081 |
| 69 | 1.208 | 1.188 | 1.168 | 1.149 | 1.131 | 1.113 | 1.095 |
| 70 | 1.224 | 1.204 | 1.183 | 1.164 | 1.145 | 1.127 | 1.110 |
| 71 | 1.240 | 1.219 | 1.199 | 1.179 | 1.160 | 1.142 | 1.124 |
| 72 | 1.256 | 1.235 | 1.214 | 1.194 | 1.175 | 1.156 | 1.138 |
| 73 | 1.272 | 1.250 | 1.229 | 1.209 | 1.190 | 1.171 | 1.152 |
| 74 | 1.287 | 1.266 | 1.245 | 1.224 | 1.204 | 1.185 | 1.167 |
| 75 | 1.303 | 1.281 | 1.260 | 1.239 | 1.219 | 1.200 | 1.181 |
| 76 | 1.319 | 1.297 | 1.275 | 1.254 | 1.234 | 1.214 | 1.195 |
| 77 | 1.335 | 1.312 | 1.290 | 1.269 | 1.248 | 1.229 | 1.209 |
| 78 | 1.350 | 1.327 | 1.305 | 1.284 | 1.263 | 1.243 | 1.224 |
| 79 | 1.366 | 1.343 | 1.320 | 1.299 | 1.278 | 1.257 | 1.238 |
| 80 | 1.381 | 1.358 | 1.335 | 1.313 | 1.292 | 1.272 | 1.252 |
| 81 | 1.397 | 1.373 | 1.350 | 1.328 | 1.307 | 1.286 | 1.266 |
| 82 | 1.412 | 1.388 | 1.365 | 1.343 | 1.321 | 1.300 | 1.280 |
| 83 | 1.428 | 1.404 | 1.380 | 1.358 | 1.336 | 1.314 | 1.294 |

Fig. 7f

| mass[Kg] | 65 | 66 | 67 | 68 | 69 | 70 | 71 |
|---|---|---|---|---|---|---|---|
| 40 | 0.659 | 0.649 | 0.640 | 0.630 | 0.621 | 0.612 | 0.604 |
| 41 | 0.674 | 0.664 | 0.654 | 0.645 | 0.635 | 0.626 | 0.617 |
| 42 | 0.689 | 0.679 | 0.669 | 0.659 | 0.649 | 0.640 | 0.631 |
| 43 | 0.704 | 0.693 | 0.683 | 0.673 | 0.663 | 0.654 | 0.644 |
| 44 | 0.719 | 0.708 | 0.697 | 0.687 | 0.677 | 0.667 | 0.658 |
| 45 | 0.733 | 0.722 | 0.712 | 0.701 | 0.691 | 0.681 | 0.671 |
| 46 | 0.748 | 0.737 | 0.726 | 0.715 | 0.705 | 0.695 | 0.685 |
| 47 | 0.763 | 0.751 | 0.740 | 0.729 | 0.719 | 0.708 | 0.698 |
| 48 | 0.777 | 0.766 | 0.754 | 0.743 | 0.732 | 0.722 | 0.712 |
| 49 | 0.792 | 0.780 | 0.768 | 0.757 | 0.746 | 0.735 | 0.725 |
| 50 | 0.807 | 0.794 | 0.782 | 0.771 | 0.760 | 0.749 | 0.738 |
| 51 | 0.821 | 0.809 | 0.797 | 0.785 | 0.773 | 0.762 | 0.752 |
| 52 | 0.836 | 0.823 | 0.811 | 0.799 | 0.787 | 0.776 | 0.765 |
| 53 | 0.850 | 0.837 | 0.825 | 0.813 | 0.801 | 0.789 | 0.778 |
| 54 | 0.865 | 0.851 | 0.839 | 0.826 | 0.814 | 0.803 | 0.791 |
| 55 | 0.879 | 0.866 | 0.853 | 0.840 | 0.828 | 0.816 | 0.805 |
| 56 | 0.893 | 0.880 | 0.867 | 0.854 | 0.842 | 0.830 | 0.818 |
| 57 | 0.908 | 0.894 | 0.881 | 0.868 | 0.855 | 0.843 | 0.831 |
| 58 | 0.922 | 0.908 | 0.895 | 0.881 | 0.869 | 0.856 | 0.844 |
| 59 | 0.936 | 0.922 | 0.908 | 0.895 | 0.882 | 0.870 | 0.857 |
| 60 | 0.951 | 0.936 | 0.922 | 0.909 | 0.896 | 0.883 | 0.870 |
| 61 | 0.965 | 0.950 | 0.936 | 0.922 | 0.909 | 0.896 | 0.883 |
| 62 | 0.979 | 0.964 | 0.950 | 0.936 | 0.922 | 0.909 | 0.896 |
| 63 | 0.993 | 0.978 | 0.964 | 0.950 | 0.936 | 0.922 | 0.909 |
| 64 | 1.008 | 0.992 | 0.978 | 0.963 | 0.949 | 0.936 | 0.922 |
| 65 | 1.022 | 1.006 | 0.991 | 0.977 | 0.963 | 0.949 | 0.935 |
| 66 | 1.036 | 1.020 | 1.005 | 0.990 | 0.976 | 0.962 | 0.948 |
| 67 | 1.050 | 1.034 | 1.019 | 1.004 | 0.989 | 0.975 | 0.961 |
| 68 | 1.064 | 1.048 | 1.032 | 1.017 | 1.003 | 0.988 | 0.974 |
| 69 | 1.078 | 1.062 | 1.046 | 1.031 | 1.016 | 1.001 | 0.987 |
| 70 | 1.092 | 1.076 | 1.060 | 1.044 | 1.029 | 1.014 | 1.000 |
| 71 | 1.107 | 1.090 | 1.074 | 1.058 | 1.042 | 1.028 | 1.013 |
| 72 | 1.121 | 1.104 | 1.087 | 1.071 | 1.056 | 1.041 | 1.026 |
| 73 | 1.135 | 1.118 | 1.101 | 1.085 | 1.069 | 1.054 | 1.039 |
| 74 | 1.149 | 1.131 | 1.115 | 1.098 | 1.082 | 1.067 | 1.052 |
| 75 | 1.163 | 1.145 | 1.128 | 1.112 | 1.095 | 1.080 | 1.065 |
| 76 | 1.177 | 1.159 | 1.142 | 1.125 | 1.109 | 1.093 | 1.077 |
| 77 | 1.191 | 1.173 | 1.155 | 1.138 | 1.122 | 1.106 | 1.090 |
| 78 | 1.205 | 1.187 | 1.169 | 1.152 | 1.135 | 1.119 | 1.103 |
| 79 | 1.219 | 1.200 | 1.182 | 1.165 | 1.148 | 1.132 | 1.116 |
| 80 | 1.233 | 1.214 | 1.196 | 1.178 | 1.161 | 1.145 | 1.128 |
| 81 | 1.246 | 1.228 | 1.209 | 1.191 | 1.174 | 1.157 | 1.141 |
| 82 | 1.260 | 1.241 | 1.223 | 1.205 | 1.187 | 1.170 | 1.154 |
| 83 | 1.274 | 1.255 | 1.236 | 1.218 | 1.200 | 1.183 | 1.166 |

Fig. 7g

| mass[Kg] | 72 | 73 | 74 | 75 | 76 | 77 | 78 |
|---|---|---|---|---|---|---|---|
| 40 | 0.595 | 0.587 | 0.579 | 0.571 | 0.564 | 0.557 | 0.549 |
| 41 | 0.609 | 0.600 | 0.592 | 0.584 | 0.577 | 0.569 | 0.562 |
| 42 | 0.622 | 0.614 | 0.605 | 0.597 | 0.589 | 0.582 | 0.574 |
| 43 | 0.635 | 0.627 | 0.618 | 0.610 | 0.602 | 0.594 | 0.587 |
| 44 | 0.649 | 0.640 | 0.631 | 0.623 | 0.615 | 0.607 | 0.599 |
| 45 | 0.662 | 0.653 | 0.644 | 0.636 | 0.627 | 0.619 | 0.611 |
| 46 | 0.675 | 0.666 | 0.657 | 0.648 | 0.640 | 0.632 | 0.623 |
| 47 | 0.689 | 0.679 | 0.670 | 0.661 | 0.652 | 0.644 | 0.636 |
| 48 | 0.702 | 0.692 | 0.683 | 0.674 | 0.665 | 0.656 | 0.648 |
| 49 | 0.715 | 0.705 | 0.696 | 0.686 | 0.677 | 0.669 | 0.660 |
| 50 | 0.728 | 0.718 | 0.708 | 0.699 | 0.690 | 0.681 | 0.672 |
| 51 | 0.741 | 0.731 | 0.721 | 0.712 | 0.702 | 0.693 | 0.684 |
| 52 | 0.754 | 0.744 | 0.734 | 0.724 | 0.715 | 0.705 | 0.696 |
| 53 | 0.767 | 0.757 | 0.747 | 0.737 | 0.727 | 0.718 | 0.708 |
| 54 | 0.780 | 0.770 | 0.759 | 0.749 | 0.739 | 0.730 | 0.720 |
| 55 | 0.794 | 0.783 | 0.772 | 0.762 | 0.752 | 0.742 | 0.732 |
| 56 | 0.807 | 0.795 | 0.785 | 0.774 | 0.764 | 0.754 | 0.744 |
| 57 | 0.819 | 0.808 | 0.797 | 0.787 | 0.776 | 0.766 | 0.756 |
| 58 | 0.832 | 0.821 | 0.810 | 0.799 | 0.789 | 0.778 | 0.768 |
| 59 | 0.845 | 0.834 | 0.823 | 0.812 | 0.801 | 0.790 | 0.780 |
| 60 | 0.858 | 0.847 | 0.835 | 0.824 | 0.813 | 0.803 | 0.792 |
| 61 | 0.871 | 0.859 | 0.848 | 0.836 | 0.825 | 0.815 | 0.804 |
| 62 | 0.884 | 0.872 | 0.860 | 0.849 | 0.837 | 0.827 | 0.816 |
| 63 | 0.897 | 0.885 | 0.873 | 0.861 | 0.850 | 0.839 | 0.828 |
| 64 | 0.910 | 0.897 | 0.885 | 0.873 | 0.862 | 0.851 | 0.840 |
| 65 | 0.922 | 0.910 | 0.898 | 0.886 | 0.874 | 0.863 | 0.852 |
| 66 | 0.935 | 0.922 | 0.910 | 0.898 | 0.886 | 0.874 | 0.863 |
| 67 | 0.948 | 0.935 | 0.922 | 0.910 | 0.898 | 0.886 | 0.875 |
| 68 | 0.961 | 0.948 | 0.935 | 0.922 | 0.910 | 0.898 | 0.887 |
| 69 | 0.974 | 0.960 | 0.947 | 0.935 | 0.922 | 0.910 | 0.899 |
| 70 | 0.986 | 0.973 | 0.960 | 0.947 | 0.934 | 0.922 | 0.910 |
| 71 | 0.999 | 0.985 | 0.972 | 0.959 | 0.946 | 0.934 | 0.922 |
| 72 | 1.012 | 0.998 | 0.984 | 0.971 | 0.958 | 0.946 | 0.934 |
| 73 | 1.024 | 1.010 | 0.997 | 0.983 | 0.971 | 0.958 | 0.946 |
| 74 | 1.037 | 1.023 | 1.009 | 0.996 | 0.983 | 0.970 | 0.957 |
| 75 | 1.050 | 1.035 | 1.021 | 1.008 | 0.995 | 0.982 | 0.969 |
| 76 | 1.062 | 1.048 | 1.034 | 1.020 | 1.007 | 0.993 | 0.981 |
| 77 | 1.075 | 1.060 | 1.046 | 1.032 | 1.019 | 1.005 | 0.992 |
| 78 | 1.088 | 1.073 | 1.058 | 1.044 | 1.030 | 1.017 | 1.004 |
| 79 | 1.100 | 1.085 | 1.071 | 1.056 | 1.042 | 1.029 | 1.016 |
| 80 | 1.113 | 1.098 | 1.083 | 1.068 | 1.054 | 1.041 | 1.027 |
| 81 | 1.125 | 1.110 | 1.095 | 1.080 | 1.066 | 1.052 | 1.039 |
| 82 | 1.138 | 1.122 | 1.107 | 1.092 | 1.078 | 1.064 | 1.050 |
| 83 | 1.150 | 1.134 | 1.119 | 1.104 | 1.090 | 1.075 | 1.062 |

Fig. 7h

| mass[Kg] | 79 | 80 | 81 | 82 | 83 | 84 | 85 |
|---|---|---|---|---|---|---|---|
| 40 | 0.543 | 0.536 | 0.529 | 0.523 | 0.516 | 0.510 | 0.504 |
| 41 | 0.555 | 0.548 | 0.541 | 0.534 | 0.528 | 0.522 | 0.516 |
| 42 | 0.567 | 0.560 | 0.553 | 0.546 | 0.540 | 0.533 | 0.527 |
| 43 | 0.579 | 0.572 | 0.565 | 0.558 | 0.551 | 0.545 | 0.538 |
| 44 | 0.591 | 0.584 | 0.577 | 0.570 | 0.563 | 0.556 | 0.550 |
| 45 | 0.603 | 0.596 | 0.589 | 0.581 | 0.574 | 0.568 | 0.561 |
| 46 | 0.616 | 0.608 | 0.600 | 0.593 | 0.586 | 0.579 | 0.572 |
| 47 | 0.628 | 0.620 | 0.612 | 0.605 | 0.597 | 0.590 | 0.583 |
| 48 | 0.640 | 0.632 | 0.624 | 0.616 | 0.609 | 0.602 | 0.594 |
| 49 | 0.652 | 0.643 | 0.636 | 0.628 | 0.620 | 0.613 | 0.606 |
| 50 | 0.664 | 0.655 | 0.647 | 0.639 | 0.632 | 0.624 | 0.617 |
| 51 | 0.676 | 0.667 | 0.659 | 0.651 | 0.643 | 0.635 | 0.628 |
| 52 | 0.687 | 0.679 | 0.671 | 0.662 | 0.654 | 0.647 | 0.639 |
| 53 | 0.699 | 0.691 | 0.682 | 0.674 | 0.666 | 0.658 | 0.650 |
| 54 | 0.711 | 0.702 | 0.694 | 0.685 | 0.677 | 0.669 | 0.661 |
| 55 | 0.723 | 0.714 | 0.705 | 0.697 | 0.688 | 0.680 | 0.672 |
| 56 | 0.735 | 0.726 | 0.717 | 0.708 | 0.700 | 0.691 | 0.683 |
| 57 | 0.747 | 0.738 | 0.728 | 0.720 | 0.711 | 0.702 | 0.694 |
| 58 | 0.759 | 0.749 | 0.740 | 0.731 | 0.722 | 0.714 | 0.705 |
| 59 | 0.770 | 0.761 | 0.751 | 0.742 | 0.733 | 0.725 | 0.716 |
| 60 | 0.782 | 0.772 | 0.763 | 0.754 | 0.745 | 0.736 | 0.727 |
| 61 | 0.794 | 0.784 | 0.774 | 0.765 | 0.756 | 0.747 | 0.738 |
| 62 | 0.806 | 0.796 | 0.786 | 0.776 | 0.767 | 0.758 | 0.749 |
| 63 | 0.817 | 0.807 | 0.797 | 0.787 | 0.778 | 0.769 | 0.760 |
| 64 | 0.829 | 0.819 | 0.809 | 0.799 | 0.789 | 0.780 | 0.771 |
| 65 | 0.841 | 0.830 | 0.820 | 0.810 | 0.800 | 0.791 | 0.781 |
| 66 | 0.852 | 0.842 | 0.831 | 0.821 | 0.811 | 0.802 | 0.792 |
| 67 | 0.864 | 0.853 | 0.843 | 0.832 | 0.822 | 0.813 | 0.803 |
| 68 | 0.876 | 0.865 | 0.854 | 0.844 | 0.833 | 0.824 | 0.814 |
| 69 | 0.887 | 0.876 | 0.865 | 0.855 | 0.844 | 0.834 | 0.825 |
| 70 | 0.899 | 0.888 | 0.877 | 0.866 | 0.856 | 0.845 | 0.835 |
| 71 | 0.910 | 0.899 | 0.888 | 0.877 | 0.867 | 0.856 | 0.846 |
| 72 | 0.922 | 0.911 | 0.899 | 0.888 | 0.878 | 0.867 | 0.857 |
| 73 | 0.934 | 0.922 | 0.911 | 0.899 | 0.889 | 0.878 | 0.868 |
| 74 | 0.945 | 0.933 | 0.922 | 0.911 | 0.900 | 0.889 | 0.878 |
| 75 | 0.957 | 0.945 | 0.933 | 0.922 | 0.911 | 0.900 | 0.889 |
| 76 | 0.968 | 0.956 | 0.944 | 0.933 | 0.922 | 0.911 | 0.900 |
| 77 | 0.980 | 0.968 | 0.956 | 0.944 | 0.933 | 0.922 | 0.911 |
| 78 | 0.991 | 0.979 | 0.967 | 0.955 | 0.944 | 0.932 | 0.921 |
| 79 | 1.003 | 0.990 | 0.978 | 0.966 | 0.954 | 0.943 | 0.932 |
| 80 | 1.014 | 1.002 | 0.989 | 0.977 | 0.965 | 0.954 | 0.943 |
| 81 | 1.026 | 1.013 | 1.000 | 0.988 | 0.976 | 0.965 | 0.953 |
| 82 | 1.037 | 1.024 | 1.011 | 0.999 | 0.987 | 0.975 | 0.964 |
| 83 | 1.048 | 1.035 | 1.022 | 1.010 | 0.998 | 0.986 | 0.974 |

Fig. 7i

| mass[Kg] | 86 | 87 | 88 | 89 | 90 | 91 | 92 |
|---|---|---|---|---|---|---|---|
| 40 | 0.498 | 0.493 | 0.487 | 0.482 | 0.476 | 0.471 | 0.466 |
| 41 | 0.510 | 0.504 | 0.498 | 0.492 | 0.487 | 0.482 | 0.476 |
| 42 | 0.521 | 0.515 | 0.509 | 0.503 | 0.498 | 0.492 | 0.487 |
| 43 | 0.532 | 0.526 | 0.520 | 0.514 | 0.508 | 0.503 | 0.497 |
| 44 | 0.543 | 0.537 | 0.531 | 0.525 | 0.519 | 0.513 | 0.508 |
| 45 | 0.554 | 0.548 | 0.542 | 0.536 | 0.530 | 0.524 | 0.518 |
| 46 | 0.565 | 0.559 | 0.553 | 0.546 | 0.540 | 0.534 | 0.529 |
| 47 | 0.577 | 0.570 | 0.563 | 0.557 | 0.551 | 0.545 | 0.539 |
| 48 | 0.588 | 0.581 | 0.574 | 0.568 | 0.561 | 0.555 | 0.549 |
| 49 | 0.599 | 0.592 | 0.585 | 0.578 | 0.572 | 0.566 | 0.560 |
| 50 | 0.610 | 0.603 | 0.596 | 0.589 | 0.582 | 0.576 | 0.570 |
| 51 | 0.621 | 0.613 | 0.606 | 0.600 | 0.593 | 0.586 | 0.580 |
| 52 | 0.632 | 0.624 | 0.617 | 0.610 | 0.603 | 0.597 | 0.590 |
| 53 | 0.642 | 0.635 | 0.628 | 0.621 | 0.614 | 0.607 | 0.601 |
| 54 | 0.653 | 0.646 | 0.639 | 0.631 | 0.624 | 0.618 | 0.611 |
| 55 | 0.664 | 0.657 | 0.649 | 0.642 | 0.635 | 0.628 | 0.621 |
| 56 | 0.675 | 0.667 | 0.660 | 0.652 | 0.645 | 0.638 | 0.631 |
| 57 | 0.686 | 0.678 | 0.670 | 0.663 | 0.656 | 0.648 | 0.641 |
| 58 | 0.697 | 0.689 | 0.681 | 0.673 | 0.666 | 0.659 | 0.651 |
| 59 | 0.708 | 0.700 | 0.692 | 0.684 | 0.676 | 0.669 | 0.662 |
| 60 | 0.719 | 0.710 | 0.702 | 0.694 | 0.687 | 0.679 | 0.672 |
| 61 | 0.729 | 0.721 | 0.713 | 0.705 | 0.697 | 0.689 | 0.682 |
| 62 | 0.740 | 0.732 | 0.723 | 0.715 | 0.707 | 0.699 | 0.692 |
| 63 | 0.751 | 0.742 | 0.734 | 0.726 | 0.717 | 0.710 | 0.702 |
| 64 | 0.762 | 0.753 | 0.744 | 0.736 | 0.728 | 0.720 | 0.712 |
| 65 | 0.772 | 0.763 | 0.755 | 0.746 | 0.738 | 0.730 | 0.722 |
| 66 | 0.783 | 0.774 | 0.765 | 0.757 | 0.748 | 0.740 | 0.732 |
| 67 | 0.794 | 0.785 | 0.776 | 0.767 | 0.758 | 0.750 | 0.742 |
| 68 | 0.804 | 0.795 | 0.786 | 0.777 | 0.769 | 0.760 | 0.752 |
| 69 | 0.815 | 0.806 | 0.797 | 0.788 | 0.779 | 0.770 | 0.762 |
| 70 | 0.826 | 0.816 | 0.807 | 0.798 | 0.789 | 0.780 | 0.772 |
| 71 | 0.836 | 0.827 | 0.817 | 0.808 | 0.799 | 0.790 | 0.782 |
| 72 | 0.847 | 0.837 | 0.828 | 0.818 | 0.809 | 0.800 | 0.792 |
| 73 | 0.858 | 0.848 | 0.838 | 0.829 | 0.820 | 0.811 | 0.802 |
| 74 | 0.868 | 0.858 | 0.849 | 0.839 | 0.830 | 0.821 | 0.812 |
| 75 | 0.879 | 0.869 | 0.859 | 0.849 | 0.840 | 0.831 | 0.822 |
| 76 | 0.889 | 0.879 | 0.869 | 0.860 | 0.850 | 0.841 | 0.831 |
| 77 | 0.900 | 0.890 | 0.880 | 0.870 | 0.860 | 0.851 | 0.841 |
| 78 | 0.911 | 0.900 | 0.890 | 0.880 | 0.870 | 0.861 | 0.851 |
| 79 | 0.921 | 0.911 | 0.900 | 0.890 | 0.880 | 0.871 | 0.861 |
| 80 | 0.932 | 0.921 | 0.910 | 0.900 | 0.890 | 0.880 | 0.871 |
| 81 | 0.942 | 0.931 | 0.921 | 0.910 | 0.900 | 0.890 | 0.881 |
| 82 | 0.953 | 0.942 | 0.931 | 0.920 | 0.910 | 0.900 | 0.890 |
| 83 | 0.963 | 0.952 | 0.941 | 0.930 | 0.920 | 0.910 | 0.900 |

Fig. 7j

| mass[Kg] | 93 | 94 | 95 | 96 | 97 |
|---|---|---|---|---|---|
| 40 | 0.461 | 0.456 | 0.451 | 0.446 | 0.442 |
| 41 | 0.471 | 0.466 | 0.461 | 0.457 | 0.452 |
| 42 | 0.482 | 0.477 | 0.472 | 0.467 | 0.462 |
| 43 | 0.492 | 0.487 | 0.482 | 0.477 | 0.472 |
| 44 | 0.502 | 0.497 | 0.492 | 0.487 | 0.482 |
| 45 | 0.513 | 0.507 | 0.502 | 0.497 | 0.491 |
| 46 | 0.523 | 0.517 | 0.512 | 0.507 | 0.501 |
| 47 | 0.533 | 0.527 | 0.522 | 0.516 | 0.511 |
| 48 | 0.543 | 0.538 | 0.532 | 0.526 | 0.521 |
| 49 | 0.554 | 0.548 | 0.542 | 0.536 | 0.531 |
| 50 | 0.564 | 0.558 | 0.552 | 0.546 | 0.540 |
| 51 | 0.574 | 0.568 | 0.562 | 0.556 | 0.550 |
| 52 | 0.584 | 0.578 | 0.572 | 0.566 | 0.560 |
| 53 | 0.594 | 0.588 | 0.582 | 0.576 | 0.570 |
| 54 | 0.604 | 0.598 | 0.592 | 0.585 | 0.579 |
| 55 | 0.614 | 0.608 | 0.601 | 0.595 | 0.589 |
| 56 | 0.624 | 0.618 | 0.611 | 0.605 | 0.599 |
| 57 | 0.634 | 0.628 | 0.621 | 0.615 | 0.608 |
| 58 | 0.644 | 0.638 | 0.631 | 0.624 | 0.618 |
| 59 | 0.654 | 0.648 | 0.641 | 0.634 | 0.628 |
| 60 | 0.664 | 0.657 | 0.650 | 0.644 | 0.637 |
| 61 | 0.674 | 0.667 | 0.660 | 0.653 | 0.647 |
| 62 | 0.684 | 0.677 | 0.670 | 0.663 | 0.656 |
| 63 | 0.694 | 0.687 | 0.680 | 0.673 | 0.666 |
| 64 | 0.704 | 0.697 | 0.689 | 0.682 | 0.675 |
| 65 | 0.714 | 0.707 | 0.699 | 0.692 | 0.685 |
| 66 | 0.724 | 0.716 | 0.709 | 0.701 | 0.694 |
| 67 | 0.734 | 0.726 | 0.718 | 0.711 | 0.704 |
| 68 | 0.744 | 0.736 | 0.728 | 0.721 | 0.713 |
| 69 | 0.754 | 0.746 | 0.738 | 0.730 | 0.723 |
| 70 | 0.764 | 0.755 | 0.747 | 0.740 | 0.732 |
| 71 | 0.773 | 0.765 | 0.757 | 0.749 | 0.742 |
| 72 | 0.783 | 0.775 | 0.767 | 0.759 | 0.751 |
| 73 | 0.793 | 0.785 | 0.776 | 0.768 | 0.760 |
| 74 | 0.803 | 0.794 | 0.786 | 0.778 | 0.770 |
| 75 | 0.813 | 0.804 | 0.796 | 0.787 | 0.779 |
| 76 | 0.823 | 0.814 | 0.805 | 0.797 | 0.789 |
| 77 | 0.832 | 0.823 | 0.815 | 0.806 | 0.798 |
| 78 | 0.842 | 0.833 | 0.824 | 0.816 | 0.807 |
| 79 | 0.852 | 0.843 | 0.834 | 0.825 | 0.817 |
| 80 | 0.862 | 0.852 | 0.843 | 0.835 | 0.826 |
| 81 | 0.871 | 0.862 | 0.853 | 0.844 | 0.835 |
| 82 | 0.881 | 0.871 | 0.862 | 0.853 | 0.844 |
| 83 | 0.890 | 0.881 | 0.872 | 0.863 | 0.854 |

Fig. 7k

| mass[Kg] | 98 | 99 | 100 |
|---|---|---|---|
| 40 | 0.437 | 0.433 | 0.429 |
| 41 | 0.447 | 0.443 | 0.438 |
| 42 | 0.457 | 0.452 | 0.448 |
| 43 | 0.467 | 0.462 | 0.458 |
| 44 | 0.477 | 0.472 | 0.467 |
| 45 | 0.486 | 0.482 | 0.477 |
| 46 | 0.496 | 0.491 | 0.486 |
| 47 | 0.506 | 0.501 | 0.496 |
| 48 | 0.516 | 0.510 | 0.505 |
| 49 | 0.525 | 0.520 | 0.515 |
| 50 | 0.535 | 0.530 | 0.524 |
| 51 | 0.545 | 0.539 | 0.534 |
| 52 | 0.554 | 0.549 | 0.543 |
| 53 | 0.564 | 0.558 | 0.553 |
| 54 | 0.573 | 0.568 | 0.562 |
| 55 | 0.583 | 0.577 | 0.571 |
| 56 | 0.593 | 0.587 | 0.581 |
| 57 | 0.602 | 0.596 | 0.590 |
| 58 | 0.612 | 0.605 | 0.599 |
| 59 | 0.621 | 0.615 | 0.609 |
| 60 | 0.631 | 0.624 | 0.618 |
| 61 | 0.640 | 0.634 | 0.627 |
| 62 | 0.649 | 0.643 | 0.636 |
| 63 | 0.659 | 0.652 | 0.646 |
| 64 | 0.668 | 0.662 | 0.655 |
| 65 | 0.678 | 0.671 | 0.664 |
| 66 | 0.687 | 0.680 | 0.673 |
| 67 | 0.697 | 0.689 | 0.683 |
| 68 | 0.706 | 0.699 | 0.692 |
| 69 | 0.715 | 0.708 | 0.701 |
| 70 | 0.725 | 0.717 | 0.710 |
| 71 | 0.734 | 0.727 | 0.719 |
| 72 | 0.743 | 0.736 | 0.728 |
| 73 | 0.753 | 0.745 | 0.738 |
| 74 | 0.762 | 0.754 | 0.747 |
| 75 | 0.771 | 0.763 | 0.756 |
| 76 | 0.781 | 0.773 | 0.765 |
| 77 | 0.790 | 0.782 | 0.774 |
| 78 | 0.799 | 0.791 | 0.783 |
| 79 | 0.808 | 0.800 | 0.792 |
| 80 | 0.818 | 0.809 | 0.801 |
| 81 | 0.827 | 0.818 | 0.810 |
| 82 | 0.836 | 0.827 | 0.819 |
| 83 | 0.845 | 0.836 | 0.828 |

Fig. 71

| mass[Kg] | 30 | 31 | 32 | 33 | 34 | 35 | 36 |
|---|---|---|---|---|---|---|---|
| 84 | 2.790 | 2.700 | 2.616 | 2.536 | 2.462 | 2.391 | 2.325 |
| 85 | 2.820 | 2.729 | 2.643 | 2.563 | 2.488 | 2.417 | 2.350 |
| 86 | 2.849 | 2.757 | 2.671 | 2.590 | 2.514 | 2.442 | 2.374 |
| 87 | 2.879 | 2.786 | 2.699 | 2.617 | 2.540 | 2.468 | 2.399 |
| 88 | 2.908 | 2.815 | 2.727 | 2.644 | 2.566 | 2.493 | 2.424 |
| 89 | 2.938 | 2.843 | 2.754 | 2.671 | 2.592 | 2.518 | 2.448 |
| 90 | 2.968 | 2.872 | 2.782 | 2.698 | 2.619 | 2.544 | 2.473 |
| 91 | 2.997 | 2.901 | 2.810 | 2.725 | 2.645 | 2.569 | 2.498 |
| 92 | 3.027 | 2.929 | 2.838 | 2.752 | 2.671 | 2.595 | 2.522 |
| 93 | 3.057 | 2.958 | 2.866 | 2.779 | 2.697 | 2.620 | 2.547 |
| 94 | 3.086 | 2.987 | 2.893 | 2.806 | 2.723 | 2.645 | 2.572 |
| 95 | 3.116 | 3.016 | 2.921 | 2.833 | 2.749 | 2.671 | 2.597 |
| 96 | 3.146 | 3.044 | 2.949 | 2.860 | 2.776 | 2.696 | 2.621 |
| 97 | 3.175 | 3.073 | 2.977 | 2.887 | 2.802 | 2.722 | 2.646 |
| 98 | 3.205 | 3.101 | 3.005 | 2.914 | 2.828 | 2.747 | 2.671 |
| 99 | 3.234 | 3.130 | 3.032 | 2.940 | 2.854 | 2.772 | 2.695 |
| 100 | 3.264 | 3.159 | 3.060 | 2.967 | 2.880 | 2.798 | 2.720 |
| 101 | 3.293 | 3.187 | 3.087 | 2.994 | 2.906 | 2.823 | 2.744 |
| 102 | 3.323 | 3.215 | 3.115 | 3.021 | 2.932 | 2.848 | 2.769 |
| 103 | 3.352 | 3.244 | 3.142 | 3.047 | 2.957 | 2.873 | 2.793 |
| 104 | 3.381 | 3.272 | 3.170 | 3.074 | 2.983 | 2.898 | 2.817 |
| 105 | 3.410 | 3.300 | 3.197 | 3.100 | 3.009 | 2.923 | 2.842 |
| 106 | 3.439 | 3.328 | 3.224 | 3.126 | 3.034 | 2.948 | 2.866 |
| 107 | 3.468 | 3.356 | 3.251 | 3.153 | 3.060 | 2.973 | 2.890 |
| 108 | 3.497 | 3.384 | 3.278 | 3.179 | 3.085 | 2.997 | 2.914 |
| 109 | 3.526 | 3.412 | 3.305 | 3.205 | 3.111 | 3.022 | 2.938 |
| 110 | 3.554 | 3.440 | 3.332 | 3.231 | 3.136 | 3.047 | 2.962 |
| 111 | 3.583 | 3.468 | 3.359 | 3.257 | 3.162 | 3.071 | 2.986 |
| 112 | 3.612 | 3.495 | 3.386 | 3.283 | 3.187 | 3.096 | 3.010 |
| 113 | 3.640 | 3.523 | 3.413 | 3.309 | 3.212 | 3.120 | 3.034 |
| 114 | 3.669 | 3.551 | 3.440 | 3.335 | 3.237 | 3.145 | 3.057 |
| 115 | 3.698 | 3.578 | 3.466 | 3.361 | 3.263 | 3.169 | 3.081 |
| 116 | 3.726 | 3.606 | 3.493 | 3.387 | 3.288 | 3.194 | 3.105 |
| 117 | 3.754 | 3.633 | 3.520 | 3.413 | 3.313 | 3.218 | 3.129 |
| 118 | 3.783 | 3.661 | 3.546 | 3.439 | 3.338 | 3.242 | 3.152 |
| 119 | 3.811 | 3.688 | 3.573 | 3.465 | 3.363 | 3.267 | 3.176 |
| 120 | 3.840 | 3.716 | 3.600 | 3.491 | 3.388 | 3.291 | 3.200 |

Fig. 7m

| mass[Kg] | 37 | 38 | 39 | 40 | 41 | 42 | 43 |
|---|---|---|---|---|---|---|---|
| 84 | 2.262 | 2.203 | 2.146 | 2.093 | 2.041 | 1.993 | 1.947 |
| 85 | 2.286 | 2.226 | 2.169 | 2.115 | 2.063 | 2.014 | 1.967 |
| 86 | 2.310 | 2.249 | 2.192 | 2.137 | 2.085 | 2.035 | 1.988 |
| 87 | 2.334 | 2.273 | 2.215 | 2.159 | 2.107 | 2.056 | 2.009 |
| 88 | 2.358 | 2.296 | 2.237 | 2.181 | 2.128 | 2.077 | 2.029 |
| 89 | 2.382 | 2.320 | 2.260 | 2.204 | 2.150 | 2.099 | 2.050 |
| 90 | 2.406 | 2.343 | 2.283 | 2.226 | 2.171 | 2.120 | 2.070 |
| 91 | 2.430 | 2.366 | 2.306 | 2.248 | 2.193 | 2.141 | 2.091 |
| 92 | 2.454 | 2.390 | 2.328 | 2.270 | 2.215 | 2.162 | 2.112 |
| 93 | 2.478 | 2.413 | 2.351 | 2.293 | 2.237 | 2.183 | 2.133 |
| 94 | 2.502 | 2.437 | 2.374 | 2.315 | 2.258 | 2.205 | 2.153 |
| 95 | 2.527 | 2.460 | 2.397 | 2.337 | 2.280 | 2.226 | 2.174 |
| 96 | 2.551 | 2.483 | 2.420 | 2.359 | 2.302 | 2.247 | 2.195 |
| 97 | 2.575 | 2.507 | 2.443 | 2.381 | 2.323 | 2.268 | 2.215 |
| 98 | 2.599 | 2.530 | 2.465 | 2.404 | 2.345 | 2.289 | 2.236 |
| 99 | 2.622 | 2.553 | 2.488 | 2.426 | 2.367 | 2.310 | 2.257 |
| 100 | 2.646 | 2.577 | 2.511 | 2.448 | 2.388 | 2.331 | 2.277 |
| 101 | 2.670 | 2.600 | 2.533 | 2.470 | 2.410 | 2.352 | 2.298 |
| 102 | 2.694 | 2.623 | 2.556 | 2.492 | 2.431 | 2.373 | 2.318 |
| 103 | 2.718 | 2.646 | 2.578 | 2.514 | 2.453 | 2.394 | 2.338 |
| 104 | 2.741 | 2.669 | 2.601 | 2.536 | 2.474 | 2.415 | 2.359 |
| 105 | 2.765 | 2.692 | 2.623 | 2.558 | 2.495 | 2.436 | 2.379 |
| 106 | 2.788 | 2.715 | 2.645 | 2.579 | 2.516 | 2.456 | 2.399 |
| 107 | 2.812 | 2.738 | 2.668 | 2.601 | 2.538 | 2.477 | 2.419 |
| 108 | 2.835 | 2.761 | 2.690 | 2.623 | 2.559 | 2.498 | 2.440 |
| 109 | 2.859 | 2.783 | 2.712 | 2.644 | 2.580 | 2.518 | 2.460 |
| 110 | 2.882 | 2.806 | 2.734 | 2.666 | 2.601 | 2.539 | 2.480 |
| 111 | 2.905 | 2.829 | 2.756 | 2.687 | 2.622 | 2.559 | 2.500 |
| 112 | 2.928 | 2.851 | 2.778 | 2.709 | 2.643 | 2.580 | 2.520 |
| 113 | 2.952 | 2.874 | 2.800 | 2.730 | 2.664 | 2.600 | 2.540 |
| 114 | 2.975 | 2.897 | 2.822 | 2.752 | 2.685 | 2.621 | 2.560 |
| 115 | 2.998 | 2.919 | 2.844 | 2.773 | 2.705 | 2.641 | 2.580 |
| 116 | 3.021 | 2.942 | 2.866 | 2.794 | 2.726 | 2.661 | 2.600 |
| 117 | 3.044 | 2.964 | 2.888 | 2.816 | 2.747 | 2.682 | 2.619 |
| 118 | 3.067 | 2.986 | 2.910 | 2.837 | 2.768 | 2.702 | 2.639 |
| 119 | 3.090 | 3.009 | 2.932 | 2.858 | 2.789 | 2.722 | 2.659 |
| 120 | 3.113 | 3.031 | 2.954 | 2.880 | 2.809 | 2.743 | 2.679 |

Fig. 7n

| mass[Kg] | 44 | 45 | 46 | 47 | 48 | 49 | 50 |
|---|---|---|---|---|---|---|---|
| 84 | 1.902 | 1.860 | 1.820 | 1.781 | 1.744 | 1.708 | 1.674 |
| 85 | 1.923 | 1.880 | 1.839 | 1.800 | 1.762 | 1.726 | 1.692 |
| 86 | 1.943 | 1.900 | 1.858 | 1.819 | 1.781 | 1.744 | 1.710 |
| 87 | 1.963 | 1.919 | 1.878 | 1.838 | 1.799 | 1.763 | 1.727 |
| 88 | 1.983 | 1.939 | 1.897 | 1.856 | 1.818 | 1.781 | 1.745 |
| 89 | 2.003 | 1.959 | 1.916 | 1.875 | 1.836 | 1.799 | 1.763 |
| 90 | 2.023 | 1.978 | 1.935 | 1.894 | 1.855 | 1.817 | 1.781 |
| 91 | 2.044 | 1.998 | 1.955 | 1.913 | 1.873 | 1.835 | 1.798 |
| 92 | 2.064 | 2.018 | 1.974 | 1.932 | 1.892 | 1.853 | 1.816 |
| 93 | 2.084 | 2.038 | 1.993 | 1.951 | 1.910 | 1.871 | 1.834 |
| 94 | 2.104 | 2.058 | 2.013 | 1.970 | 1.929 | 1.890 | 1.852 |
| 95 | 2.125 | 2.077 | 2.032 | 1.989 | 1.948 | 1.908 | 1.870 |
| 96 | 2.145 | 2.097 | 2.052 | 2.008 | 1.966 | 1.926 | 1.887 |
| 97 | 2.165 | 2.117 | 2.071 | 2.027 | 1.985 | 1.944 | 1.905 |
| 98 | 2.185 | 2.137 | 2.090 | 2.046 | 2.003 | 1.962 | 1.923 |
| 99 | 2.205 | 2.156 | 2.109 | 2.064 | 2.021 | 1.980 | 1.941 |
| 100 | 2.225 | 2.176 | 2.129 | 2.083 | 2.040 | 1.998 | 1.958 |
| 101 | 2.245 | 2.195 | 2.148 | 2.102 | 2.058 | 2.016 | 1.976 |
| 102 | 2.265 | 2.215 | 2.167 | 2.121 | 2.077 | 2.034 | 1.994 |
| 103 | 2.285 | 2.235 | 2.186 | 2.139 | 2.095 | 2.052 | 2.011 |
| 104 | 2.305 | 2.254 | 2.205 | 2.158 | 2.113 | 2.070 | 2.029 |
| 105 | 2.325 | 2.273 | 2.224 | 2.177 | 2.131 | 2.088 | 2.046 |
| 106 | 2.345 | 2.293 | 2.243 | 2.195 | 2.149 | 2.106 | 2.063 |
| 107 | 2.365 | 2.312 | 2.262 | 2.214 | 2.167 | 2.123 | 2.081 |
| 108 | 2.384 | 2.331 | 2.281 | 2.232 | 2.186 | 2.141 | 2.098 |
| 109 | 2.404 | 2.350 | 2.299 | 2.250 | 2.204 | 2.159 | 2.115 |
| 110 | 2.423 | 2.370 | 2.318 | 2.269 | 2.222 | 2.176 | 2.133 |
| 111 | 2.443 | 2.389 | 2.337 | 2.287 | 2.239 | 2.194 | 2.150 |
| 112 | 2.463 | 2.408 | 2.356 | 2.305 | 2.257 | 2.211 | 2.167 |
| 113 | 2.482 | 2.427 | 2.374 | 2.324 | 2.275 | 2.229 | 2.184 |
| 114 | 2.502 | 2.446 | 2.393 | 2.342 | 2.293 | 2.246 | 2.201 |
| 115 | 2.521 | 2.465 | 2.411 | 2.360 | 2.311 | 2.264 | 2.219 |
| 116 | 2.540 | 2.484 | 2.430 | 2.378 | 2.329 | 2.281 | 2.236 |
| 117 | 2.560 | 2.503 | 2.449 | 2.396 | 2.347 | 2.299 | 2.253 |
| 118 | 2.579 | 2.522 | 2.467 | 2.415 | 2.364 | 2.316 | 2.270 |
| 119 | 2.599 | 2.541 | 2.486 | 2.433 | 2.382 | 2.333 | 2.287 |
| 120 | 2.618 | 2.560 | 2.504 | 2.451 | 2.400 | 2.351 | 2.304 |

Fig. 7o

| mass[Kg] | 51 | 52 | 53 | 54 | 55 | 56 | 57 |
|---|---|---|---|---|---|---|---|
| 84 | 1.641 | 1.610 | 1.579 | 1.550 | 1.522 | 1.495 | 1.468 |
| 85 | 1.659 | 1.627 | 1.596 | 1.566 | 1.538 | 1.511 | 1.484 |
| 86 | 1.676 | 1.644 | 1.613 | 1.583 | 1.554 | 1.526 | 1.500 |
| 87 | 1.693 | 1.661 | 1.630 | 1.599 | 1.570 | 1.542 | 1.515 |
| 88 | 1.711 | 1.678 | 1.646 | 1.616 | 1.586 | 1.558 | 1.531 |
| 89 | 1.728 | 1.695 | 1.663 | 1.632 | 1.603 | 1.574 | 1.546 |
| 90 | 1.746 | 1.712 | 1.680 | 1.649 | 1.619 | 1.590 | 1.562 |
| 91 | 1.763 | 1.729 | 1.697 | 1.665 | 1.635 | 1.606 | 1.578 |
| 92 | 1.781 | 1.746 | 1.713 | 1.682 | 1.651 | 1.622 | 1.593 |
| 93 | 1.798 | 1.763 | 1.730 | 1.698 | 1.667 | 1.638 | 1.609 |
| 94 | 1.815 | 1.781 | 1.747 | 1.715 | 1.683 | 1.653 | 1.624 |
| 95 | 1.833 | 1.798 | 1.764 | 1.731 | 1.700 | 1.669 | 1.640 |
| 96 | 1.850 | 1.815 | 1.781 | 1.748 | 1.716 | 1.685 | 1.656 |
| 97 | 1.868 | 1.832 | 1.797 | 1.764 | 1.732 | 1.701 | 1.671 |
| 98 | 1.885 | 1.849 | 1.814 | 1.780 | 1.748 | 1.717 | 1.687 |
| 99 | 1.903 | 1.866 | 1.831 | 1.797 | 1.764 | 1.733 | 1.702 |
| 100 | 1.920 | 1.883 | 1.847 | 1.813 | 1.780 | 1.748 | 1.718 |
| 101 | 1.937 | 1.900 | 1.864 | 1.830 | 1.796 | 1.764 | 1.733 |
| 102 | 1.954 | 1.917 | 1.881 | 1.846 | 1.812 | 1.780 | 1.749 |
| 103 | 1.972 | 1.934 | 1.897 | 1.862 | 1.828 | 1.796 | 1.764 |
| 104 | 1.989 | 1.951 | 1.914 | 1.878 | 1.844 | 1.811 | 1.779 |
| 105 | 2.006 | 1.967 | 1.930 | 1.894 | 1.860 | 1.827 | 1.795 |
| 106 | 2.023 | 1.984 | 1.947 | 1.911 | 1.876 | 1.842 | 1.810 |
| 107 | 2.040 | 2.001 | 1.963 | 1.927 | 1.892 | 1.858 | 1.825 |
| 108 | 2.057 | 2.017 | 1.979 | 1.943 | 1.907 | 1.873 | 1.840 |
| 109 | 2.074 | 2.034 | 1.996 | 1.959 | 1.923 | 1.889 | 1.856 |
| 110 | 2.091 | 2.051 | 2.012 | 1.975 | 1.939 | 1.904 | 1.871 |
| 111 | 2.108 | 2.067 | 2.028 | 1.991 | 1.954 | 1.920 | 1.886 |
| 112 | 2.125 | 2.084 | 2.044 | 2.007 | 1.970 | 1.935 | 1.901 |
| 113 | 2.141 | 2.100 | 2.061 | 2.022 | 1.986 | 1.950 | 1.916 |
| 114 | 2.158 | 2.117 | 2.077 | 2.038 | 2.001 | 1.966 | 1.931 |
| 115 | 2.175 | 2.133 | 2.093 | 2.054 | 2.017 | 1.981 | 1.946 |
| 116 | 2.192 | 2.150 | 2.109 | 2.070 | 2.032 | 1.996 | 1.961 |
| 117 | 2.208 | 2.166 | 2.125 | 2.086 | 2.048 | 2.011 | 1.976 |
| 118 | 2.225 | 2.182 | 2.141 | 2.102 | 2.063 | 2.027 | 1.991 |
| 119 | 2.242 | 2.199 | 2.157 | 2.117 | 2.079 | 2.042 | 2.006 |
| 120 | 2.259 | 2.215 | 2.173 | 2.133 | 2.094 | 2.057 | 2.021 |

Fig. 7p

| mass[Kg] | 65 | 66 | 67 | 68 | 69 | 70 | 71 |
|---|---|---|---|---|---|---|---|
| 84 | 1.288 | 1.268 | 1.249 | 1.231 | 1.213 | 1.196 | 1.179 |
| 85 | 1.301 | 1.282 | 1.263 | 1.244 | 1.226 | 1.208 | 1.191 |
| 86 | 1.315 | 1.295 | 1.276 | 1.257 | 1.239 | 1.221 | 1.204 |
| 87 | 1.329 | 1.309 | 1.289 | 1.270 | 1.252 | 1.234 | 1.216 |
| 88 | 1.342 | 1.322 | 1.302 | 1.283 | 1.265 | 1.246 | 1.229 |
| 89 | 1.356 | 1.335 | 1.316 | 1.296 | 1.277 | 1.259 | 1.241 |
| 90 | 1.370 | 1.349 | 1.329 | 1.309 | 1.290 | 1.272 | 1.254 |
| 91 | 1.383 | 1.362 | 1.342 | 1.322 | 1.303 | 1.285 | 1.266 |
| 92 | 1.397 | 1.376 | 1.355 | 1.335 | 1.316 | 1.297 | 1.279 |
| 93 | 1.411 | 1.389 | 1.369 | 1.349 | 1.329 | 1.310 | 1.292 |
| 94 | 1.424 | 1.403 | 1.382 | 1.362 | 1.342 | 1.323 | 1.304 |
| 95 | 1.438 | 1.416 | 1.395 | 1.375 | 1.355 | 1.335 | 1.317 |
| 96 | 1.452 | 1.430 | 1.409 | 1.388 | 1.368 | 1.348 | 1.329 |
| 97 | 1.466 | 1.443 | 1.422 | 1.401 | 1.381 | 1.361 | 1.342 |
| 98 | 1.479 | 1.457 | 1.435 | 1.414 | 1.393 | 1.374 | 1.354 |
| 99 | 1.493 | 1.470 | 1.448 | 1.427 | 1.406 | 1.386 | 1.367 |
| 100 | 1.506 | 1.484 | 1.461 | 1.440 | 1.419 | 1.399 | 1.379 |
| 101 | 1.520 | 1.497 | 1.475 | 1.453 | 1.432 | 1.411 | 1.392 |
| 102 | 1.533 | 1.510 | 1.488 | 1.466 | 1.445 | 1.424 | 1.404 |
| 103 | 1.547 | 1.524 | 1.501 | 1.479 | 1.457 | 1.436 | 1.416 |
| 104 | 1.560 | 1.537 | 1.514 | 1.492 | 1.470 | 1.449 | 1.429 |
| 105 | 1.574 | 1.550 | 1.527 | 1.504 | 1.483 | 1.461 | 1.441 |
| 106 | 1.587 | 1.563 | 1.540 | 1.517 | 1.495 | 1.474 | 1.453 |
| 107 | 1.601 | 1.576 | 1.553 | 1.530 | 1.508 | 1.486 | 1.465 |
| 108 | 1.614 | 1.589 | 1.566 | 1.543 | 1.520 | 1.499 | 1.478 |
| 109 | 1.627 | 1.603 | 1.579 | 1.555 | 1.533 | 1.511 | 1.490 |
| 110 | 1.640 | 1.616 | 1.592 | 1.568 | 1.545 | 1.523 | 1.502 |
| 111 | 1.654 | 1.629 | 1.604 | 1.581 | 1.558 | 1.536 | 1.514 |
| 112 | 1.667 | 1.642 | 1.617 | 1.593 | 1.570 | 1.548 | 1.526 |
| 113 | 1.680 | 1.655 | 1.630 | 1.606 | 1.583 | 1.560 | 1.538 |
| 114 | 1.693 | 1.668 | 1.643 | 1.619 | 1.595 | 1.572 | 1.550 |
| 115 | 1.707 | 1.681 | 1.656 | 1.631 | 1.608 | 1.585 | 1.562 |
| 116 | 1.720 | 1.694 | 1.668 | 1.644 | 1.620 | 1.597 | 1.574 |
| 117 | 1.733 | 1.707 | 1.681 | 1.656 | 1.632 | 1.609 | 1.586 |
| 118 | 1.746 | 1.719 | 1.694 | 1.669 | 1.645 | 1.621 | 1.598 |
| 119 | 1.759 | 1.732 | 1.707 | 1.681 | 1.657 | 1.633 | 1.610 |
| 120 | 1.772 | 1.745 | 1.719 | 1.694 | 1.669 | 1.646 | 1.622 |

Fig. 7q

| mass[Kg] | 58 | 59 | 60 | 61 | 62 | 63 | 64 |
|---|---|---|---|---|---|---|---|
| 84 | 1.443 | 1.419 | 1.395 | 1.372 | 1.350 | 1.329 | 1.308 |
| 85 | 1.458 | 1.434 | 1.410 | 1.387 | 1.364 | 1.343 | 1.322 |
| 86 | 1.474 | 1.449 | 1.425 | 1.401 | 1.379 | 1.357 | 1.336 |
| 87 | 1.489 | 1.464 | 1.439 | 1.416 | 1.393 | 1.371 | 1.349 |
| 88 | 1.504 | 1.479 | 1.454 | 1.430 | 1.407 | 1.385 | 1.363 |
| 89 | 1.520 | 1.494 | 1.469 | 1.445 | 1.422 | 1.399 | 1.377 |
| 90 | 1.535 | 1.509 | 1.484 | 1.460 | 1.436 | 1.413 | 1.391 |
| 91 | 1.550 | 1.524 | 1.499 | 1.474 | 1.450 | 1.427 | 1.405 |
| 92 | 1.566 | 1.539 | 1.513 | 1.489 | 1.465 | 1.441 | 1.419 |
| 93 | 1.581 | 1.554 | 1.528 | 1.503 | 1.479 | 1.456 | 1.433 |
| 94 | 1.596 | 1.569 | 1.543 | 1.518 | 1.493 | 1.470 | 1.447 |
| 95 | 1.612 | 1.584 | 1.558 | 1.532 | 1.508 | 1.484 | 1.461 |
| 96 | 1.627 | 1.599 | 1.573 | 1.547 | 1.522 | 1.498 | 1.475 |
| 97 | 1.642 | 1.615 | 1.588 | 1.562 | 1.536 | 1.512 | 1.488 |
| 98 | 1.658 | 1.630 | 1.602 | 1.576 | 1.551 | 1.526 | 1.502 |
| 99 | 1.673 | 1.645 | 1.617 | 1.591 | 1.565 | 1.540 | 1.516 |
| 100 | 1.688 | 1.660 | 1.632 | 1.605 | 1.579 | 1.554 | 1.530 |
| 101 | 1.703 | 1.675 | 1.647 | 1.620 | 1.594 | 1.568 | 1.544 |
| 102 | 1.719 | 1.689 | 1.661 | 1.634 | 1.608 | 1.582 | 1.557 |
| 103 | 1.734 | 1.704 | 1.676 | 1.648 | 1.622 | 1.596 | 1.571 |
| 104 | 1.749 | 1.719 | 1.690 | 1.663 | 1.636 | 1.610 | 1.585 |
| 105 | 1.764 | 1.734 | 1.705 | 1.677 | 1.650 | 1.624 | 1.598 |
| 106 | 1.779 | 1.749 | 1.720 | 1.691 | 1.664 | 1.638 | 1.612 |
| 107 | 1.794 | 1.763 | 1.734 | 1.706 | 1.678 | 1.651 | 1.626 |
| 108 | 1.809 | 1.778 | 1.748 | 1.720 | 1.692 | 1.665 | 1.639 |
| 109 | 1.824 | 1.793 | 1.763 | 1.734 | 1.706 | 1.679 | 1.653 |
| 110 | 1.838 | 1.807 | 1.777 | 1.748 | 1.720 | 1.693 | 1.666 |
| 111 | 1.853 | 1.822 | 1.792 | 1.762 | 1.734 | 1.706 | 1.680 |
| 112 | 1.868 | 1.837 | 1.806 | 1.776 | 1.748 | 1.720 | 1.693 |
| 113 | 1.883 | 1.851 | 1.820 | 1.790 | 1.761 | 1.734 | 1.706 |
| 114 | 1.898 | 1.866 | 1.834 | 1.804 | 1.775 | 1.747 | 1.720 |
| 115 | 1.913 | 1.880 | 1.849 | 1.818 | 1.789 | 1.761 | 1.733 |
| 116 | 1.927 | 1.895 | 1.863 | 1.832 | 1.803 | 1.774 | 1.747 |
| 117 | 1.942 | 1.909 | 1.877 | 1.846 | 1.817 | 1.788 | 1.760 |
| 118 | 1.957 | 1.923 | 1.891 | 1.860 | 1.830 | 1.801 | 1.773 |
| 119 | 1.971 | 1.938 | 1.906 | 1.874 | 1.844 | 1.815 | 1.787 |
| 120 | 1.986 | 1.952 | 1.920 | 1.888 | 1.858 | 1.828 | 1.800 |

Fig. 7r

| mass[Kg] | 72 | 73 | 74 | 75 | 76 | 77 | 78 |
|---|---|---|---|---|---|---|---|
| 84 | 1.163 | 1.147 | 1.131 | 1.116 | 1.101 | 1.087 | 1.073 |
| 85 | 1.175 | 1.159 | 1.143 | 1.128 | 1.113 | 1.099 | 1.084 |
| 86 | 1.187 | 1.171 | 1.155 | 1.140 | 1.125 | 1.110 | 1.096 |
| 87 | 1.200 | 1.183 | 1.167 | 1.152 | 1.136 | 1.122 | 1.107 |
| 88 | 1.212 | 1.195 | 1.179 | 1.163 | 1.148 | 1.133 | 1.119 |
| 89 | 1.224 | 1.207 | 1.191 | 1.175 | 1.160 | 1.145 | 1.130 |
| 90 | 1.237 | 1.220 | 1.203 | 1.187 | 1.171 | 1.156 | 1.141 |
| 91 | 1.249 | 1.232 | 1.215 | 1.199 | 1.183 | 1.168 | 1.153 |
| 92 | 1.261 | 1.244 | 1.227 | 1.211 | 1.195 | 1.179 | 1.164 |
| 93 | 1.274 | 1.256 | 1.239 | 1.223 | 1.207 | 1.191 | 1.176 |
| 94 | 1.286 | 1.268 | 1.251 | 1.235 | 1.218 | 1.202 | 1.187 |
| 95 | 1.298 | 1.281 | 1.263 | 1.246 | 1.230 | 1.214 | 1.198 |
| 96 | 1.311 | 1.293 | 1.275 | 1.258 | 1.242 | 1.226 | 1.210 |
| 97 | 1.323 | 1.305 | 1.287 | 1.270 | 1.253 | 1.237 | 1.221 |
| 98 | 1.335 | 1.317 | 1.299 | 1.282 | 1.265 | 1.249 | 1.233 |
| 99 | 1.348 | 1.329 | 1.311 | 1.294 | 1.277 | 1.260 | 1.244 |
| 100 | 1.360 | 1.341 | 1.323 | 1.306 | 1.288 | 1.272 | 1.255 |
| 101 | 1.372 | 1.353 | 1.335 | 1.317 | 1.300 | 1.283 | 1.267 |
| 102 | 1.384 | 1.365 | 1.347 | 1.329 | 1.312 | 1.295 | 1.278 |
| 103 | 1.397 | 1.377 | 1.359 | 1.341 | 1.323 | 1.306 | 1.289 |
| 104 | 1.409 | 1.389 | 1.371 | 1.352 | 1.335 | 1.317 | 1.300 |
| 105 | 1.421 | 1.401 | 1.382 | 1.364 | 1.346 | 1.329 | 1.312 |
| 106 | 1.433 | 1.413 | 1.394 | 1.376 | 1.358 | 1.340 | 1.323 |
| 107 | 1.445 | 1.425 | 1.406 | 1.387 | 1.369 | 1.351 | 1.334 |
| 108 | 1.457 | 1.437 | 1.418 | 1.399 | 1.380 | 1.362 | 1.345 |
| 109 | 1.469 | 1.449 | 1.429 | 1.410 | 1.392 | 1.374 | 1.356 |
| 110 | 1.481 | 1.461 | 1.441 | 1.422 | 1.403 | 1.385 | 1.367 |
| 111 | 1.493 | 1.473 | 1.453 | 1.433 | 1.414 | 1.396 | 1.378 |
| 112 | 1.505 | 1.484 | 1.464 | 1.445 | 1.426 | 1.407 | 1.389 |
| 113 | 1.517 | 1.496 | 1.476 | 1.456 | 1.437 | 1.418 | 1.400 |
| 114 | 1.529 | 1.508 | 1.487 | 1.468 | 1.448 | 1.429 | 1.411 |
| 115 | 1.541 | 1.520 | 1.499 | 1.479 | 1.460 | 1.441 | 1.422 |
| 116 | 1.552 | 1.531 | 1.511 | 1.490 | 1.471 | 1.452 | 1.433 |
| 117 | 1.564 | 1.543 | 1.522 | 1.502 | 1.482 | 1.463 | 1.444 |
| 118 | 1.576 | 1.555 | 1.534 | 1.513 | 1.493 | 1.474 | 1.455 |
| 119 | 1.588 | 1.566 | 1.545 | 1.525 | 1.504 | 1.485 | 1.466 |
| 120 | 1.600 | 1.578 | 1.557 | 1.536 | 1.516 | 1.496 | 1.477 |

Fig. 7s

| mass[Kg] | 79 | 80 | 81 | 82 | 83 | 84 | 85 |
|---|---|---|---|---|---|---|---|
| 84 | 1.060 | 1.046 | 1.033 | 1.021 | 1.008 | 0.996 | 0.985 |
| 85 | 1.071 | 1.057 | 1.044 | 1.032 | 1.019 | 1.007 | 0.995 |
| 86 | 1.082 | 1.068 | 1.055 | 1.042 | 1.030 | 1.018 | 1.006 |
| 87 | 1.093 | 1.080 | 1.066 | 1.053 | 1.041 | 1.028 | 1.016 |
| 88 | 1.104 | 1.091 | 1.077 | 1.064 | 1.051 | 1.039 | 1.027 |
| 89 | 1.116 | 1.102 | 1.088 | 1.075 | 1.062 | 1.049 | 1.037 |
| 90 | 1.127 | 1.113 | 1.099 | 1.086 | 1.073 | 1.060 | 1.047 |
| 91 | 1.138 | 1.124 | 1.110 | 1.097 | 1.083 | 1.070 | 1.058 |
| 92 | 1.149 | 1.135 | 1.121 | 1.107 | 1.094 | 1.081 | 1.068 |
| 93 | 1.161 | 1.146 | 1.132 | 1.118 | 1.105 | 1.092 | 1.079 |
| 94 | 1.172 | 1.157 | 1.143 | 1.129 | 1.116 | 1.102 | 1.089 |
| 95 | 1.183 | 1.169 | 1.154 | 1.140 | 1.126 | 1.113 | 1.100 |
| 96 | 1.195 | 1.180 | 1.165 | 1.151 | 1.137 | 1.123 | 1.110 |
| 97 | 1.206 | 1.191 | 1.176 | 1.162 | 1.148 | 1.134 | 1.121 |
| 98 | 1.217 | 1.202 | 1.187 | 1.173 | 1.158 | 1.145 | 1.131 |
| 99 | 1.228 | 1.213 | 1.198 | 1.183 | 1.169 | 1.155 | 1.142 |
| 100 | 1.239 | 1.224 | 1.209 | 1.194 | 1.180 | 1.166 | 1.152 |
| 101 | 1.251 | 1.235 | 1.220 | 1.205 | 1.190 | 1.176 | 1.162 |
| 102 | 1.262 | 1.246 | 1.231 | 1.216 | 1.201 | 1.187 | 1.173 |
| 103 | 1.273 | 1.257 | 1.241 | 1.226 | 1.211 | 1.197 | 1.183 |
| 104 | 1.284 | 1.268 | 1.252 | 1.237 | 1.222 | 1.207 | 1.193 |
| 105 | 1.295 | 1.279 | 1.263 | 1.248 | 1.233 | 1.218 | 1.204 |
| 106 | 1.306 | 1.290 | 1.274 | 1.258 | 1.243 | 1.228 | 1.214 |
| 107 | 1.317 | 1.300 | 1.284 | 1.269 | 1.253 | 1.239 | 1.224 |
| 108 | 1.328 | 1.311 | 1.295 | 1.279 | 1.264 | 1.249 | 1.234 |
| 109 | 1.339 | 1.322 | 1.306 | 1.290 | 1.274 | 1.259 | 1.244 |
| 110 | 1.350 | 1.333 | 1.316 | 1.300 | 1.285 | 1.269 | 1.254 |
| 111 | 1.361 | 1.344 | 1.327 | 1.311 | 1.295 | 1.280 | 1.265 |
| 112 | 1.372 | 1.354 | 1.338 | 1.321 | 1.305 | 1.290 | 1.275 |
| 113 | 1.382 | 1.365 | 1.348 | 1.332 | 1.316 | 1.300 | 1.285 |
| 114 | 1.393 | 1.376 | 1.359 | 1.342 | 1.326 | 1.310 | 1.295 |
| 115 | 1.404 | 1.387 | 1.369 | 1.353 | 1.336 | 1.321 | 1.305 |
| 116 | 1.415 | 1.397 | 1.380 | 1.363 | 1.347 | 1.331 | 1.315 |
| 117 | 1.426 | 1.408 | 1.391 | 1.374 | 1.357 | 1.341 | 1.325 |
| 118 | 1.437 | 1.419 | 1.401 | 1.384 | 1.367 | 1.351 | 1.335 |
| 119 | 1.447 | 1.429 | 1.412 | 1.394 | 1.378 | 1.361 | 1.345 |
| 120 | 1.458 | 1.440 | 1.422 | 1.405 | 1.388 | 1.371 | 1.355 |

Fig. 7t

| mass[Kg] | 86 | 87 | 88 | 89 | 90 | 91 | 92 |
|---|---|---|---|---|---|---|---|
| 84 | 0.973 | 0.962 | 0.951 | 0.940 | 0.930 | 0.920 | 0.910 |
| 85 | 0.984 | 0.972 | 0.961 | 0.950 | 0.940 | 0.930 | 0.919 |
| 86 | 0.994 | 0.983 | 0.971 | 0.960 | 0.950 | 0.939 | 0.929 |
| 87 | 1.004 | 0.993 | 0.981 | 0.970 | 0.960 | 0.949 | 0.939 |
| 88 | 1.015 | 1.003 | 0.992 | 0.980 | 0.969 | 0.959 | 0.948 |
| 89 | 1.025 | 1.013 | 1.002 | 0.990 | 0.979 | 0.969 | 0.958 |
| 90 | 1.035 | 1.023 | 1.012 | 1.000 | 0.989 | 0.978 | 0.968 |
| 91 | 1.046 | 1.034 | 1.022 | 1.010 | 0.999 | 0.988 | 0.977 |
| 92 | 1.056 | 1.044 | 1.032 | 1.020 | 1.009 | 0.998 | 0.987 |
| 93 | 1.066 | 1.054 | 1.042 | 1.030 | 1.019 | 1.008 | 0.997 |
| 94 | 1.077 | 1.064 | 1.052 | 1.040 | 1.029 | 1.017 | 1.006 |
| 95 | 1.087 | 1.074 | 1.062 | 1.050 | 1.039 | 1.027 | 1.016 |
| 96 | 1.097 | 1.085 | 1.072 | 1.060 | 1.049 | 1.037 | 1.026 |
| 97 | 1.108 | 1.095 | 1.082 | 1.070 | 1.058 | 1.047 | 1.035 |
| 98 | 1.118 | 1.105 | 1.093 | 1.080 | 1.068 | 1.057 | 1.045 |
| 99 | 1.128 | 1.115 | 1.103 | 1.090 | 1.078 | 1.066 | 1.055 |
| 100 | 1.139 | 1.125 | 1.113 | 1.100 | 1.088 | 1.076 | 1.064 |
| 101 | 1.149 | 1.136 | 1.123 | 1.110 | 1.098 | 1.086 | 1.074 |
| 102 | 1.159 | 1.146 | 1.133 | 1.120 | 1.108 | 1.095 | 1.083 |
| 103 | 1.169 | 1.156 | 1.143 | 1.130 | 1.117 | 1.105 | 1.093 |
| 104 | 1.179 | 1.166 | 1.153 | 1.140 | 1.127 | 1.115 | 1.102 |
| 105 | 1.190 | 1.176 | 1.163 | 1.149 | 1.137 | 1.124 | 1.112 |
| 106 | 1.200 | 1.186 | 1.172 | 1.159 | 1.146 | 1.134 | 1.121 |
| 107 | 1.210 | 1.196 | 1.182 | 1.169 | 1.156 | 1.143 | 1.131 |
| 108 | 1.220 | 1.206 | 1.192 | 1.179 | 1.166 | 1.153 | 1.140 |
| 109 | 1.230 | 1.216 | 1.202 | 1.188 | 1.175 | 1.162 | 1.150 |
| 110 | 1.240 | 1.226 | 1.212 | 1.198 | 1.185 | 1.172 | 1.159 |
| 111 | 1.250 | 1.236 | 1.222 | 1.208 | 1.194 | 1.181 | 1.168 |
| 112 | 1.260 | 1.245 | 1.231 | 1.217 | 1.204 | 1.191 | 1.178 |
| 113 | 1.270 | 1.255 | 1.241 | 1.227 | 1.213 | 1.200 | 1.187 |
| 114 | 1.280 | 1.265 | 1.251 | 1.237 | 1.223 | 1.210 | 1.196 |
| 115 | 1.290 | 1.275 | 1.261 | 1.246 | 1.233 | 1.219 | 1.206 |
| 116 | 1.300 | 1.285 | 1.270 | 1.256 | 1.242 | 1.228 | 1.215 |
| 117 | 1.310 | 1.295 | 1.280 | 1.266 | 1.251 | 1.238 | 1.224 |
| 118 | 1.320 | 1.304 | 1.290 | 1.275 | 1.261 | 1.247 | 1.234 |
| 119 | 1.330 | 1.314 | 1.299 | 1.285 | 1.270 | 1.256 | 1.243 |
| 120 | 1.339 | 1.324 | 1.309 | 1.294 | 1.280 | 1.266 | 1.252 |

Fig. 7u

| mass[Kg] | 93 | 94 | 95 | 96 | 97 |
|---|---|---|---|---|---|
| 84 | 0.900 | 0.890 | 0.881 | 0.872 | 0.863 |
| 85 | 0.910 | 0.900 | 0.890 | 0.881 | 0.872 |
| 86 | 0.919 | 0.909 | 0.900 | 0.890 | 0.881 |
| 87 | 0.929 | 0.919 | 0.909 | 0.900 | 0.890 |
| 88 | 0.938 | 0.928 | 0.918 | 0.909 | 0.900 |
| 89 | 0.948 | 0.938 | 0.928 | 0.918 | 0.909 |
| 90 | 0.957 | 0.947 | 0.937 | 0.927 | 0.918 |
| 91 | 0.967 | 0.957 | 0.947 | 0.937 | 0.927 |
| 92 | 0.976 | 0.966 | 0.956 | 0.946 | 0.936 |
| 93 | 0.986 | 0.976 | 0.965 | 0.955 | 0.945 |
| 94 | 0.996 | 0.985 | 0.975 | 0.964 | 0.955 |
| 95 | 1.005 | 0.994 | 0.984 | 0.974 | 0.964 |
| 96 | 1.015 | 1.004 | 0.993 | 0.983 | 0.973 |
| 97 | 1.024 | 1.013 | 1.003 | 0.992 | 0.982 |
| 98 | 1.034 | 1.023 | 1.012 | 1.002 | 0.991 |
| 99 | 1.043 | 1.032 | 1.021 | 1.011 | 1.000 |
| 100 | 1.053 | 1.042 | 1.031 | 1.020 | 1.009 |
| 101 | 1.062 | 1.051 | 1.040 | 1.029 | 1.019 |
| 102 | 1.072 | 1.060 | 1.049 | 1.038 | 1.028 |
| 103 | 1.081 | 1.070 | 1.058 | 1.047 | 1.037 |
| 104 | 1.091 | 1.079 | 1.068 | 1.057 | 1.046 |
| 105 | 1.100 | 1.088 | 1.077 | 1.066 | 1.055 |
| 106 | 1.109 | 1.098 | 1.086 | 1.075 | 1.064 |
| 107 | 1.119 | 1.107 | 1.095 | 1.084 | 1.073 |
| 108 | 1.128 | 1.116 | 1.104 | 1.093 | 1.081 |
| 109 | 1.137 | 1.125 | 1.113 | 1.102 | 1.090 |
| 110 | 1.147 | 1.134 | 1.122 | 1.111 | 1.099 |
| 111 | 1.156 | 1.144 | 1.132 | 1.120 | 1.108 |
| 112 | 1.165 | 1.153 | 1.141 | 1.129 | 1.117 |
| 113 | 1.174 | 1.162 | 1.150 | 1.138 | 1.126 |
| 114 | 1.184 | 1.171 | 1.159 | 1.147 | 1.135 |
| 115 | 1.193 | 1.180 | 1.168 | 1.155 | 1.144 |
| 116 | 1.202 | 1.189 | 1.177 | 1.164 | 1.152 |
| 117 | 1.211 | 1.198 | 1.186 | 1.173 | 1.161 |
| 118 | 1.220 | 1.207 | 1.195 | 1.182 | 1.170 |
| 119 | 1.229 | 1.216 | 1.204 | 1.191 | 1.179 |
| 120 | 1.239 | 1.225 | 1.213 | 1.200 | 1.188 |

Fig. 7v

| mass[Kg] | 98 | 99 | 100 |
|---|---|---|---|
| 84 | 0.854 | 0.845 | 0.837 |
| 85 | 0.863 | 0.854 | 0.846 |
| 86 | 0.872 | 0.863 | 0.855 |
| 87 | 0.881 | 0.872 | 0.864 |
| 88 | 0.890 | 0.881 | 0.873 |
| 89 | 0.899 | 0.890 | 0.881 |
| 90 | 0.908 | 0.899 | 0.890 |
| 91 | 0.918 | 0.908 | 0.899 |
| 92 | 0.927 | 0.917 | 0.908 |
| 93 | 0.936 | 0.926 | 0.917 |
| 94 | 0.945 | 0.935 | 0.926 |
| 95 | 0.954 | 0.944 | 0.935 |
| 96 | 0.963 | 0.953 | 0.944 |
| 97 | 0.972 | 0.962 | 0.953 |
| 98 | 0.981 | 0.971 | 0.961 |
| 99 | 0.990 | 0.980 | 0.970 |
| 100 | 0.999 | 0.989 | 0.979 |
| 101 | 1.008 | 0.998 | 0.988 |
| 102 | 1.017 | 1.007 | 0.997 |
| 103 | 1.026 | 1.016 | 1.006 |
| 104 | 1.035 | 1.025 | 1.014 |
| 105 | 1.044 | 1.033 | 1.023 |
| 106 | 1.053 | 1.042 | 1.032 |
| 107 | 1.062 | 1.051 | 1.040 |
| 108 | 1.070 | 1.060 | 1.049 |
| 109 | 1.079 | 1.068 | 1.058 |
| 110 | 1.088 | 1.077 | 1.066 |
| 111 | 1.097 | 1.086 | 1.075 |
| 112 | 1.106 | 1.094 | 1.084 |
| 113 | 1.114 | 1.103 | 1.092 |
| 114 | 1.123 | 1.112 | 1.101 |
| 115 | 1.132 | 1.120 | 1.109 |
| 116 | 1.141 | 1.129 | 1.118 |
| 117 | 1.149 | 1.138 | 1.126 |
| 118 | 1.158 | 1.146 | 1.135 |
| 119 | 1.167 | 1.155 | 1.143 |
| 120 | 1.175 | 1.164 | 1.152 | toxicity_noBMT.txt

| pt num | mCi | TB-kg | TB-dose | Blood-dose | marrow-dose | LBM | tox-grade | mCiperKG | mCipermsqm | CiperLBMTBLBMdose |  |
|---|---|---|---|---|---|---|---|---|---|---|---|
| 1 | 66.0 | 72.8 | 25.0 | 126 | 51 | 74.606 | 1 | 0.907 | 34.8 | 0.885 | 25.8 |
| 2 | 45.1 | 77.2 | 25.0 | 141 | 55 | 69.2 | 0 | 0.584 | 23.7 | 0.652 | 28.2 |
| 4 | 57.0 | 80.8 | 25.0 | 166 | 64 | 66.974 | 1 | 0.705 | 29.6 | 0.851 | 31.4 |
| 5 | 38.0 | 74.9 | 35.0 | 186 | 76 | 74.924 | 1 | 0.507 | 19.8 | 0.507 | 33.6 |
| 6 | 40.0 | 81.3 | 35.0 | 257 | 99 | 81.39 | 1 | 0.492 | 19.6 | 0.491 | 34.6 |
| 7 | 41.0 | 82.6 | 35.0 | 126 | 60 | 81.602 | 0 | 0.496 | 20.0 | 0.502 | 37.6 |
| 8 | 39.8 | 84.2 | 35.0 | 146 | 67 | 71.002 | 2 | 0.473 | 20.0 | 0.561 | 42.4 |
| 9 | 43.5 | 66.0 | 45.0 | 269 | 104 | 54.042 | 0 | 0.659 | 26.0 | 0.805 | 55.9 |
| 10 | 61.5 | 90.0 | 45.0 | 291 | 118 | 77.68 | 0 | 0.683 | 29.3 | 0.792 | 52.2 |
| 13 | 40.5 | 60.5 | 45.0 | 293 | 112 | 55.965 | 0 | 0.669 | 24.5 | 0.724 | 50.7 |
| 14 | 68.3 | 83.3 | 55.0 | 305 | 127 | 73.334 | 0 | 0.820 | 34.2 | 0.931 | 64.3 |
| 15 | 44.1 | 54.4 | 55.0 | 265 | 105 | 58.24 | 3 | 0.811 | 27.6 | 0.757 | 53.7 |
| 16 | 70.9 | 93.4 | 55.0 | 381 | 153 | 73.97 | 2 | 0.759 | 33.7 | 0.958 | 70.1 |
| 19 | 68.5 | 82.3 | 65.0 | 370 | 158 | 56.602 | 1 | 0.832 | 36.2 | 1.210 | 92.2 |
| 24 | 106.7 | 83.1 | 75.0 | 340 | 148 | 83.934 | 0 | 1.284 | 51.4 | 1.271 | 71.4 |
| 27 | 97.9 | 73.0 | 85.0 | 443 | 187 | 57.785 | 0 | 1.341 | 54.2 | 1.694 | 108.5 |
| 28 | 95.6 | 86.4 | 85.0 | 228 | 121 | 79.164 | 4 | 1.106 | 46.1 | 1.208 | 97.5 |
| 29 | 161.0 | 136.0 | 85.0 | 474 | 241 | 70.343 | 4 | 1.184 | 64.5 | 2.289 | 164.4 |
| 31 | 107.5 | 91.8 | 75.0 | 232 | 120 | 70.578 | 3 | 1.171 | 52.2 | 1.523 | 108.4 |
| 32 | 56.8 | 48.0 | 75.0 | 457 | 169 | 47.32 | 0 | 1.183 | 39.6 | 1.200 | 80.0 |
| 34 | 102.5 | 88.6 | 75.0 | 517 | 205 | 78.74 | 2 | 1.157 | 49.0 | 1.302 | 82.6 |

Fig. 9

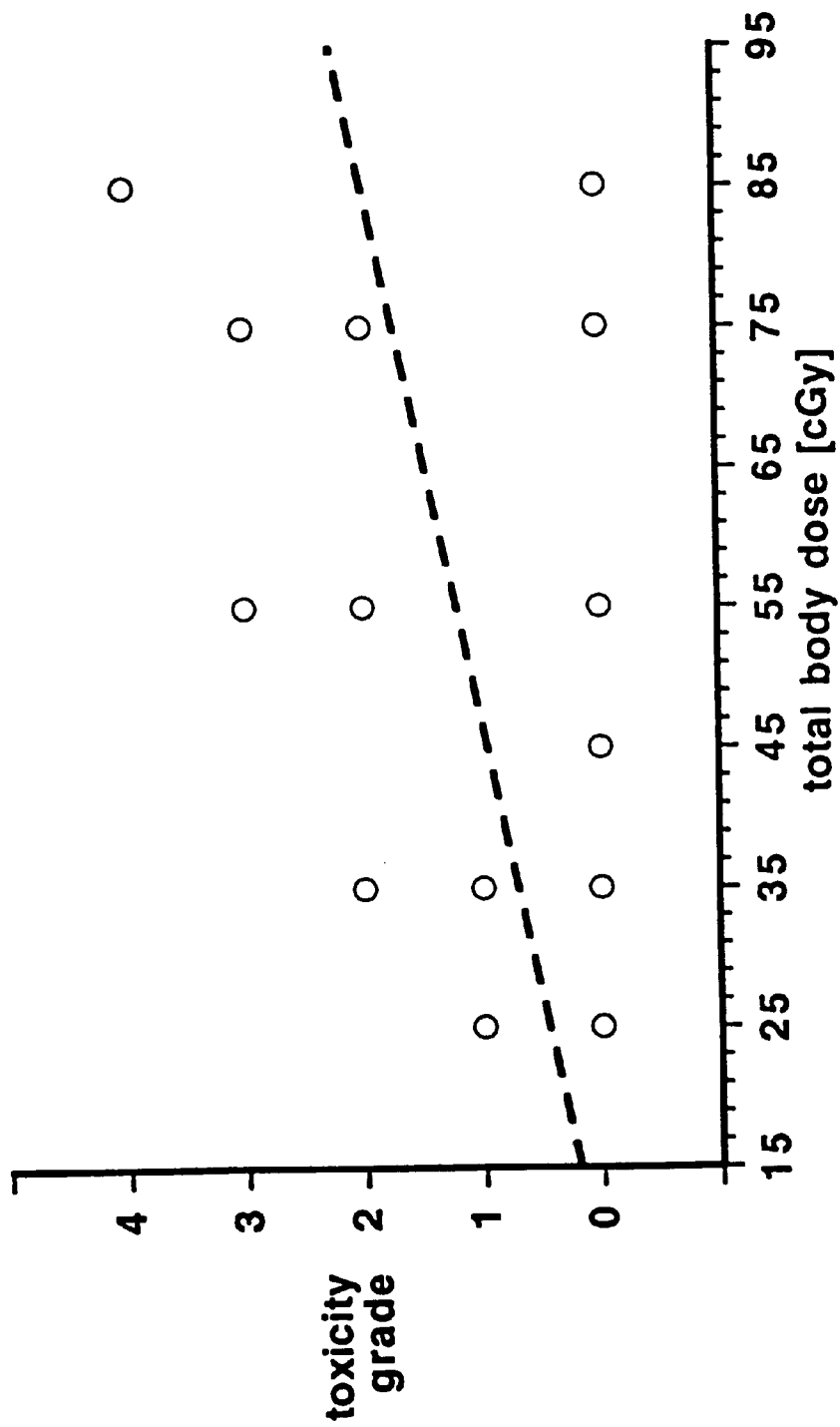

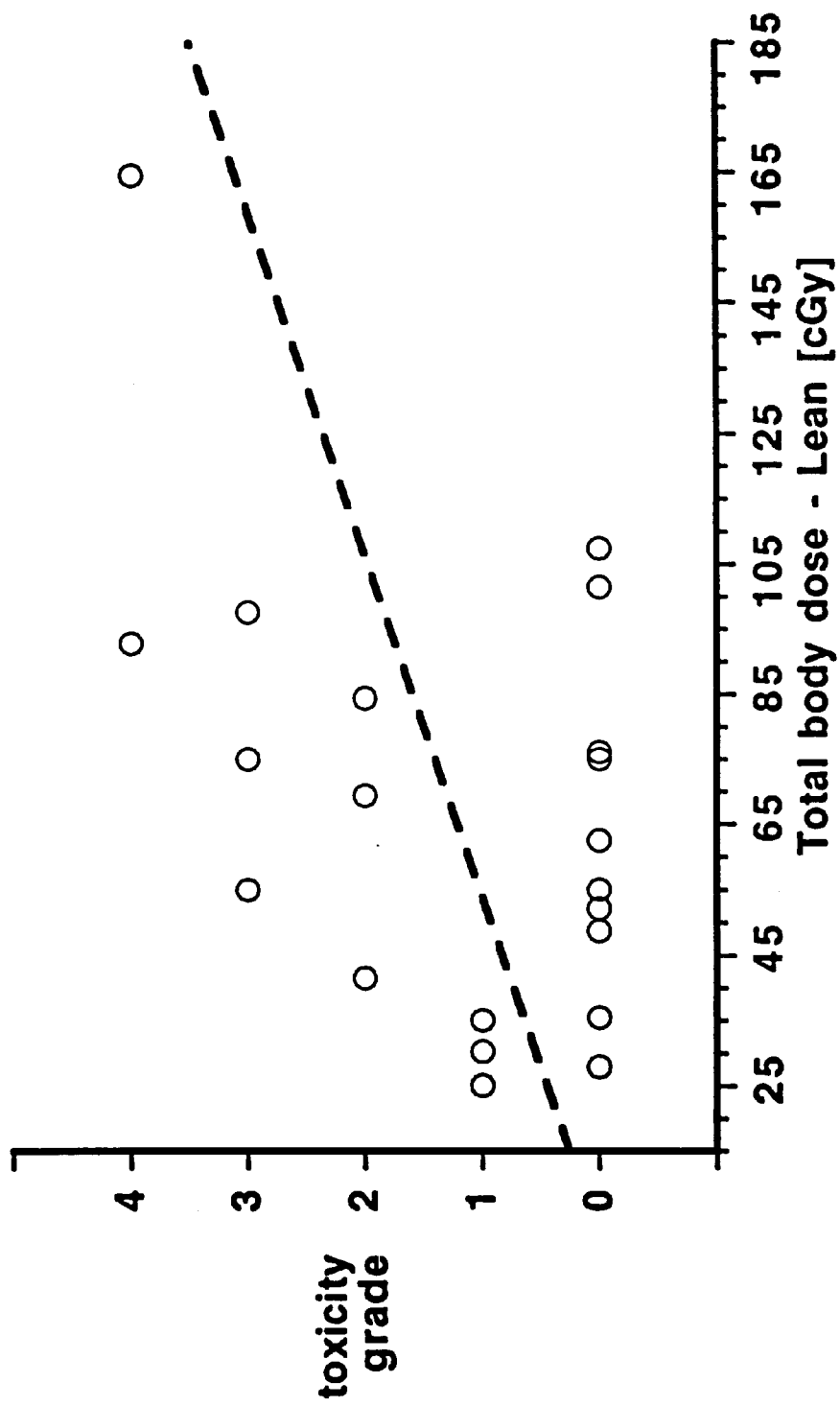

METHOD OF ESTABLISHING THE OPTIMAL RADIATION DOSE FOR RADIOPHARMACEUTICAL TREATMENT OF DISEASE

CROSS REFERENCE TO RELATED APPLICATION

This application is a continuation-in-part of application Ser. No. 08/433,674, filed May 4, 1995, now abandoned which is hereby incorporated by reference.

BACKGROUND OF THE INVENTION

1. Field of the Invention

The present invention relates to the administration of radiopharmaceutical compounds for the therapy of disease including cancer. More particularly, the present invention relates to a method of establishing the optimal effective radiation dose for treatment of disease, the method minimizing toxicity while preserving therapeutic activity.

2. Description of the Relevant Art

Radiopharmaceuticals are compounds composed of radioactive isotopes often bound to other molecules. These radiopharmaceuticals are used in assessing the presence, outline, size, position, or physiology of individual organs or tissues. More significantly for the present invention, radiopharmaceuticals are commonly used in the treatment of disease. For example, radioactive iodine (I-131) is used to treat thyroid cancer or overactive thyroids (Grave's disease). Of considerable importance is the development of monoclonal antibodies having attached radioactive labels. When combined with antibodies that are relatively specific for a particular diseased tissue, such antigen-specific monoclonal antibodies are able to selectively direct comparatively sizable amounts of radiation to the specific disease site. Such treatments are being applied to the treatment of non-Hodgkin's lymphomas, Hodgkin's lymphomas, Hepatoma, colorectal cancer, brain tumors, and many other forms of cancer. In addition, the treatments also have the potential to treat other types of disease, including auto-immune conditions such as, for example, Systemic Lupus and Rheumatoid arthritis. Targeted radiopharmaceutical therapy may be ultimately be found to be broadly applicable to a wide variety of neoplastic and benign diseases.

At present, the radiopharmaceutical is commonly introduced into the blood for ultimate internal distribution through conventionally known methods such as through intravenous, inhalation, or oral administration. A common unit of radioactivity is the millicurie, or mCi.

The general difficulty of the administration of radiopharmaceuticals for therapy lies in the fact that if the patient is given too much radioactivity, toxicity results. On the other hand, it is necessary to give enough of the radiopharmaceutical so that the disease is successfully treated.

The most common specific side effect of radiopharmaceutical treatment is bone marrow suppression or ablation. This is caused by the targeting of the radiopharmaceutical (or the radiolabel) to the bone or bone marrow or is due to circulation of the radioantibody through the blood vessels (including the marrow). In general, this situation could lead to bleeding, infection or death. This side effect (as well as other undesirable side effects) is caused by the inaccuracy of known methods used to determine the radioactive dose for the individual patient. For example, up to a five fold difference in the radiation dose to blood, bone marrow, or body received/mCi of the particular radioantibody administered may exist between patients. (Radiation dose is defined as the total amount of energy per unit mass deposited in an individual as a result of radioactive decay.) These differences are tied to the fact that individuals are physiologically different. Not only are individuals of different sizes and, to some degree, densities, they also differ in abilities to metabolize and clear radiopharmaceuticals. For example, if the radioactivity is attached to a monoclonal antibody, the radioactivity might be eliminated from different patients such that a half life of clearance of radioactivity of three days might be identified in a first patient, while a half life of clearance of radioactivity of six days is identified in a second patient.

Accordingly, the challenge facing the physician today is determining the correct number of millicuries to be administered to a particular patient having a particular disease at a particular stage of development of that disease. The number of millicuries to be administered is based on the prescription of a given radiation dose to the "whole body" of the patient, which is dependent upon several factors, including the patient's size and the rate of disappearance of radioantibody from the body as determined by direct measurements of the biodistribution of a tracer dose (a small, non-therapeutic quantity) of radioactivity using a gamma camera, probe detector system, or other radiation detection system. Using such an approach, a "whole body radiation dose" can be calculated from the tracer doses, which can be used to predict the radiation dose the "whole body" would receive from subsequent radiopharmaceutical therapy and which allows the radiation dose administered to be effective. Initial results with this approach using the anti-B-1 antibody have shown excellent therapeutic efficacy and modest toxicity. Results of clinical studies with this approach are detailed in NEJM 7:329, pp. 459–465, 1993 (Kaminski et al.), J. Nucl. Med. 35(5), 233P, 1994 (Wahl et al.), and J. Nucl. Med. 35(5), 101P, 1994 (Wahl et al.).

While this approach to calculating "whole body" radiation dose represents a major improvement over other methods which are not individualized to the patient's individual pharmacology, it still does not fully overcome the difficulties related to the accurate calculation of optimal radiation doses to treat radiosensitive tumors. The inherent failure of this method lies in the fact that the simple assumptions of "whole body" dose are not fully valid in terms of human patient physiology. Accordingly, while radiotoxicity is reduced, it is not fully eliminated or even absolutely minimized. Part of the reason for this failure is that the "whole body" dose approach assumes that a radiopharmaceutical is uniformly distributed throughout the body. There is an assumption underlying this thinking that the body is uniform, and that distribution of chemicals in the body is likewise uniform. This is not the case, as most radiopharmaceuticals, particularly intact monoclonal antibodies, have very limited accumulation in fat tissue compared to considerably greater accumulation in lean body tissue (including bone marrow).

In an effort to improve the accuracy of radiopharmaceutical mCi dosage, a method has been developed that utilizes a parameter directed to "total body dose-lean" (TBD-lean) to account for the fact that individuals may be modeled as an outer shell of fat (where little radioantibody or radiopharmaceutical accumulation occurs) which surrounds an active lean body mass, including bone marrow. This method is disclosed in the present inventors' copending application entitled METHOD FOR THE REDUCTION OF TOXICITY OF RADIOPHARMACEUTICAL THERAPY, Ser. No. 08/433,674, filed on May 4, 1995. As set forth in the copending application, by appreciating the fact that in man there is a "lean body" within a "fat" outer shell, a formula may be used to estimate what percentage of the person is fat and what percent of the person is lean. Thereafter, the radioactivity is traced as essentially being distributed uniformly and totally through the lean component. By first estimating what fraction of the body is lean and then calculating the radioactivity distribution within a given lean volume, the proper dose of radiopharmaceutical for treatment without undue toxicity can be administered on an individualized, case-by-case basis.

While resolving many of the difficulties related to the prescription of effective amounts of radiation doses, the prior art nevertheless may be improved upon.

SUMMARY OF THE PRESENT INVENTION

The present invention is directed to a method for determining the number of millicuries to be administered to a patient as a dose so as to establish a given centigray (cGy) dose to either the patient's lean body or the patient's total body. According to the present invention, the following steps are followed.

Initially the rate of clearance or disappearance of radioactivity from a patient is determined by direct measurement across multiple time points using a radiation detection device (such as a NaI probe or a gamma camera). This step determines changes in the radiation concentration of a particular patient over a given period of time. For example, a series of measurements, commonly seven or eight, are done over a period of a week with the first measurement made immediately following a tracer injection of the radiopharmaceutical. The time in hours is determined from the end of the tracer infusion for each measurement, resulting in a variety of values. Appropriate measurement is made of the amount of radioactive disintegration measured from the front of the patient (anterior measurements) and/or from the back of the patient (posterior measurements).

Based on these readings, a geometric mean is calculated. The geometric means may be based upon daily NaI probe measurements, but may also be based upon anterior and posterior conjugate view gamma camera imaging data or other methods of radiation detection. According to the conjugate view approach, a geometric mean is calculated for each time point by multiplying the anterior and posterior readings and determining the square root of the total figure. This mean represents an average number of counts. The background counts are subtracted for a corrected mean. The percent injected activity remaining in the body for each time point is thereafter determined by dividing the counts at a given time by the counts immediately after the tracer is injected. Thereafter, the percent of injected activity versus the calculated time from infusion is plotted on a log linear graph. With these points established on the log linear graph, a line is drawn to determine the intersection of the best fit line with the 50% injected activity line, thereby determining effective half life, or T ½-effective.

With T ½-effective thus established and the patient's body weight known, these values are cross-indexed on either a graph (the "graphical" approach) or on a table (the "tabular" approach) to determine the recommended millicuries per centigray (mCi per cGy) to be administered (activity per unit TBD or TBD-lean). (Both the graphical approach and the numerical approach represents activity per unit for total body dose [TBD] or total body dose-lean [TBD-Lean] as a function of total body or lean body mass and T ½-effective.) Both the graphical and numerical approaches (and their expressed quantities) are features of the present invention.

The actual amount of therapeutic millicuries is then determined by multiplying the recommended mCi per cGy by the amount of desired centigray to be administered.

While the present invention is described as having application to whole body dose and lean body mass, the method of the present invention is also applicable to dosimetry to blood, bone marrow, and other organs and tissues such as the lung, the liver, and the kidney.

These and other features of the present invention are best understood from the following specification, drawings and examples.

BRIEF DESCRIPTION OF THE DRAWING

FIG. 1 is a blank worksheet onto which are to be entered all necessary intermediate values based upon observations of clearance of the tracer from the body;

FIG. 2 is a blank graph consisting of a long linear graph onto which pertinent elimination values are to be marked at different intervals of time;

FIGS. 7a through 7v define a series of tables (specifying activity per unit Total Body Dose [TBD] or Lean Body Dose [TBD-Lean] as a function of Total Body or Lean body mass and T ½ effective) used for determining the therapeutic mCi/cGy to be administered based on known T ½ [hr]-effective along the X-axis (AO [mCi/cGy]) and the patient's mass (in Kg), total body mass (in Kg) for TBD, and lean body mass (in Kg) for TBD-Lean along the Y-axis;

FIG. 9 is chart summarizing the input and output data of twenty-one sample patients;

FIG. 11 is a toxicity versus total body dose [cGy] graph with the data points of the twenty-one sample patients of FIG. 9; and FIG. 12 is a toxicity versus total body dose-lean [cGy] graph of the data points of the twenty-one sample patients of FIG. 9.

DETAILED DESCRIPTION OF THE PREFERRED EMBODIMENT

Figure 3:
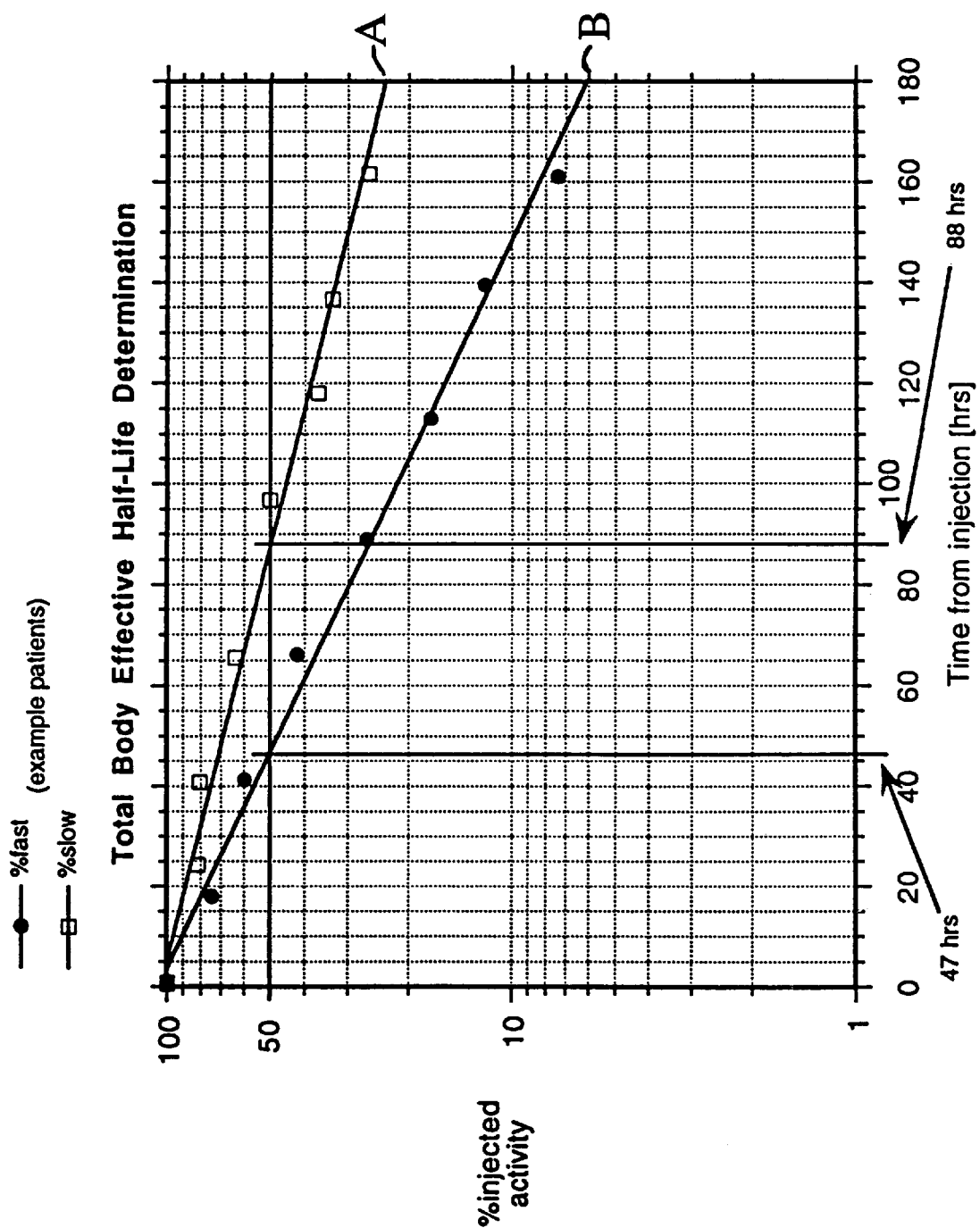
FIG. 3 is similar to the graph of FIG. 2 but illustrating two series of elimination values for two sample patients.

The present invention is directed to the need to determine the amount of radiopharmaceutical compound delivered to a patient in the treatment of disease so as to present the smallest possible amount of toxicity to the body while providing maximum treatment for the disease. In essence, the present invention is directed to the "fine-tuning" of the administration of radio-pharmaceutical compounds.

Briefly, the present invention involves the following steps:

(1) Injecting a radioactive tracer into a patient;

(2) determining radiation levels in the whole body;

(3) calculating a geometric mean;

(4) determining the percent-injected activity remaining in the body at each time point;

(5) plotting the percent-injected activity versus calculated time from infusion on a log-linear graph;

(6) determine the effective half-life (and the rate of clearance) from the log-linear graph by identifying the intersection of the best fit line with the 50% injected activity line;

(7) cross-index the effective half-life value with the patient's body weight (either total body mass for total body dose or lean body mass for total body dose-lean) on either a graph or on a numerical chart to identify the actual amount of therapeutic millicuries; and (8) multiply the determined amount of therapeutic millicuries by the amount of desired centigray to be administered.

These steps along with their associated substeps are set forth in detail as follows and are to be read in correlation with the several figures discussed in conjunction therewith.

DETERMINATION OF RATE OF CLEARANCE

Determining the rate of clearance of an injected dose of a particular radiopharmaceutical is critical to the determination of the amount of therapeutic dose to be administered. A person who clears the injected dose quickly would receive a relatively large therapeutic dose of the particular radiopharmaceutical drug as compared to a person who clears the injected dose less quickly. This is simply because of residence time—the longer the radio-pharmaceutical is proximate to the disease site, the less need be administered. Quick clearance translates into brief exposure to the radioactive element and less effective treatment of the disease. (Other factors determine the administered radiation dose, including the size of the patient and the desired total centigray amount.)

Rate of clearance is determined by administering an amount of a "tracer dose" to the patient. The tracer dose represents a small amount of radioactivity attached to an antibody. The particular antibody is selected according to its specificity to a target antigen. The "tracer dose" (in mCi) represents the amount of radioactivity that is initially administered to the patient. (The "tracer" aspect of this dose does not refer to a trace amount of antibody, but rather to the trace amount of radioactive material attached to the antibody. The antibody mass is delivered during the stage of estimating the rate of clearance in the same amount as in therapy, however, the amount of radioactivity [the number of millicuries] is lower to prevent toxicity to the system. Experimentation has shown that the tracer dose is, in fact, a reliable predictor of the therapeutic dose. Special measurements taken after therapy initially based upon a tracer dose has shown that the kinetics of clearance of the antibody with the tracer amount generally predict the effectiveness of the therapeutic amount; in fact, these results are substantially identical.)

After administration of the tracer dose, the course of timing of the elimination of the tracer dose is thereafter followed. The tracer dose is first injected into the patient over a period of time, such as 40 minutes. Thereafter a probe is used to determine anterior and/or posterior counts, thus quantitatively demonstrating the amount of radioactivity remaining in the body after certain intervals of time. Measurements may be taken by any of several devices including a sodium-iodine probe, a gamma camera, a geiger counter, a whole-body counter, etc. Measurements are taken once approximately every 24 hours over a course of several days. Infusion stop and start times are recorded, as are counts taken for elimination over several 24-hour periods. The relevant intermediate numerical values are entered onto a worksheet such as that illustrated in FIG. 1.

Once the counts are recorded over the requisite time period, the geometric mean is obtained. This may be done by taking readings from daily NaI probe measurements, but also may be done by relying upon readings from anterior and posterior conjugate view gamma camera imaging. When the latter approach is used, a geometric mean is obtained for each set of recorded anterior and posterior counts (representing an individual time point) is determined by the following formula:

$$\text{geometric mean} = \sqrt{\text{anterior count} \times \text{posterior count}}$$

The determined geometric mean is not corrected for radioactive decay. Once the geometric mean is known, net geometric mean counts are calculated by subtracting background counts according to the following formula:

$$\text{geometric mean (net)} = \text{geometric mean} - \text{bkg}$$

For example, if the background count is 100 cpm and the patient's count is 2000 cpm, then the net counts to the patient would be 1900 cpm.

Thereafter, the percent-injected activity remaining in the body at each time point is determined by forming a ratio to the geometric mean at the initial time point (again, not corrected for radioactive decay) according to the following:

$$\text{percent-injected activity (at each time point)} = \frac{\text{geometric mean (net)}}{\text{geometric mean (initial)}} \times 100\%$$

Once the percent-injected activity for each time point is known, these values are entered into a graph to determine total body effective half life. FIG. 2 is a blank graph consisting of a log linear graph onto which the pertinent values are to be marked. The percent-activity is read along the Y-axis (log scale) and the time from injection (in hours) is read along the X-axis (linear scale).

FIG. 3 is the graph of FIG. 2 now completed and showing the relevant values of two patients. Patient "A" is denoted by a series of eight open boxes representing measurements of percent-injected activity recorded over a period of 160 hours. Patient "B" is denoted by a series of eight closed circles also representing measurements of percent injected activity recorded over the same period of time. Lines are drawn through the respective series of open boxes or closed circles to establish the respective curves.

The effective half-life for each patient is determined by identifying the point at which the respective curves intersect the 50% injected activity level, indicated by a horizontal line on the charts of both FIGS. 2 and 3. This point represents the effective half-life, or T ½-effective. Given, for example, Patient A, T ½-effective is 88 hours, while T ½-effective for Patient B is 47 hours. Obviously, Patient A clears the injected dose more slowly than does Patient B.

TOTAL BODY DOSE VERSUS TOTAL BODY DOSE-LEAN

The present invention improves on the known techniques of determining the optimal dose for administration of therapeutic radiopharmaceuticals in several ways. One such improvement rests in the unsettling of the previously-held notion that doses of therapeutic radiation could be determined based on patient weight. This notion fails to take into account several variables, including "fat" versus "lean" compartments and the related effects of "total body dose" versus "total body dose-lean".

The body represents two major compartments, a "fat" compartment and a "lean" compartment. The corollary to this is that the "lean" person resides within an outer shell of "fat". These related theories represent a major departure from other approaches to dosimetry. Accordingly, a calculation of the quantity of the patient which is "lean body mass" can be made. From this new mass and new shape which essentially isolates the "lean" from the "fat", a new and more accurate radiation dose can be determined to the "lean body" using methods of least squares or graphical fitting of kinetic radioantibody clearance data and assumptions of non-uniform distribution of radioactivity between the two body compartments.

Figure 4:
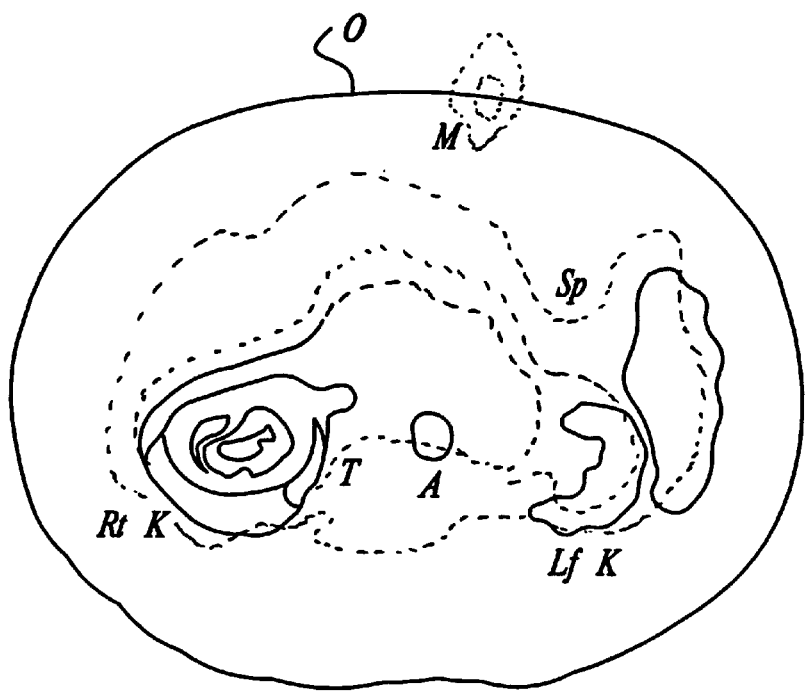
FIG. 4 is a line of a fused image of various sectional views of the central body compartment of a sample patient following administration of radiolabeled antibodies.

FIG. 4 demonstrates the significance of distinguishing between "lean" and "fat" body compartments. FIG. 4 is a "fused" image of a cross-section of a patient following administration of radiolabelled antibodies. The image is produced by a fusion computer program that superimposes a CT image slice corresponding to a SPECT image slice. Details of this procedure and its application are set forth in an article by K.F. Koral et al. and entitled CT-SPECT FUSION PLUS CONJUGATE VIEWS FOR DETERMINING DOSIMETRY IN IODINE-131-MONOCLONAL ANTIBODY THERAPY OF LYMPHOMA PATIENTS (J. Nucl. Med., Vol. 35, No. 10, October 1994, pps. 1714–1720). Generally, FIG. 4 illustrates a central body compartment that includes the major organs such as the kidneys and spleen. The individual images are scaled by a computer so they substantially overlap when superimposed. The lighter areas are areas of relatively high amounts of radioactivity, while the darker areas are areas of low radioactivity.

With respect to FIG. 4, a tumor, T, is shown in close association with the right kidney, labeled Rt K. Other organs illustrated include the aorta, A, the left kidney, Lf K, and the spleen, Sp. The patient's external body outline, labeled O, is illustrated, having thereupon a marker, M, to demonstrate the position of the body outline O. The outline O is the outer boundary of the patient and therefor represents the air-skin interface. The black area is mainly non-lean tissue, with the gray areas being the central area or the leaner body mass. As illustrated, there is a considerable amount of radioactivity in the vascular or lean component where antibody presence is the greatest. There is comparatively little radioactivity in the non-lean tissue, as illustrated by the black color. The patient illustrated in FIG. 4 is a relatively large person having an excess amount of body fat. The body outline O would be closer to the internal organs on a thinner person.

While clearly illustrating the differences in uptake of the radiolabeled antibody between the lean and non-lean compartments, FIG. 4 also demonstrates how it is generally not possible to target the disease site itself. While careful selection of a particular antibody will minimize cross-reaction with normal tissue, interaction (specific or non-specific) with non-disease tissue invariably results, in that as antibodies are directed to the tumor through blood vessels, the same vessels will naturally transport the antibodies in places other than to the disease site.

FIG. 4 also illustrates the simple assumption of the present invention that all (or substantially all) radioactivity resides in the "lean" compartment, while none (or virtually none) resides in the "fat" compartment, which encases the "lean" compartment. With the further assumption that the bone marrow is part of the freely accessible "lean" compartment, a beta particle dose and photon dose to the "lean" compartment can be determined. These estimations are important, in that the total amount of energy deposited in an individual as a result of radioactive decay is the "radiation dose" which is adjusted per unit weight for the particular individual or tissue and for a particular radioactive material. A specific example is the radioactive material I-131 which is both a beta emitter and a gamma emitter. Following injection of an antibody labeled with I-131, for example, the central "lean" compartment of the body emits both beta and gamma particles. The beta particles are more or less confined within the compartment, while only some of the gamma particles are so confined. The extent to which the gamma particles are confined depends on the sizes of the "lean" and "fat" compartments. Some of the gamma particles strike some fat tissue and are scattered, returning to the "lean" compartment. Accordingly, not only does accurate quantification of the "lean" and "fat" compartments assist in eliminating reliance on the pure weight of a body in determining dose administration, an understanding of these compartments with respect to the individual patient also aids in determining, with greater accuracy, the "tracer dose" and its elimination.

Accordingly, it may now be understood that total body dose (TBD) assumes that all radioactivity is uniformly distributed throughout the patient's total body mass, and that all beta/electron energy is absorbed in the total body mass. TBD calculations for photon energy deposition are made from absorbed fractions of emissions of the radioactive material (for example, I-131) in the ellipsoid of mass equal to the total body mass. Conversely, total body dose—lean (TBD-Lean) is modeled as a lean-body mass ellipsoid surrounded by a fat-layer ellipsoid shell. TBD-Lean assumes that all radioactivity is uniformly distributed throughout the patient's lean body mass, since there is little tracer distribution to fat. In the TBD-Lean model, all beta/electron energy is absorbed in the lean-body mass, and photon energy is absorbed in lean-body mass ellipsoid volume. This said, it is clear that the more obese the patient, the more important dosage be based on the TBD-Lean model. Conversely, dosage for a relatively thin person could be reliably based on the TBD approach. However, regardless of the approach, the present method of determining optimal radiation dose could be used with either the TBD or the TBD-Lean model, with the latter model providing the better determination, particularly in the case of the obese patient.

Figure 5:
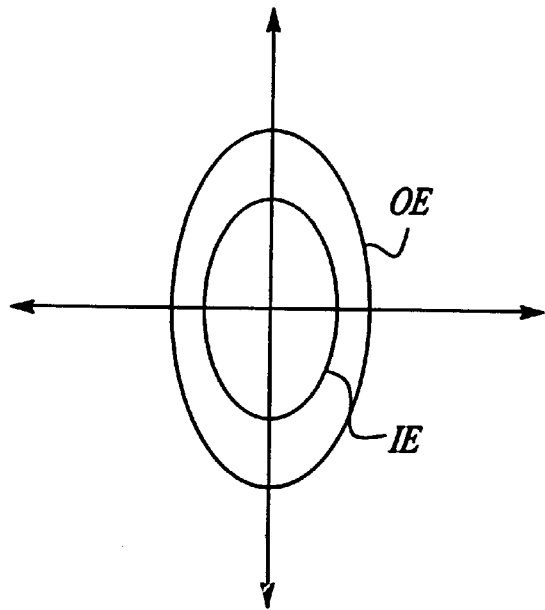
FIG. 5 is a graph illustrating the relationship of the fat component of the individual with respect to the lean component of the same individual.

FIG. 5 illustrates the relationship of the fat component of the individual with respect to the lean component and accordingly is a visually simplified version of the actual section shown in FIG. 4. An individual can be thought of as two ellipsoids, with the length x-1 or x-2 and with y-1 or y-2. The outer ellipsoid, labelled OE, with the larger x and y dimensions represents fat plus lean mass, with a volume (in liters) approximately equal to the patient's weight (in kilograms). The inner ellipsoid, labelled IE, with the same aspect ratios, is defined in liters by the following formulae that determine "lean body mass" (LBM):

$45.5 + 0.91 \times (\text{height [in cm]} - 152) = \text{LBM}$ for females $48.0 + 1.06 \times (\text{height [in cm]} - 152) = \text{LBM}$ for males It should be understood that total LBM could also be directly measured by CT, x-ray absorptiometry, immersion weighing, and other known methods. The total body absorbed dose is then determined for the lean body ellipsoid based on conventional calculations. It should also be understood that corrections for Compton scatter of photons from the fat compartment or some trace accumulation in the fat compartment are also possible, but need to be included in the simplest application of the present method. Following this general guideline, the method of determining the patient's LBM is set forth in applicants' above-mentioned copending application entitled METHOD FOR THE REDUCTION OF TOXICITY OF RADIOPHARMACEUTICAL THERAPY, Ser. No. 08/433,674, filed May 4, 1995, and incorporated herein by reference.

DETERMINATION OF THE WHOLE BODY DOSE

With the effective half life or T ½-effective determined from tracer study, the whole body dose may be calculated. By "whole body dose", it is meant that these calculations are made for the whole body or for the lean body mass component of the whole body.

The calculations of the whole body dose are based on the assumption that the radioantibody is uniformly distributed throughout the patient (or the lean body mass compartment) following tracer injection and that the tissues are of uniform water density. Accordingly, determining the patient's mass (or lean body mass as set forth above) determines the assumed water content and patient volume for dosimetric calculations. The "total body residence time" is an integral of the time activity curve for the total body divided by the injected activity according to the following formula:

$$\tau_{TB} = \frac{1}{A_0} \int_0^\infty A_{TB}(t) dt = \frac{T\,1/2\text{-effective}}{\ln 2}$$

The relative contributions of electron and photon radiation are summed to produce the total body radiation dose ([cGy]/mCi) administered. The formula for this determination is as follows, where the total body dose is the sum of electron energy plus photon energy deposited in an ellipsoid having a mass $m_{TB}$:

$$\frac{D_{TB}}{A_T} = \frac{\tau_B}{m_{TB}} \left[ \sum_{elec} \Delta_{elec} + \sum_{phot} \Delta_{phot} \phi_{phot}^{TB} \right]$$

This equation can be solved for $A_T$, the therapy activity in mCi to impart a given total body dose, $D_{TB}$.

Figure 6:
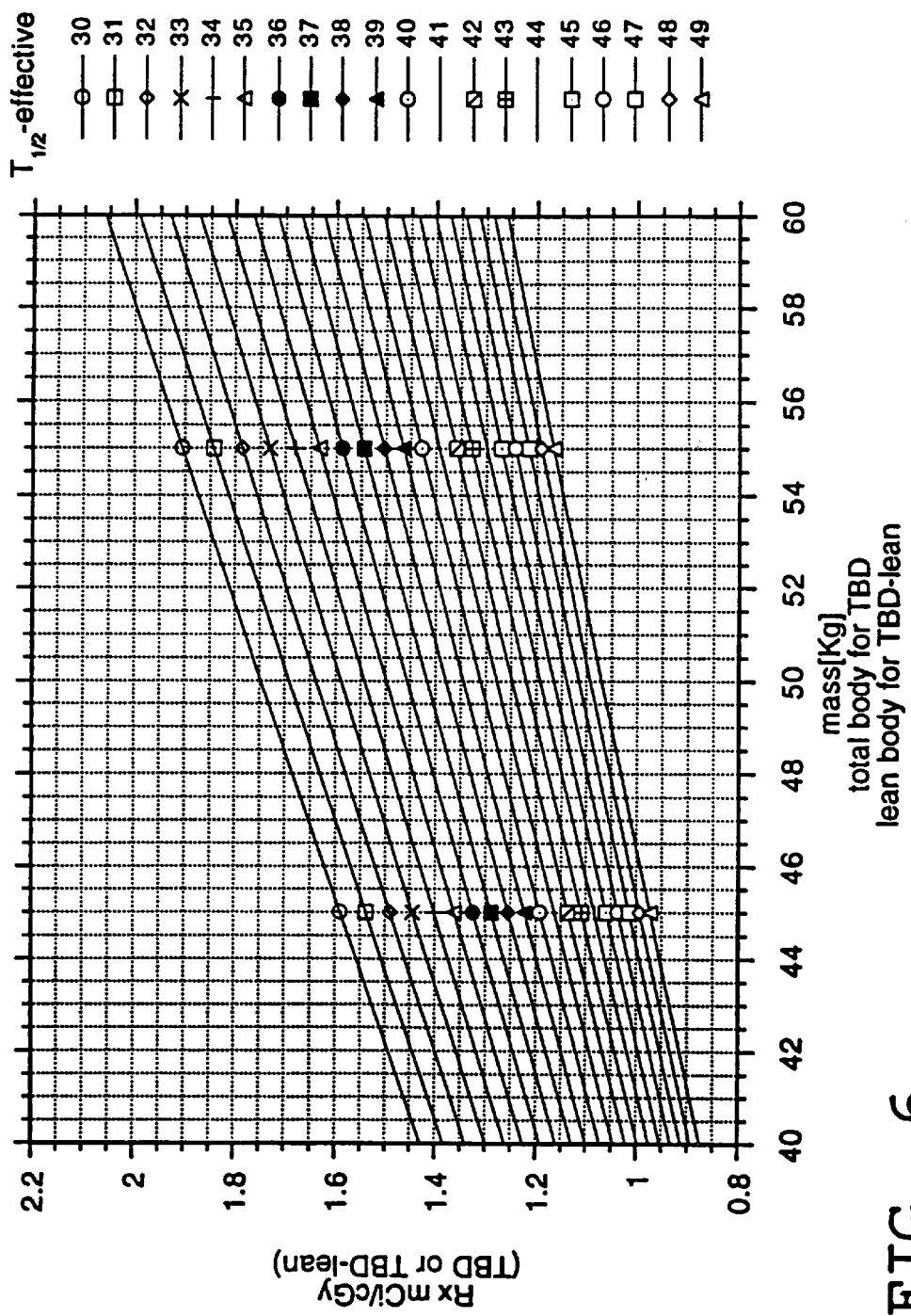
FIGS. 6a through 6o define a series of graphs used for determining the therapeutic mCi/cGy to be administered based on known T ½-effective and the patient's mass (in Kg), total body mass (in Kg) for TBD, and lean body mass (in Kg) for TBD-Lean.
Figure 6A:
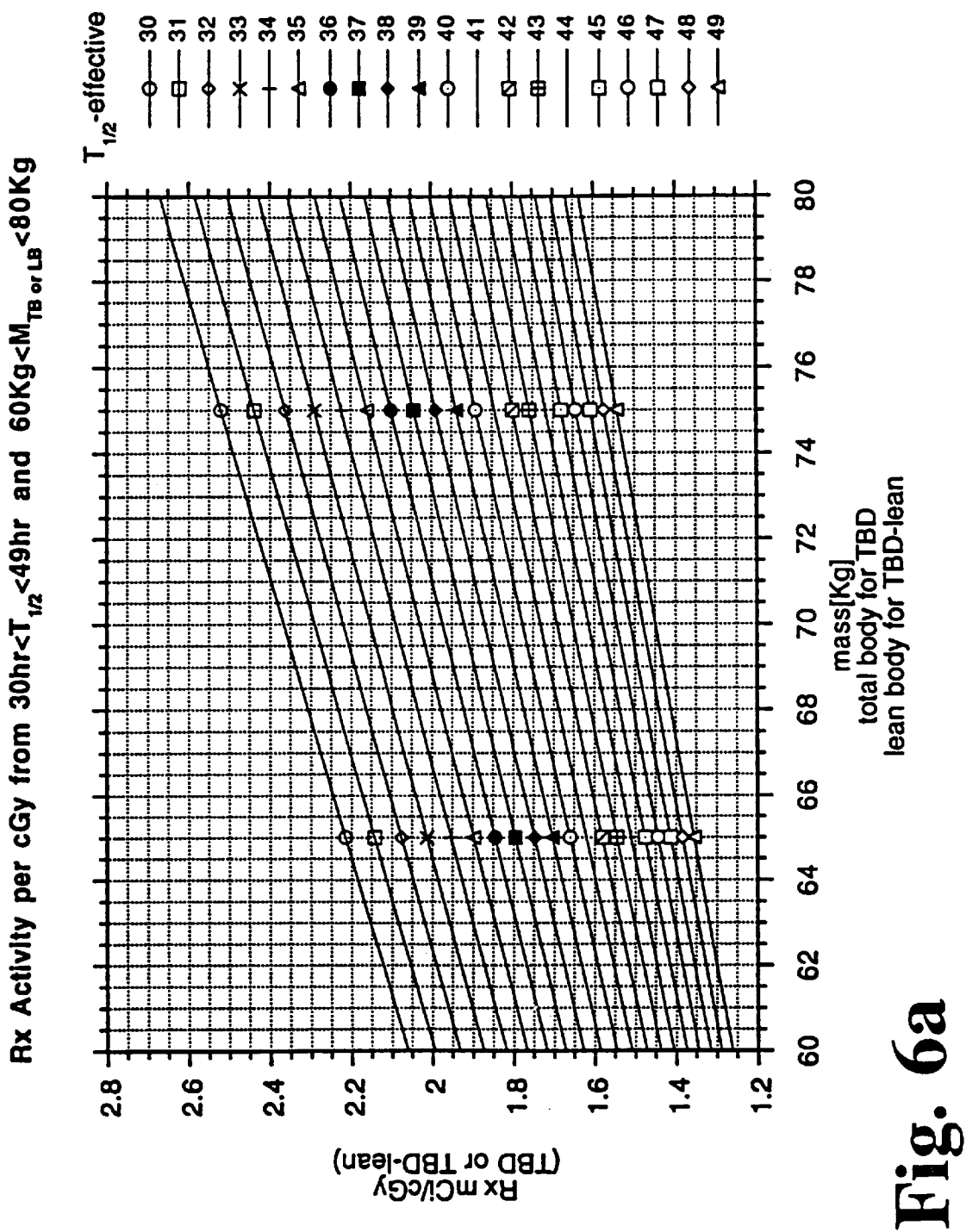
Figure 6B:
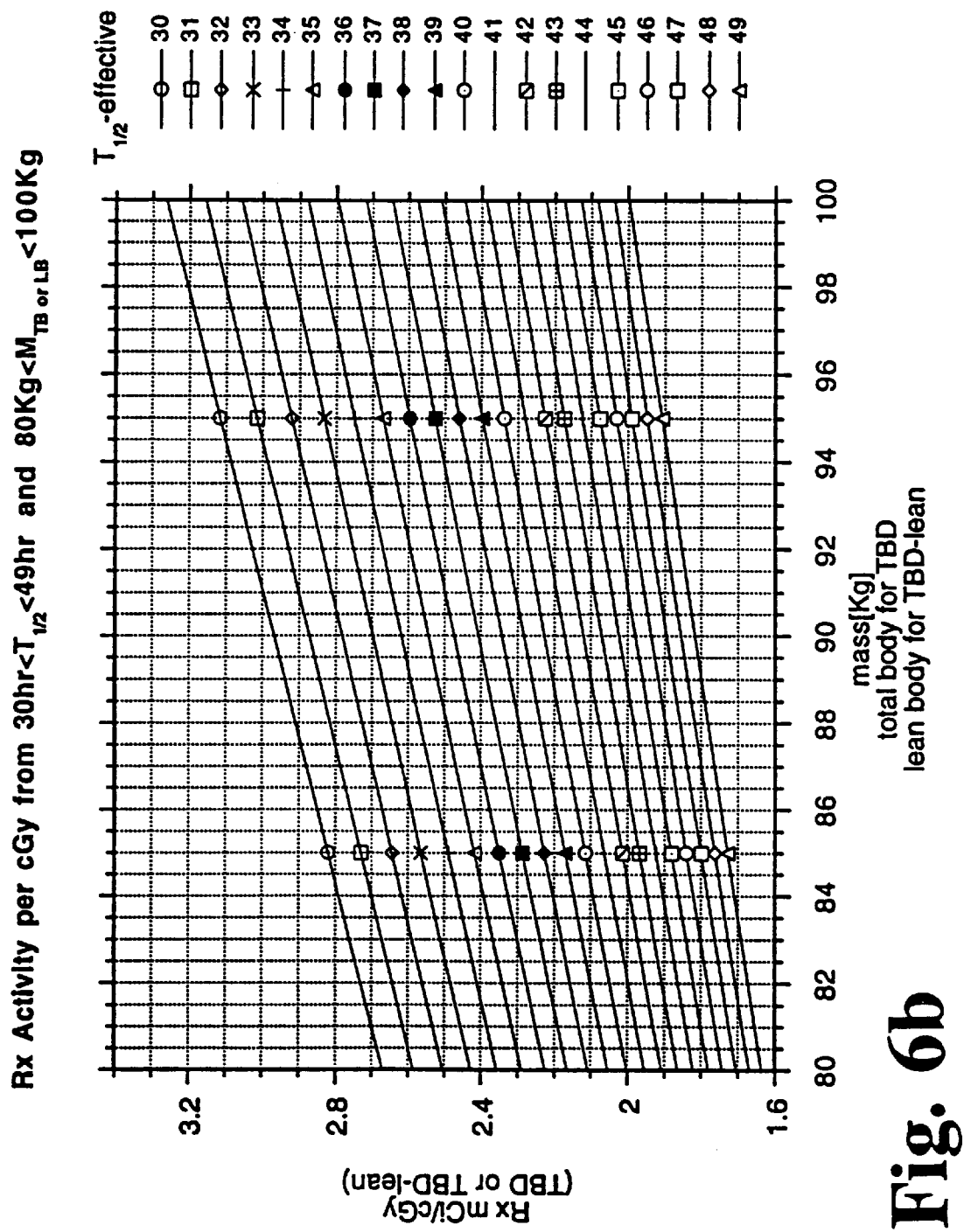
Figure 6C:
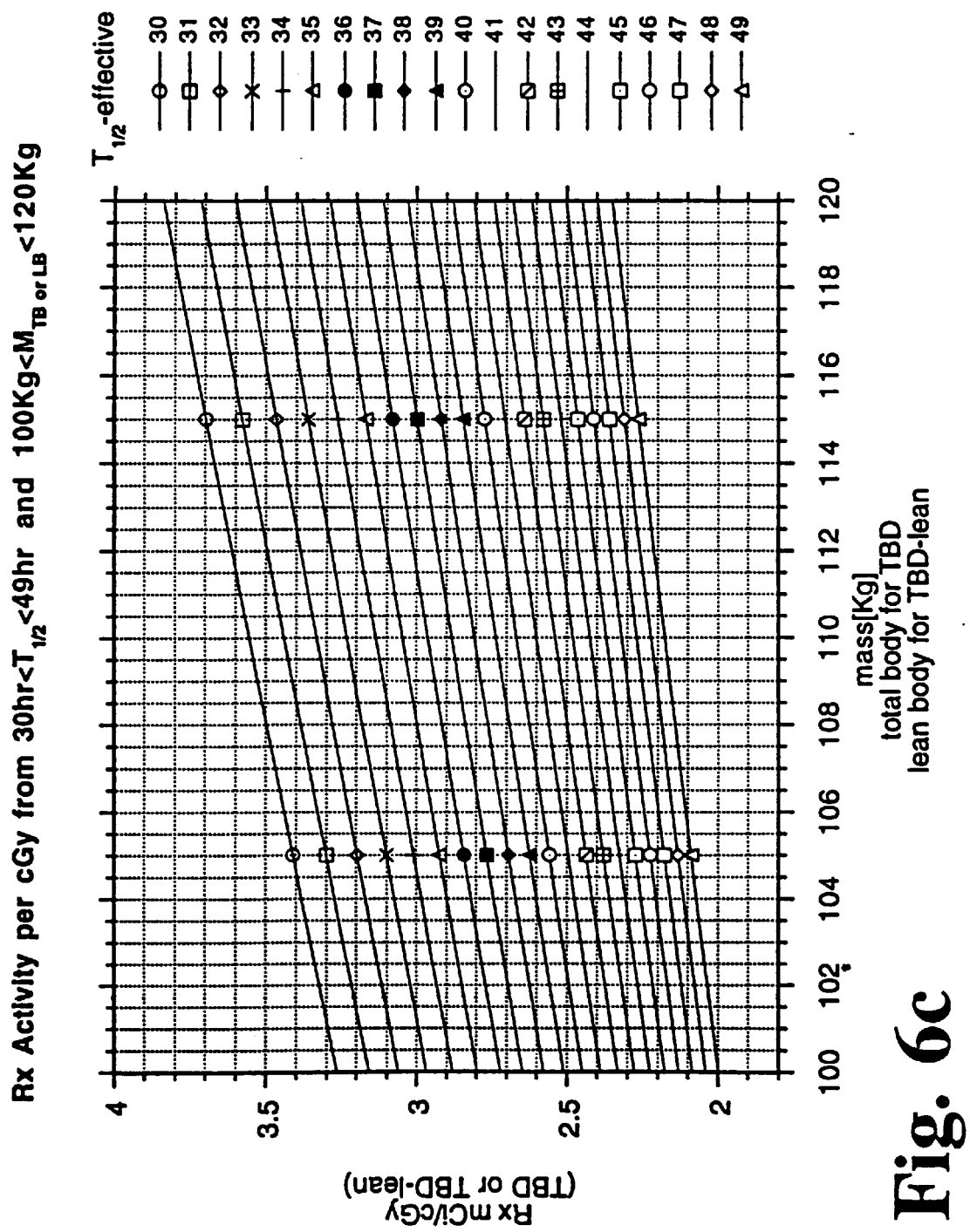
Figure 6D:
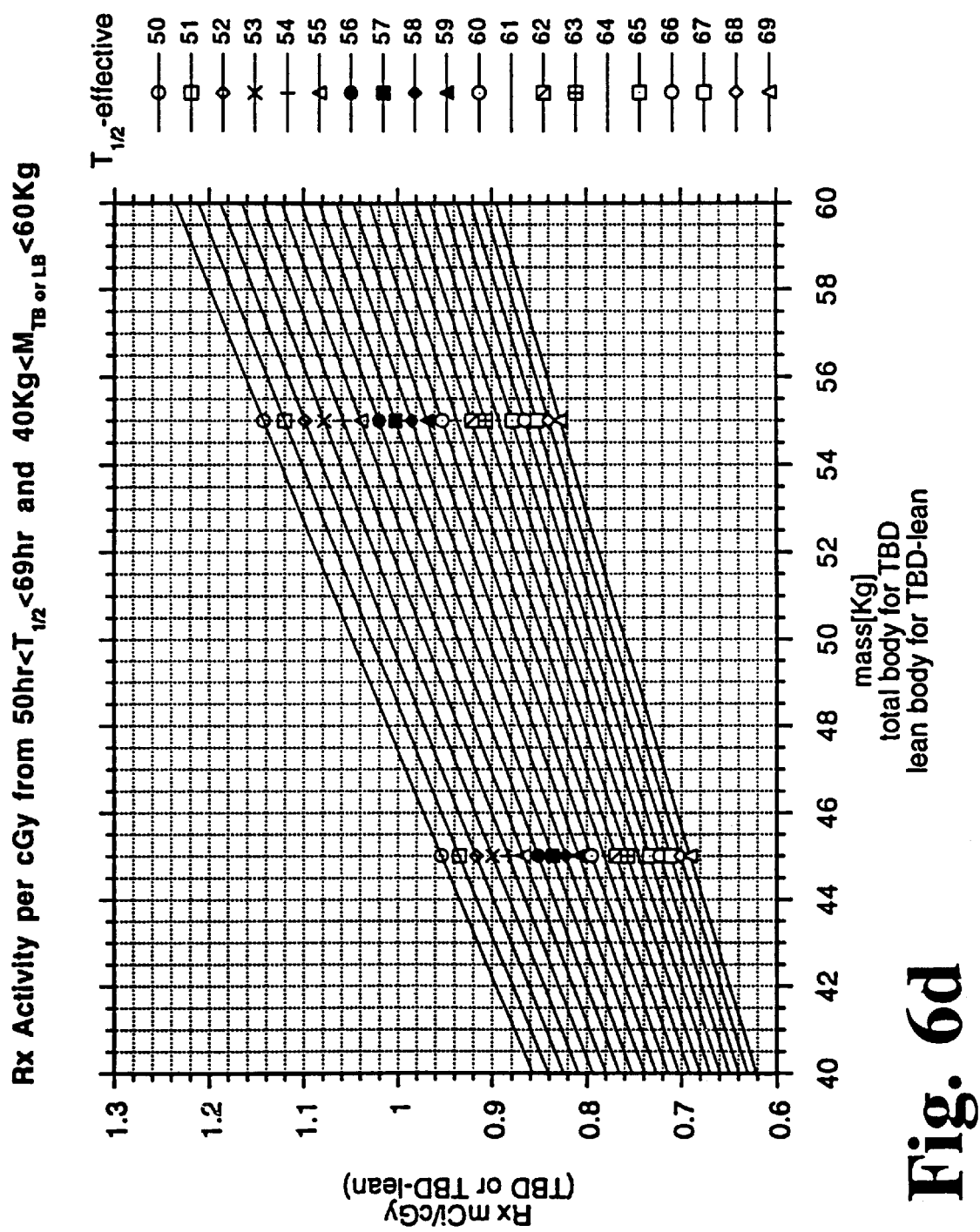
Figure 6E:
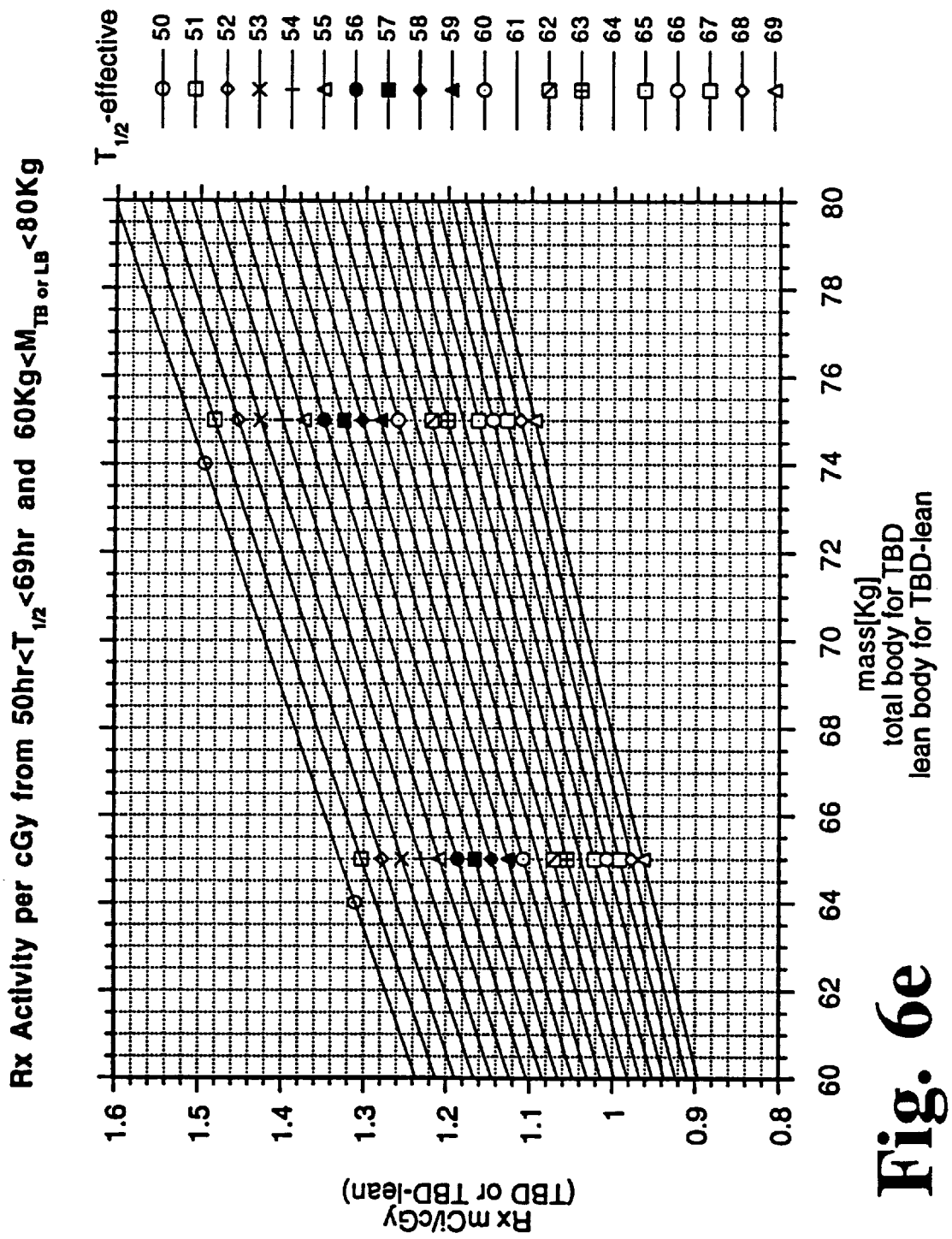
Figure 6F:
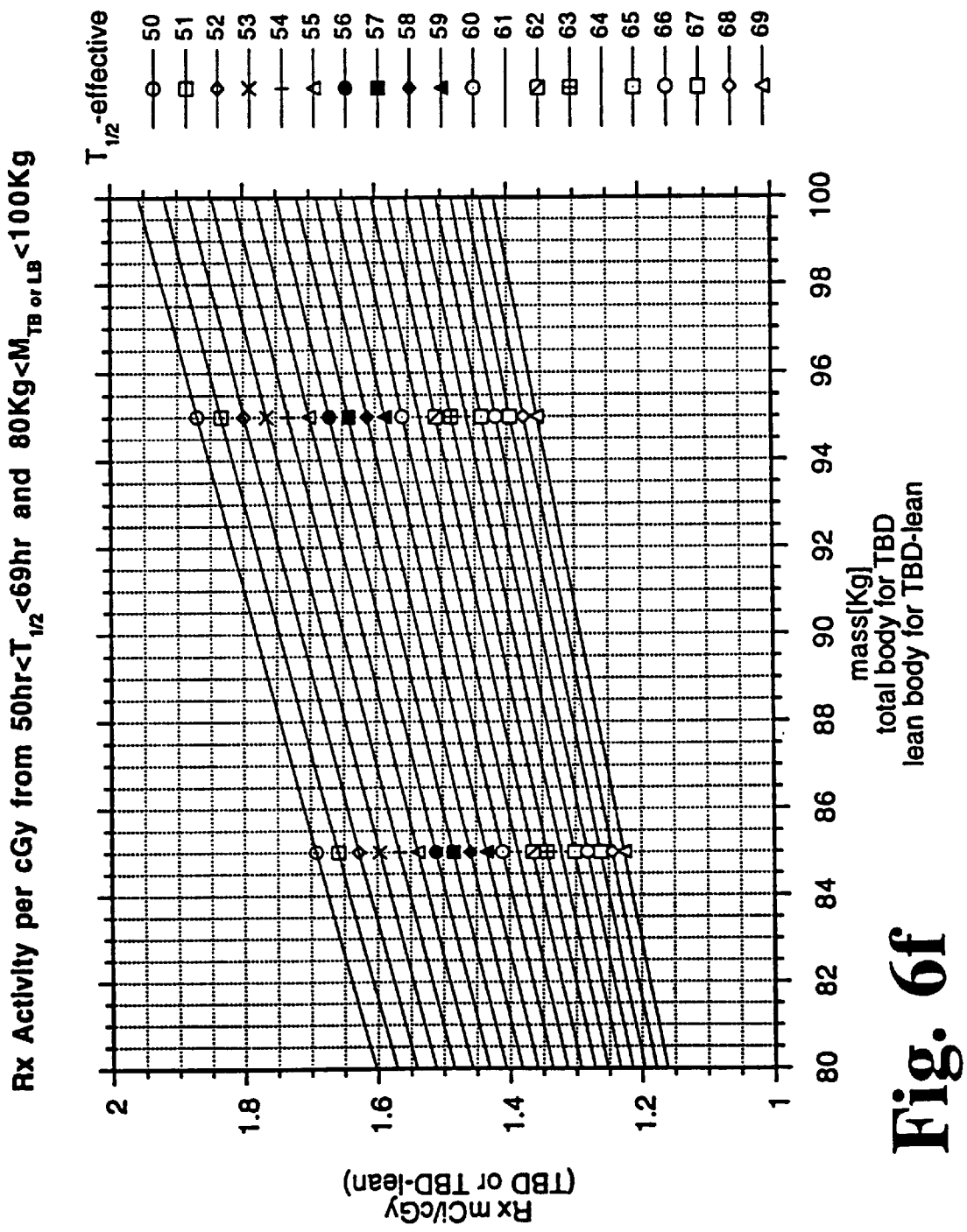
Figure 6G:
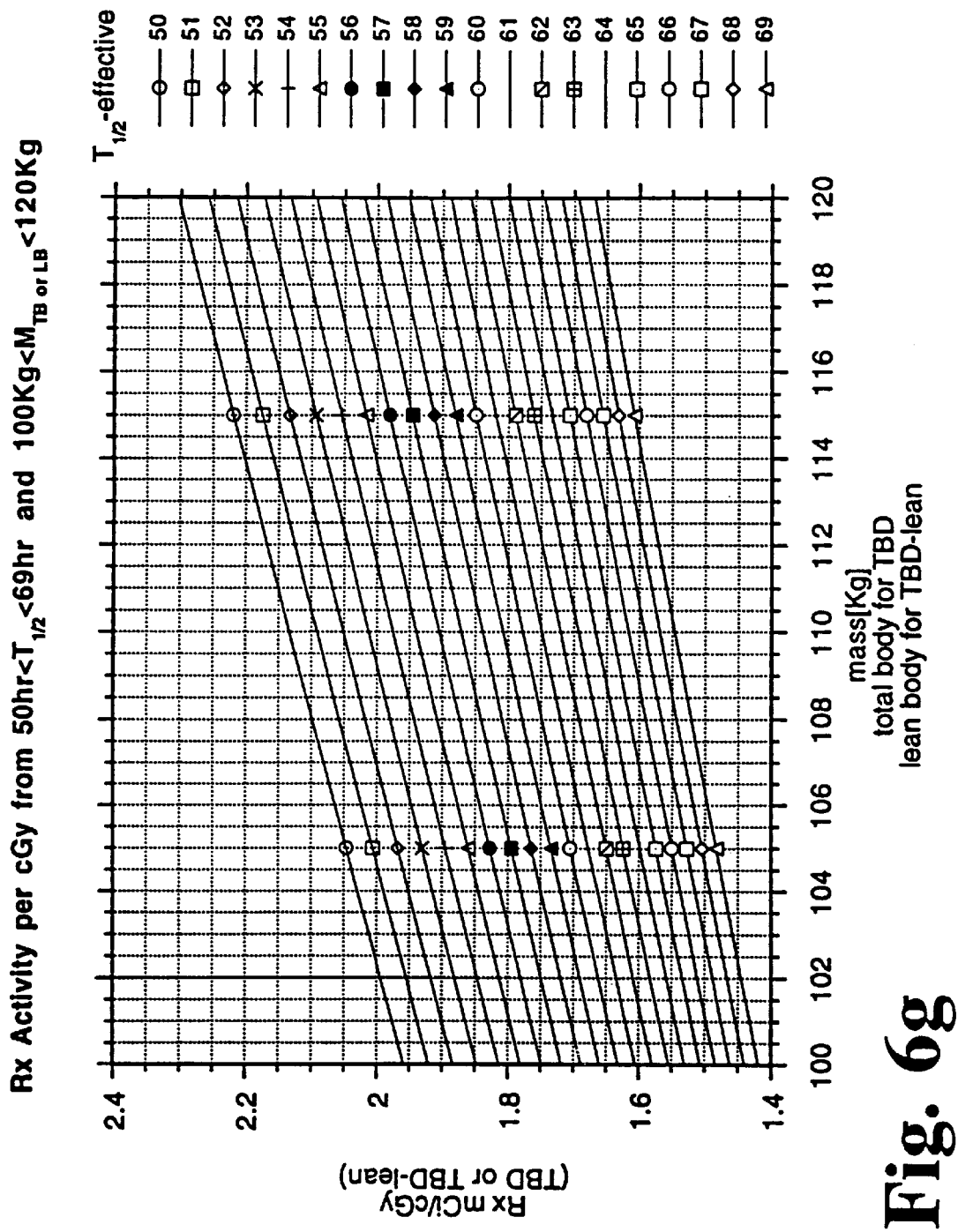
Figure 6H:
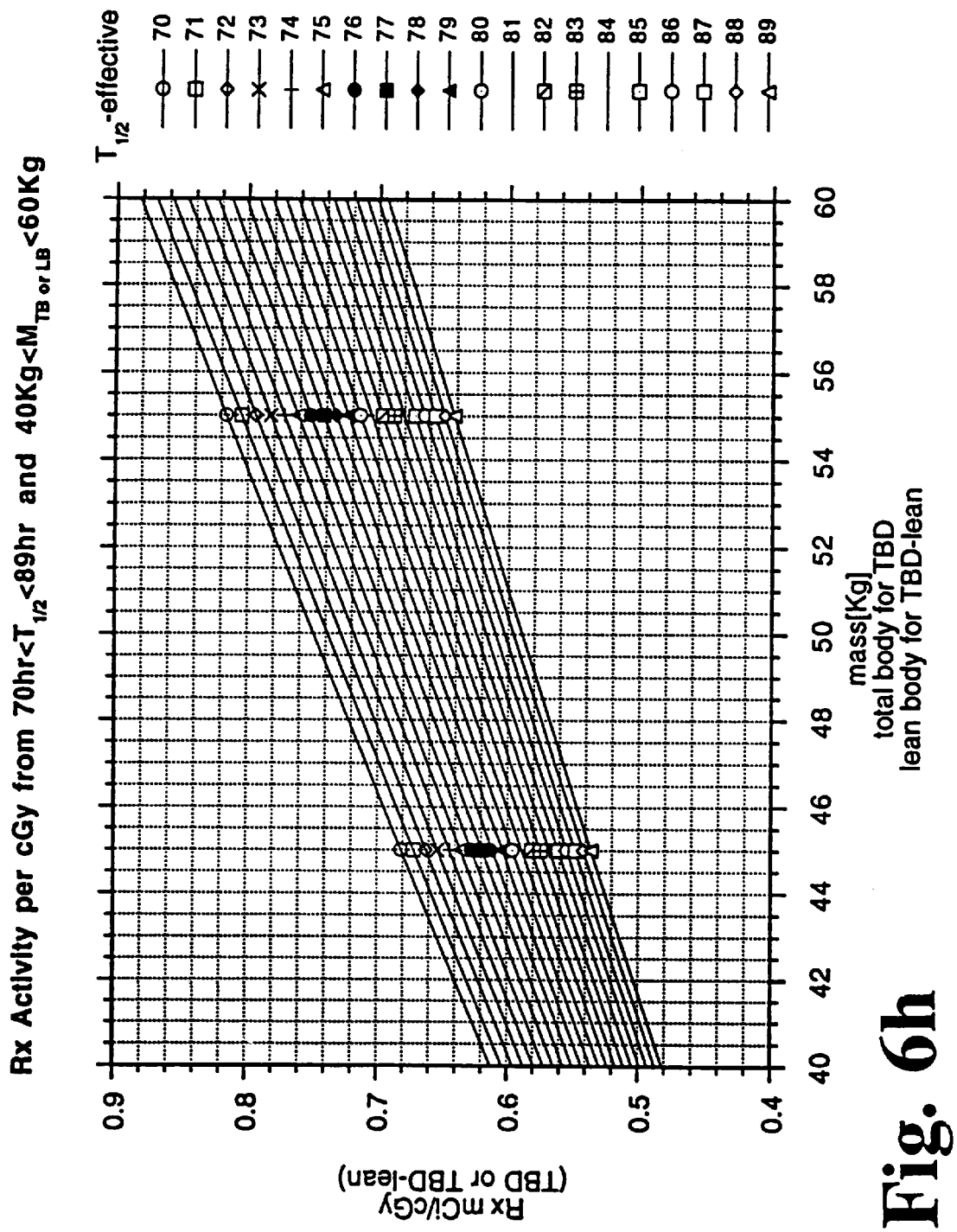
Figure 6I:
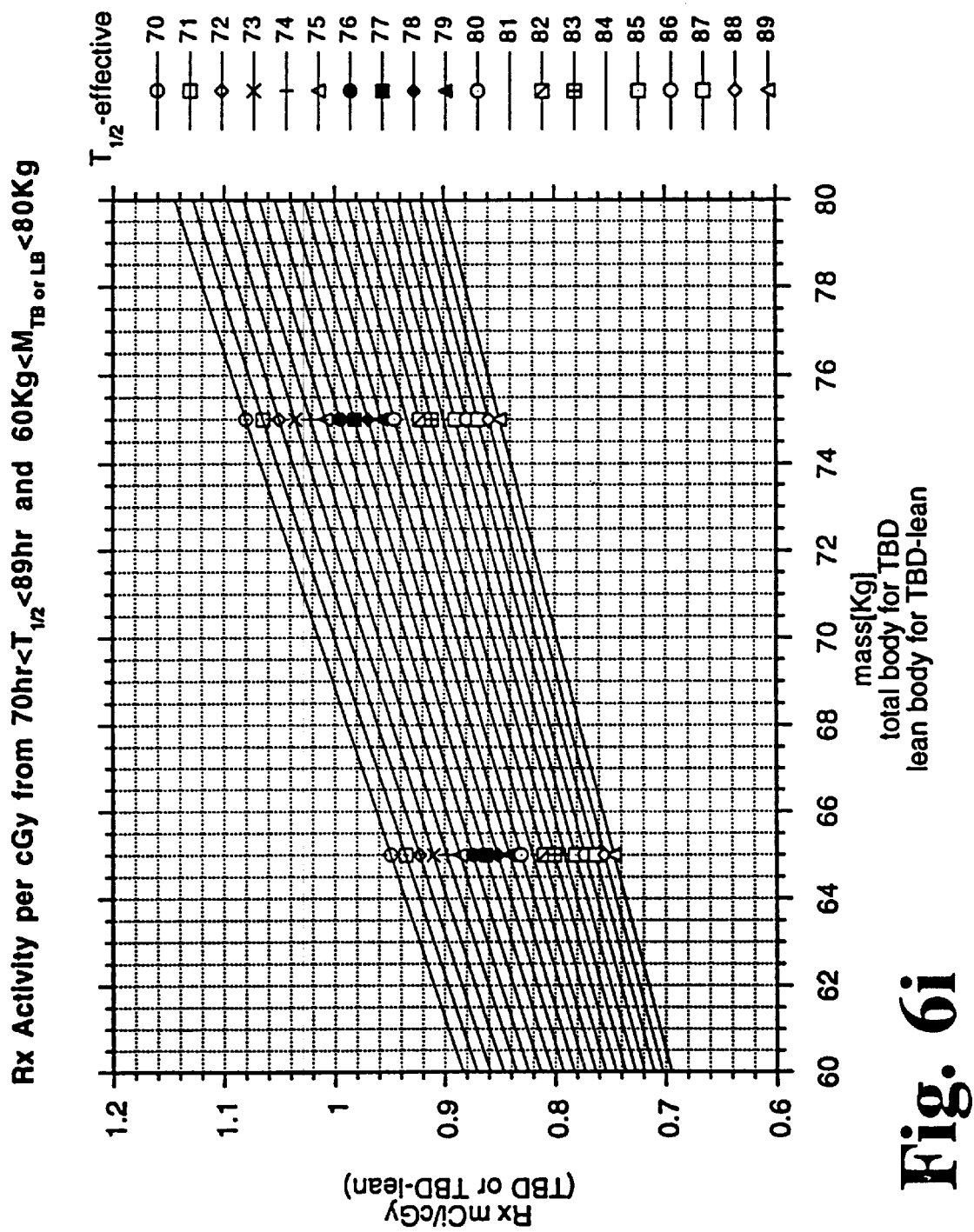
Figure 6J:
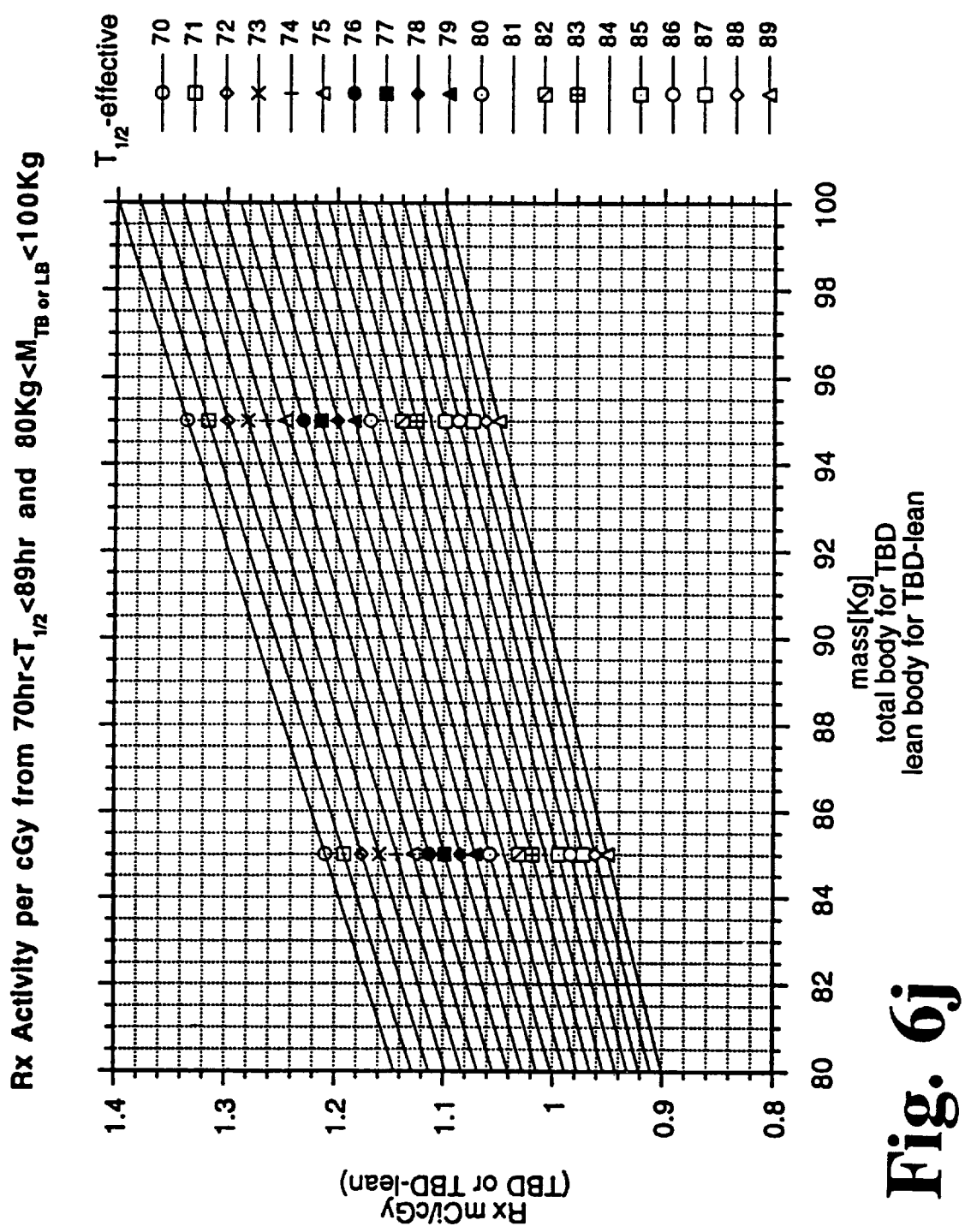
Figure 6K:
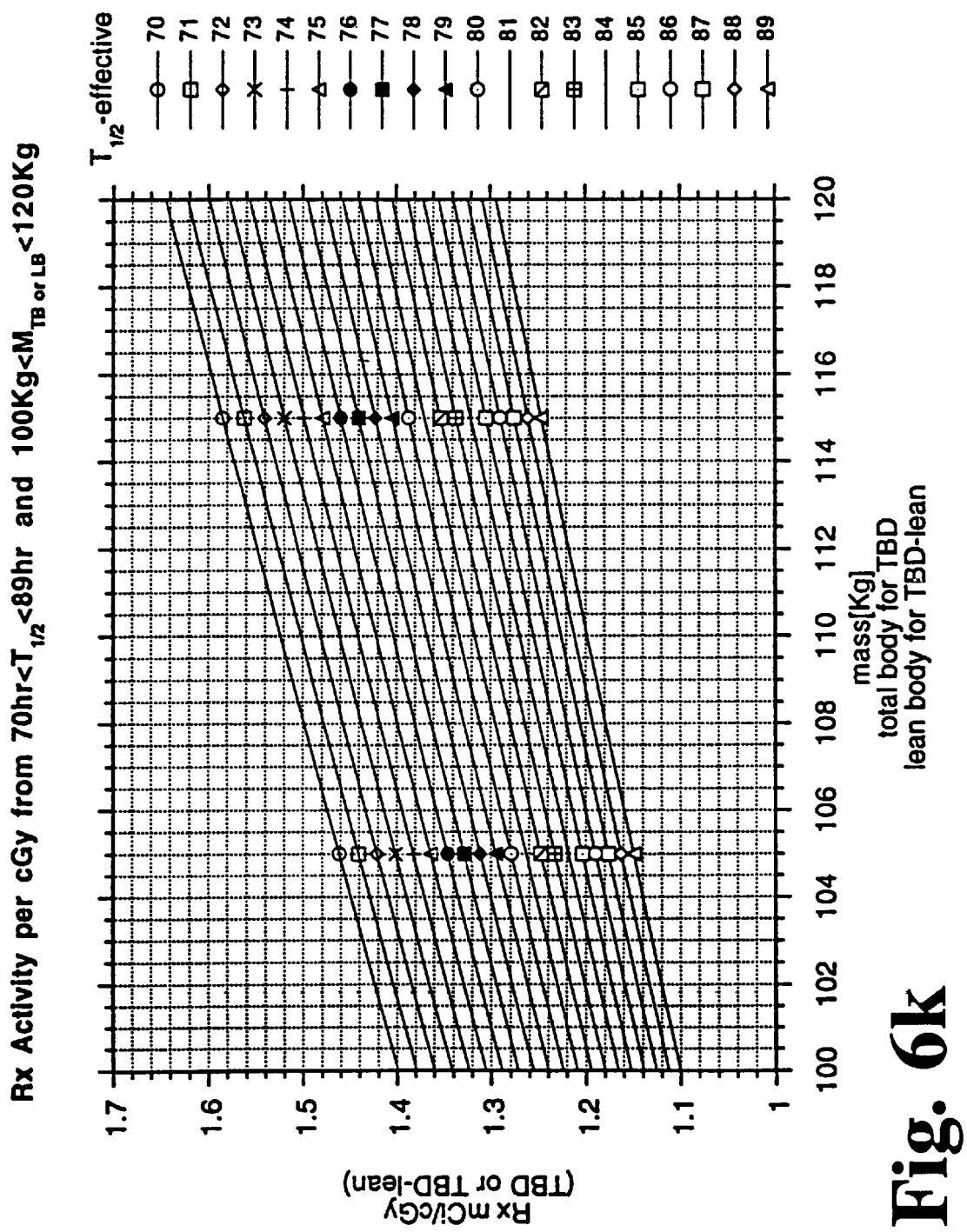
Figure 61:
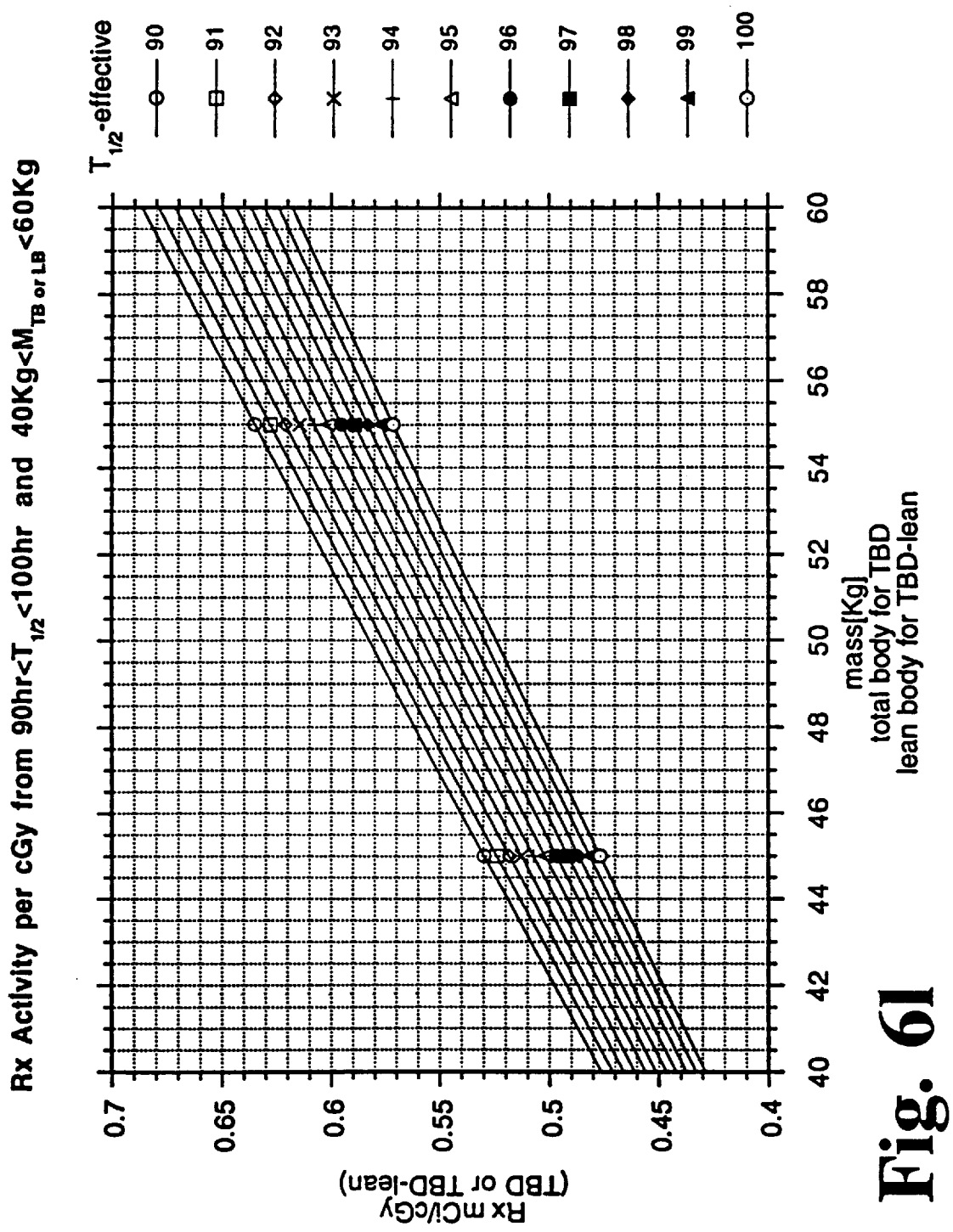
Figure 6M:
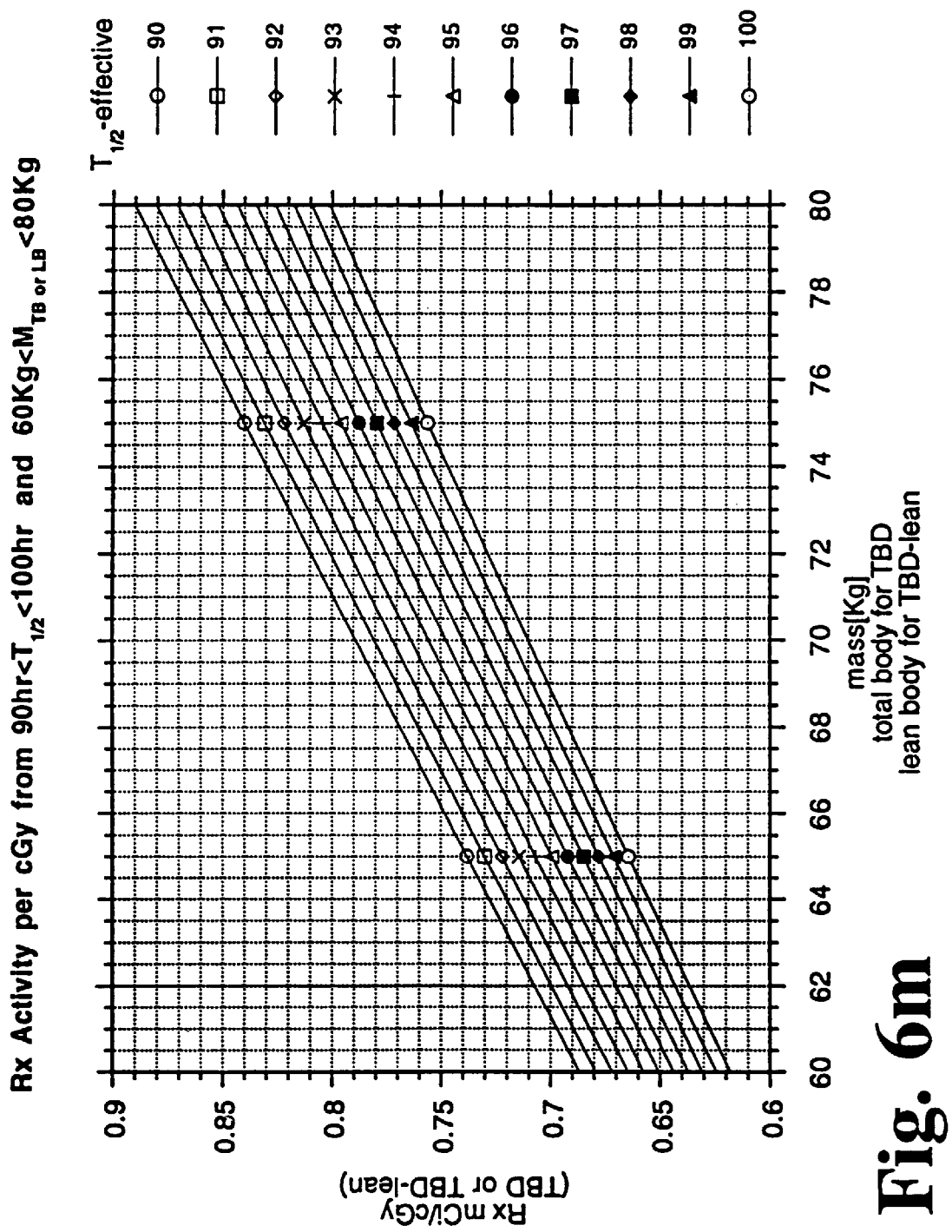
Figure 6N:
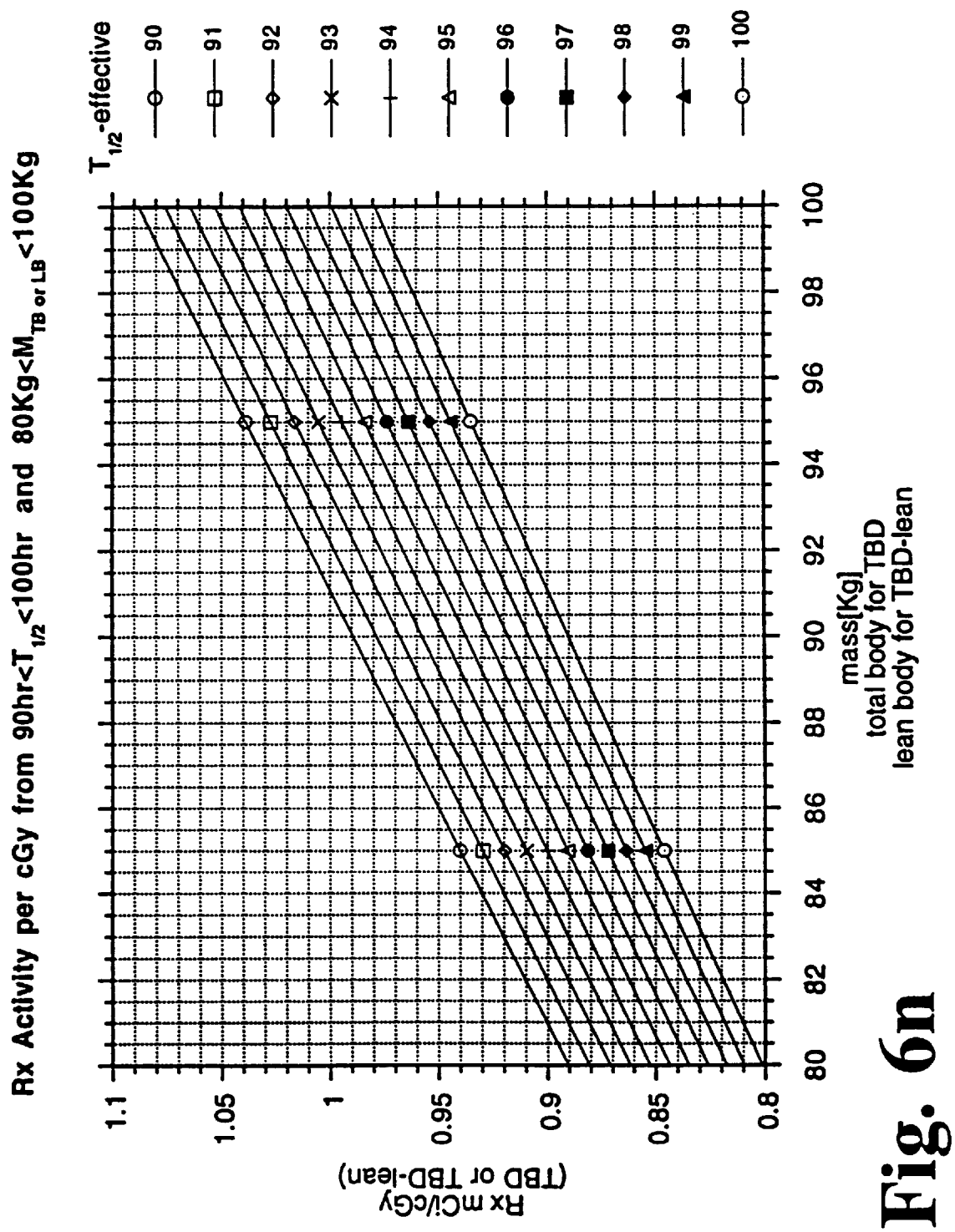
Figure 60:
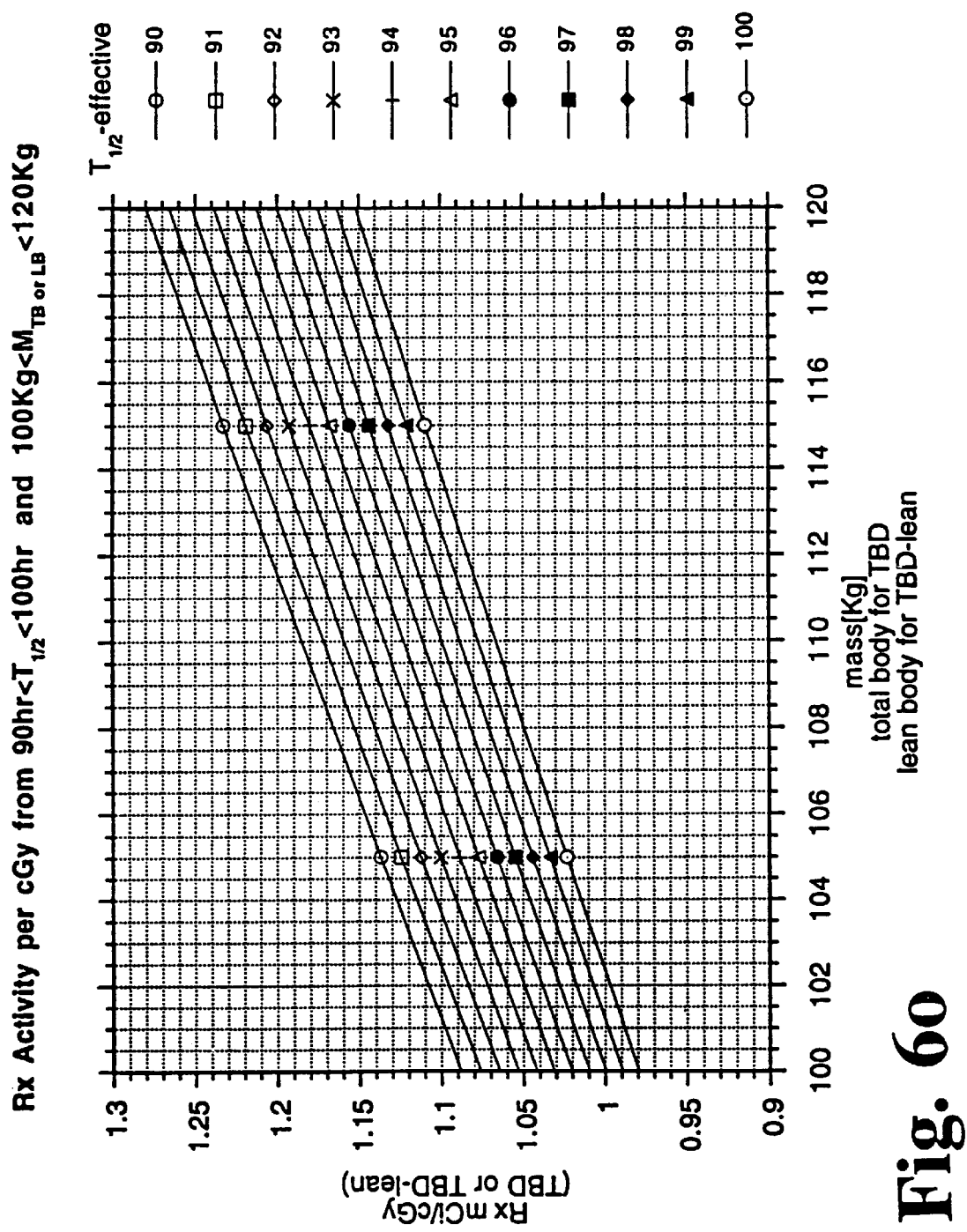
Figure 8:
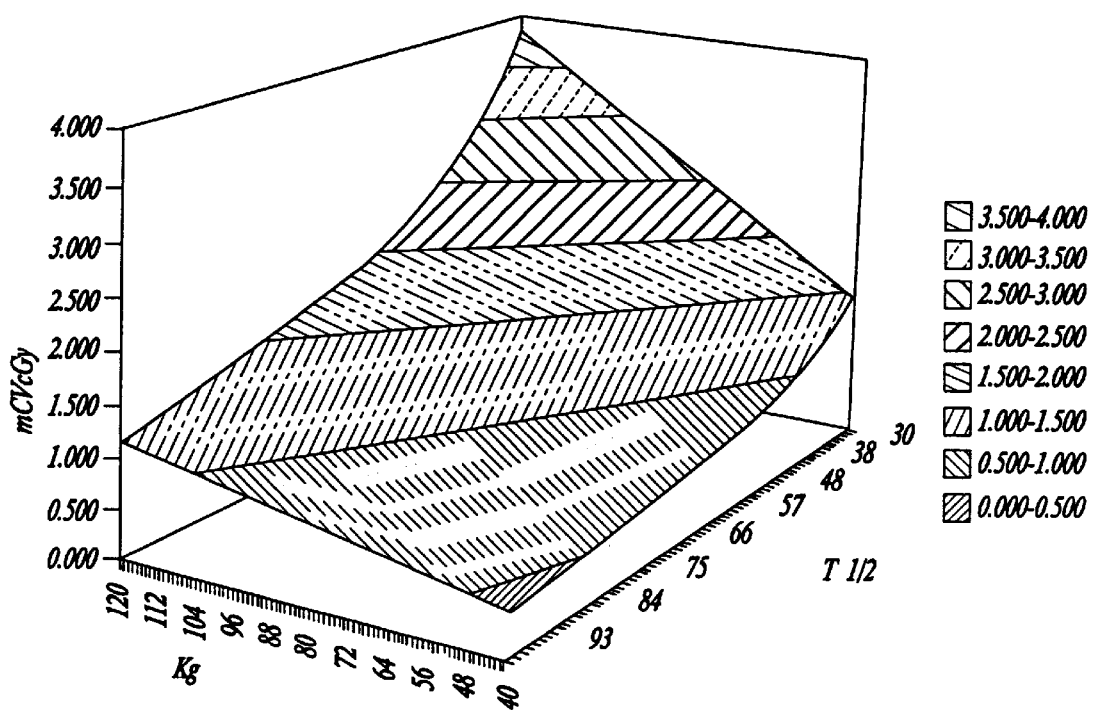
FIG. 8 is a three-dimensional graph based on the series of graphs of FIG. 6.

These individual equations could be solved manually. However, it is preferred that the equations be reduced to graphical and tabular (numerical chart) formats, as illustrated in FIG. 6 (for use in the graphical method). The Lean Body Mass estimates of FIGS. 7a through 7v are taken from the following: Female: LBM=45.5+0.91*(HT—152) [HT in cm, LBM in Kg]; Male: Lbm=48.0+1.06*(HT—152). and FIG. 7 (for use in the tabular method). A three-dimensional representation of the graphical method is illustrated in FIG. 8. Such reductions greatly reduce the need for calculation and allow the method to be practiced without the need for complex computation.

FIG. 6 defines a series of graphs used for determining the therapeutic mCi/cGy to be administered based on known T ½-effective and the patient's mass (in Kg), total body mass (in Kg) for TBD, and lean body mass (in Kg) for TBD-lean. FIG. 7 defines a series of tables used for determining the therapeutic mCi/cGy to be administered based on known T ½-effective and the patient's mass (in Kg), total body mass (in Kg) for TBD, and lean body mass (in Kg) for TBD-lean.

To use the graph of FIG. 6, the known effective half-life is cross-indexed with the patient's weight. The amount of therapeutic millicuries/cGy (for either total body dose or total body dose-lean) is set forth along the Y-axis, and the physician reads along the graph to the left to make this determination. To use the table of FIG. 7, again the known effective half-life is cross-indexed with the patient's weight. The value at the intersection of the weight and T ½-effective is the amount of therapeutic millicuries/cGy.

Once the amount of therapeutic millicuries/cGy is established, this value is multiplied by the amount of desired centigray to be administered to treat a particular disease. These amounts are well known to those skilled in the art, but are not uncommon in the 50–90 cGy range for whole-body dose.

The present invention may be more fully understood by reference to the following examples.

EXAMPLES

A phase-I dose-escalation trial of I-131 labeled B1 antibody for the treatment of patients with non-Hodgkin's lymphoma was undertaken using a dose-escalation scheme designed around increasing levels of total body radiation dose. The overall results of the studies of 21 patients are set forth in the table of FIG. 9. (The study began with 34 patients, hence the listing in the left-hand column of patient numbers with some patient numbers missing. Some of the missing patients, i.e., nos. 3, 11, 12, 17, 18, 20–23, 25, 26, 30, and 33, were bone marrow transplant patients or were patients who were subsequently not treated for various reasons, e.g., development of human antimouse antibody.)

Hematological toxicity was the major toxicity observed in the 21 patients studied that received radioimmunotherapy. Patients were treated with radioimmunotherapy doses calculated from tracer dosimetry studies (NaI probe) to deliver doses to the whole body ranging from 25 to 85 cGy. Hematological toxicity after treatment was assessed by the NCI common criteria, grades 0–4. Nine patients had no toxicity, 5-grade-1, 3-grade-2, 2-grade-3, and 2-grade-4 (grade 4 is the most severe). Total body dose was estimated by modeling the patient as a uniform activity distribution in an ellipsoid for the purpose of calculating the energy absorbed fraction of photons from I-131 decay. The parameter of the present invention, the Total Body Dose-Lean was introduced to account for the fact that obese patients can be modeled as an outer shell of fat (with little radioantibody accumulation) surrounding the active lean body mass. Irradiation of the fat layer would presumably have little effect on hematologic toxicity. Blood clearance and dose was determined from actual tracer blood samples. Marrow residence time was estimated using the assumption that specific activity in marrow is 30% of the specific activity in blood. Resulting correlation between estimated dose parameters from the tracer studies and hematological toxicity grade were as follows:

| Dose Parameter | r-value | p-value (N = 21) |
|---|---|---|
| blood-dose | 0.337 | 0.146 |
| marrow-dose | 0.421 | 0.064 |
| mCi/Kg | 0.270 | 0.236 |

-continued

| Dose Parameter | r-value | p-value (N = 21) |
|---|---|---|
| TBD | 0.430 | 0.052 |
| TBD-lean | 0.523 | 0.015 |

The TBD-lean correlated best with resulting toxicity following radioimmunotherapy in this patient group, offering a clear improvement over estimates of blood, marrow or TB dose.

Figure 10:
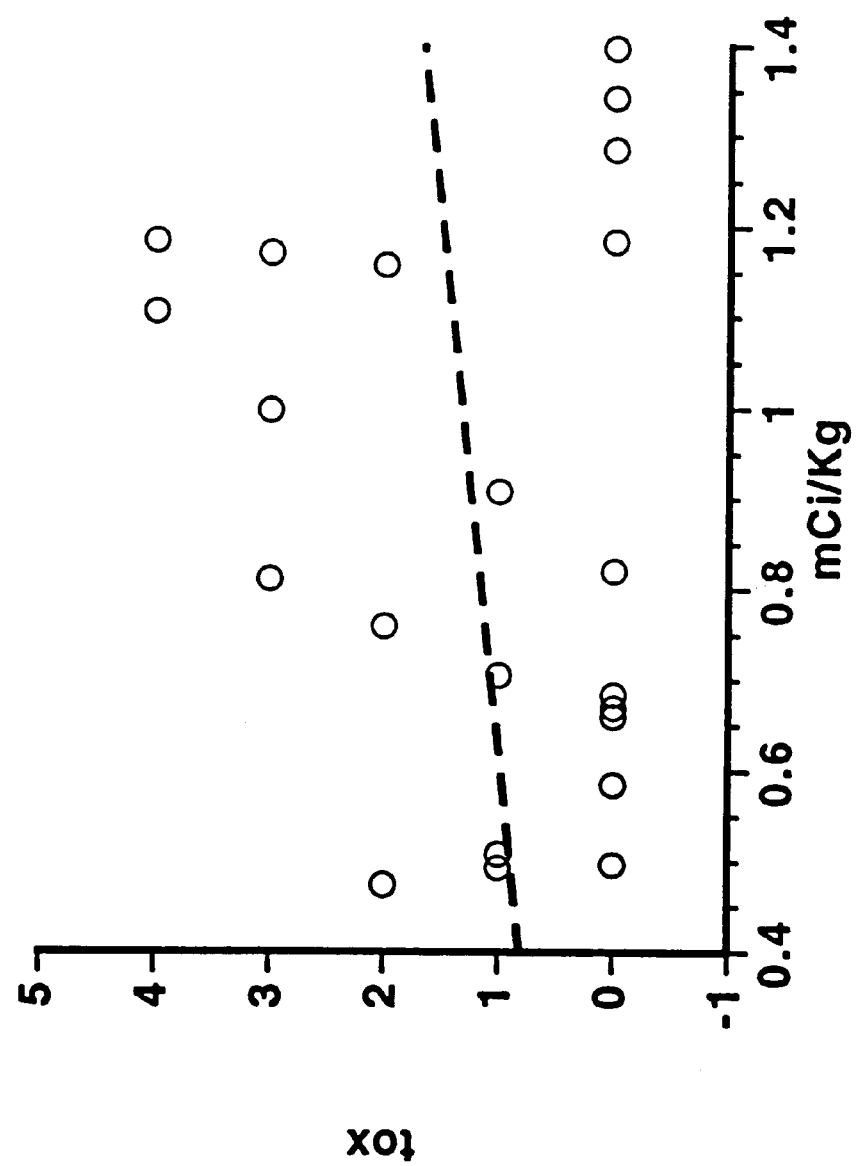
FIG. 10 is a toxicity versus mCi/Kg graph with the data points of the twenty-one sample patients of FIG. 9.

The improvement according to the present invention is clearly observable by reference to the graphs of FIGS. 10–12. With respect first to the graph of FIG. 10, dosage based on simple mCi per Kg of patient weight is set forth. The toxicity level correlates poorly with mCi/Kg due to the assumption of uniform distribution in the patient's total body mass, and also clearance kinetics are not taken into account. FIG. 11 discloses a graph similar to that of FIG. 10, but based upon total body dose (TBD) [cGy]. As illustrated, the toxicity grade from the administered dose correlates better with TBD than for the less exact method that produced the graph of FIG. 10. Finally, FIG. 12 discloses a graph similar to those of FIGS. 10 and 11, but illustrating results produced from reliance on the total body dose-lean (TBD-Lean) [cGy] method. The grade of toxicity from the administered dose is best predicted by the TBD-Lean method than that for the method based on total body dose (shown in FIG. 11) and also the method based simply on mCi/body weight (shown in FIG. 10).

Those skilled in the art can now appreciate from the foregoing description that the broad teachings of the present invention can be implemented in a variety of forms. Therefore, while this invention has been described in connection with particular examples thereof, the true scope of the invention should not be so limited since other modifications will become apparent to the skilled practitioner upon a study of the drawings, specification and following claims.

What is claimed is:

1. method of establishing the optimal effective radiation dose in mCi for treatment of disease in a patient, said method comprising the steps of:
    approximately identifying the fat and lean components of the patient;
    administering to the patient a tracer dose of a radiolabeled antibody;
    establishing the rate of clearance of said tracer dose from the patient's body by direct measurement across multiple time points using a radiation detection device;
    calculating a geometric mean representing an average number of counts of detected radiation;
    plotting the percent of injected activity versus the calculated time from infusion on a graph;
    determining from said graph the effective half-life value of said tracer dose in the patient;
    determining the actual amount of therapeutic mCi per coy based on the effective half-life of said tracer and said weight of the patient in view of said fat and lean components; and
    multiplying said actual amount of therapeutic mCi per cGy by the amount of desired cGy to be delivered to calculate the total therapeutic mCi dose to be administered to the patient.

2. The method of establishing the optimal effective radiation dose of claim 1, wherein said geometric mean is based upon NaI probe measurements.

3. The method of establishing the optimal effective radiation dose of claim 1, wherein said geometric mean is based upon anterior or posterior conjugate view gamma camera imaging data.

4. The method of establishing the optimal effective radiation dose of claim 1, including the further step of determining the percent-injected activity remaining in the patient's body across a plurality of time intervals.

5. The method of establishing the optimal effective radiation dose of claim 4, comprising the further step of plotting said percent-injected activity versus calculated elimination time from infusion on a log-linear graph.

6. The method of establishing the optimal effective radiation dose of claim 5, wherein said log-linear graph includes a 50% injected activity line, said method including the further step of determining said effective half-life from said log-linear graph by identifying the intersection of the best fit line with said 50% injected activity line.

7. The method of establishing the optimal effective radiation dose of claim 1, comprising the further step of cross-indexing said effective half-life with the patient's body weight on a graph having a first axis and a second axis substantially perpendicular to said first axis, said first axis having increments of Rx mCi/cGy and said second axis having increments of body mass to identify the actual amount of therapeutic mCi.

8. The method of establishing the optimal effective radiation dose of claim 1, comprising the further step of cross-indexing said effective half-life with the patient's body weight on a table having a first axis and a second axis substantially perpendicular to said first axis, said first axis having increments of body mass and said second axis having increments of effective half-life to identify the actual amount of therapeutic mCi.

9. A method of establishing the optimal effective radiation dose for treatment of disease in a patient, said method comprising the steps of:
    approximately identifying the fat and lean components of the patient;
    forming a tracer dose including a radiolabeled antibody;
    administering said tracer dose to the patient;
    determining counts using a probe positioned relative to the patient;
    establishing the rate of clearance of said tracer dose from the patient's body using injection start and stop times and said counts for elimination over a period of time;
    identifying a numerical value based on said rate of clearance;
    determining the actual amount of therapeutic mCi per cGy based on said numerical value by cross-indexing said numerical value with the patient's body weight in view of said fat and lean components; and
    multiplying said actual amount of therapeutic mCi per cGy by the desired amount of cGy to be delivered to calculate the total therapeutic mCi dose to be administered to the patient.

10. A method of establishing the optimal effective radiation dose for treatment of disease in a patient, said method comprising the steps of:
    approximately identifying, the fat and lean components of the patient;
    administering to the patient a tracer dose of a radiolabeled antibody;
    determining a rate of clearance of radioactivity from the patient using direct measurement across multiple time points using a radiation detection device;

determining a geometric mean based on said rate of clearance;

determining the percent injected activity remaining in the body for each time point by dividing the counts at a given time by the counters after said tracer is injected;

plotting the percent of injected activity versus the calculated time from infusion on a log linear graph;

identifying the effective half-life value of said tracer in the patient by drawing a line on said plotted graph to determine the intersection of the best fit line with the 50% injected activity line;

cross-indexing said effective half-life on a prepared indicator, said indicator being selected from the group consisting of a graph or a table; and determining the actual amount of therapeutic mCi based on the effective half-life of said tracer at least in part based on said determined fat and lean components.

11. The method of establishing the optimal effective radiation dose of claim 10, including the further step of multiplying said actual amount of therapeutic mCi per cGy by the amount of desired cGy to he delivered to calculate the total therapeutic mCi dose to be administered to the patient.

\* \* \* \* \*

UNITED STATES PATENT AND TRADEMARK OFFICE
CERTIFICATE OF CORRECTION

PATENT NO : 6,022,521

DATED : February 8, 2000

INVENTOR(S) : Richard L. Wahl, Kenneth R. Zasadny

It is certified that error appears in the above-identified patent and that said Letters Patent are hereby corrected as shown below:

Column 11, line 57, claim 1, after "mCi per" delete "coy" and insert --cGy--.

Column 14, line 10, claim 11, after "cGy to" delete "he" and insert --the--.

Signed and Sealed this

Fifteenth Day of May, 2001

Attest:

NICHOLAS P. GODICI

Attesting Officer

Acting Director of the United States Patent and Trademark Office

UNITED STATES PATENT AND TRADEMARK OFFICE
CERTIFICATE OF CORRECTION

PATENT NO. : 6,022,521
DATED : February 8, 2000
INVENTOR(S) : Richard L. Wahl, Kenneth R. Zasadny It is certified that error appears in the above-identified patent and that said Letters Patent is hereby corrected as shown below:

Column 1,
After TITLE, please insert

-- Sponsorship

Work on this invention was sponsored in part by National Institute of Health Grant No. CA56794. The Government has certain rights in the invention.--

Signed and Sealed this

Twenty-eighth Day of August, 2001

*Attest:*

*Attesting Officer*

NICHOLAS P. GODICI
*Acting Director of the United States Patent and Trademark Office*